US012653875B2

(12) United States Patent
Nakhasi et al.

(10) Patent No.: US 12,653,875 B2
(45) Date of Patent: Jun. 16, 2026

(54) LIVE ATTENUATED *Leishmania* PARASITE VACCINES WITH ENHANCED SAFETY CHARACTERISTICS

(71) Applicants: The U.S.A., as represented by the Secretary, Department of Health and Human Services, Silver Spring, MD (US); Ohio State Innovation Foundation, Columbus, OH (US); Gregory Matlashewski, Montreal (CA); Wen-Wei Zhang, Montreal (CA); Patrick Lypaczewski, Montreal (CA)

(72) Inventors: Hira L. Nakhasi, Potomac, MD (US); Ranadhir Dey, Potomac, MD (US); Sreenivas Gannavaram, Potomac, MD (US); Subir Karmakar, Potomac, MD (US); Gregory Matlashewski, Hudson (CA); Abhay Satoskar, Upper Arlington, OH (US); Wen-Wei Zhang, Dorval (CA); Patrick Lypaczewski, Montréal (CA)

(73) Assignees: The United States of America, as represented by the Secretary, Department of Health and Human Services, Silver Spring, MD (US); Ohio State Innovation Foundation, Columbus, OH (US)

(*) Notice: Subject to any disclaimer, the term of this patent is extended or adjusted under 35 U.S.C. 154(b) by 798 days.

(21) Appl. No.: 17/786,129

(22) PCT Filed: Dec. 17, 2020

(86) PCT No.: PCT/US2020/065745
§ 371 (c)(1),
(2) Date: Jun. 16, 2022

(87) PCT Pub. No.: WO2021/127271
PCT Pub. Date: Jun. 24, 2021

(65) Prior Publication Data
US 2023/0039456 A1     Feb. 9, 2023

Related U.S. Application Data

(60) Provisional application No. 62/949,080, filed on Dec. 17, 2019.

(51) Int. Cl.
*A61K 39/008*          (2006.01)
*A61K 39/00*          (2006.01)
(Continued)

(52) U.S. Cl.
CPC ............ *A61K 39/008* (2013.01); *A61P 33/02* (2018.01); *C12N 1/105* (2021.05); *C12N 15/63* (2013.01); *A61K 2039/522* (2013.01)

(58) Field of Classification Search
CPC . A61K 39/008; A61K 2039/522; A61P 33/02; C12N 1/105; C12N 15/63; Y02A 50/30
See application file for complete search history.

(56) References Cited

U.S. PATENT DOCUMENTS 7,887,812 B2     2/2011  Nakhasi et al.
8,877,213 B2     11/2014 Nakhasi et al.
(Continued)

FOREIGN PATENT DOCUMENTS

WO     WO 2005/021030          3/2005
WO     WO-2005021030 A1 *     3/2005    .............. A61P 33/02

OTHER PUBLICATIONS

Selvapandiyan et al. (2009). "Intracellular Replication-Deficient *Leishmania donovani* Induces Long Lasting Protective Immunity against Visceral Leishmaniasis." J. Immunol. 183(3):1813-1820. (Year: 2009).*

(Continued)

*Primary Examiner* — Daniel E Kolker
*Assistant Examiner* — Bailey M Morgan
(74) *Attorney, Agent, or Firm* — Klarquist Sparkman, LLP

(57)          ABSTRACT

Disclosed herein are modified *Leishmania* species and compositions thereof, such as live, attenuated organisms, immunogenic compositions, vaccines, and pharmaceutical com-
(Continued)

positions. Further disclosed are methods related to the modified *Leishmania* species, such as methods of production and methods of use.

16 Claims, 52 Drawing Sheets
(39 of 52 Drawing Sheet(s) Filed in Color)

Specification includes a Sequence Listing.

(51) Int. Cl.

| | |
|---|---|
| *A61P 33/02* | (2006.01) |
| *C12N 1/105* | (2026.01) |
| *C12N 15/63* | (2006.01) |

(56) References Cited

U.S. PATENT DOCUMENTS

| | | |
|---|---|---|
| 2005/0176144 A1 | 8/2005 | O'Daly |
| 2008/0026467 A1 | 1/2008 | Lemesre et al. |
| 2009/0214595 A1 | 8/2009 | Lemesre et al. |

OTHER PUBLICATIONS

Nayak et al. (2018). "A defined medium for *Leishmania* culture allows definition of essential amino acids". Exp. Parisitol., 185:39-52. (Year: 2018).*

Merlen et al. (1999). "*Leishmania* spp.: completely defined medium without serum and macromolecules (CDM/LP) for the continuous in vitro cultivation of infective promastigote forms". Am. J. Trop. Med. Hyg., 60(1):41-50. (Year: 1999).*

Gannavaram et al. (2017). "Whole genome sequencing of live attenuated *Leishmania donovani* parasites reveals novel biomarkers of attenuation and enables product characterization". Sci. Rep., 7:4718. (Year: 2017).*

Karmakar et al. (2017). "Evaluation of safety and efficacy of *Leishmania major* centrin deleted live attenuated parasites as a prophylactic vaccine against cutaneous and visceral leishmaniasis." Am. J. Trop. Med. Hyg. (Supplement), 97:175. (Year: 2017).*

Beneke et al., "LeishGEdit: A Method for Rapid Gene Knockout and Tagging Using CRISPR-Cas9," *Leishmania: Methods and Protocols*, Methods in Molecular Biology, vol. 1971:189-210, 2019.

Dey, et al., "Marker Free Live Attenuated *Leishmania major* (*LMCEN-/-*) Induces Strong Host Protective Immune Response against Vector Bite Transmitted Visceral Leishmaniasis," Abstract 1329, American Society of Tropical Medicine and Hygiene Annual Meeting, *Am. J. Trop. Med. Hyg.*, vol. 101(5 Supplement), p. 408, Nov. 11, 2019.

International Search Report and Written Opinion for PCT/US2020/065745, dated Jun. 8, 2021 (21 pages).

Selvapandiyan et al., "Centrin Gene Disruption Impairs Stage-specific Basal Body Duplication and Cell Cycle Progression in *Leishmania*," *J. Biol. Chem.*, vol. 279:25703-25710, 2004.

Selvapandiyan et al., "Intracellular Replication-Deficient *Leishmania donovani* Induces Long Lasting Protective Immunity against Visceral Leishmaniasis," *J. Immunol.*, vol. 183:1813-1820, 2009.

Zhang et al., "CRISPR-Cas9-Mediated Genome Editing in *Leishmania donovani*," *mBio*, vol. 6:e00861-15, 2015.

Zhang et al., "Single-Strand Annealing Plays a Major Role in Double-Strand DNA Break Repair following CRISPR-Cas9 Cleavage in *Leishmania*," *mSphere*, vol. 4:e00408-19, 2019.

Zhang et al., "A Second Generation Leishmanization Vaccine with a Markerless Attenuated Leishmania major Strain using CRISPR Gene Editing," *Nat. Commun.*, vol. 11:3461, 2020.

Gannavaram et al., "Whole genome sequencing of live attenuated *Leishmania donovani* parasites reveals novel biomarkers of attenuation and enables product characterization," *Sci Rep* 7:4718, 2017 (10 pages).

* cited by examiner

FIG. 1E
FIG. 1F
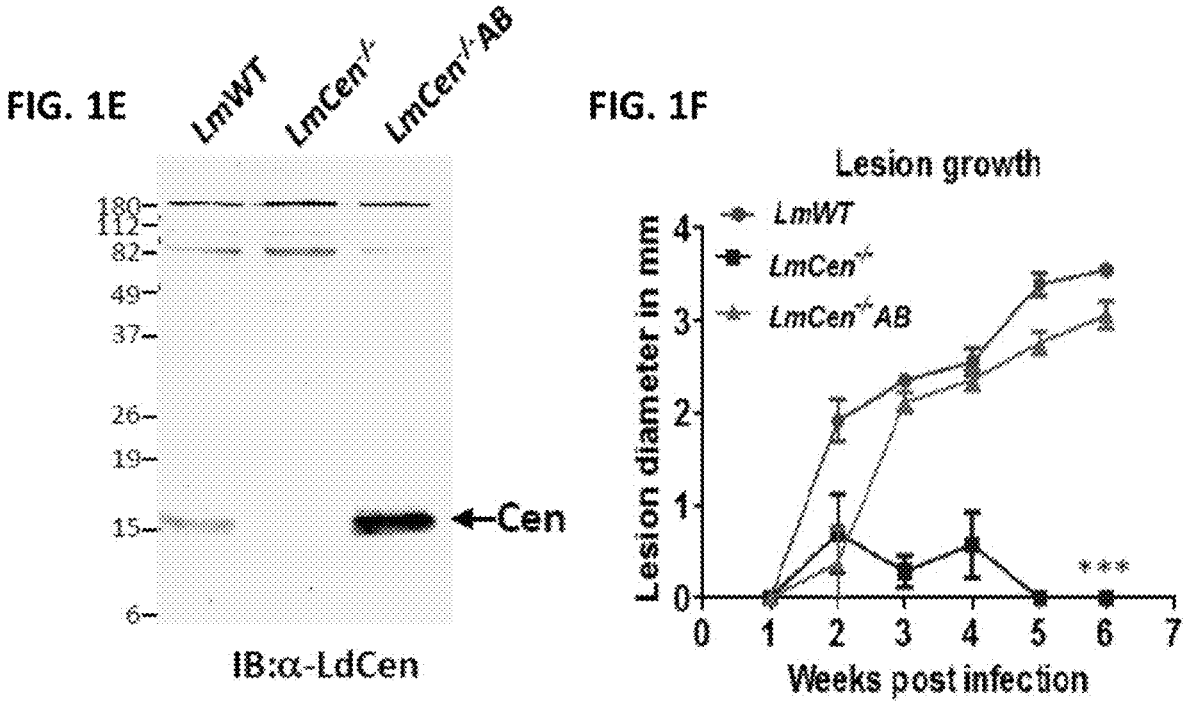
IB:α-LdCen
FIG. 1G
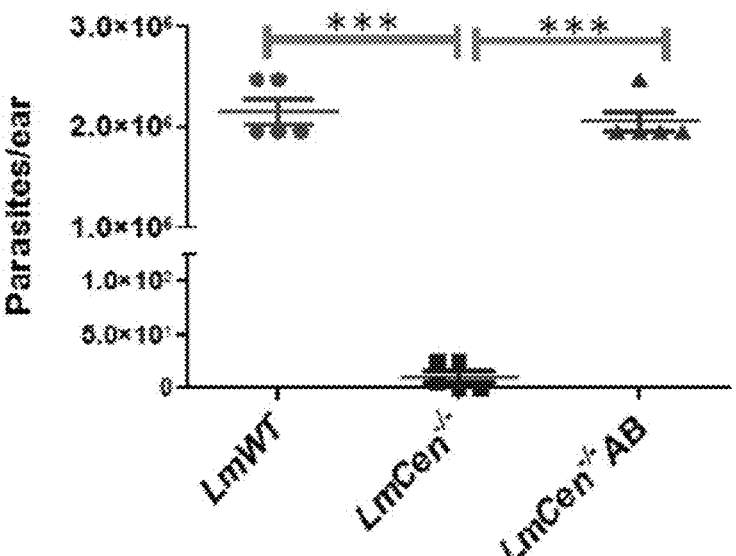

Coverage of centrin genes

1 —— LmjF.07.0710
2 —— LmjF.22.1410
3 —— LmjF.32.0660
4 —— LmjF.34.2390
5 —— LmjF.36.6110

Centrin gene location +/- 1000bp

FIG. 2C

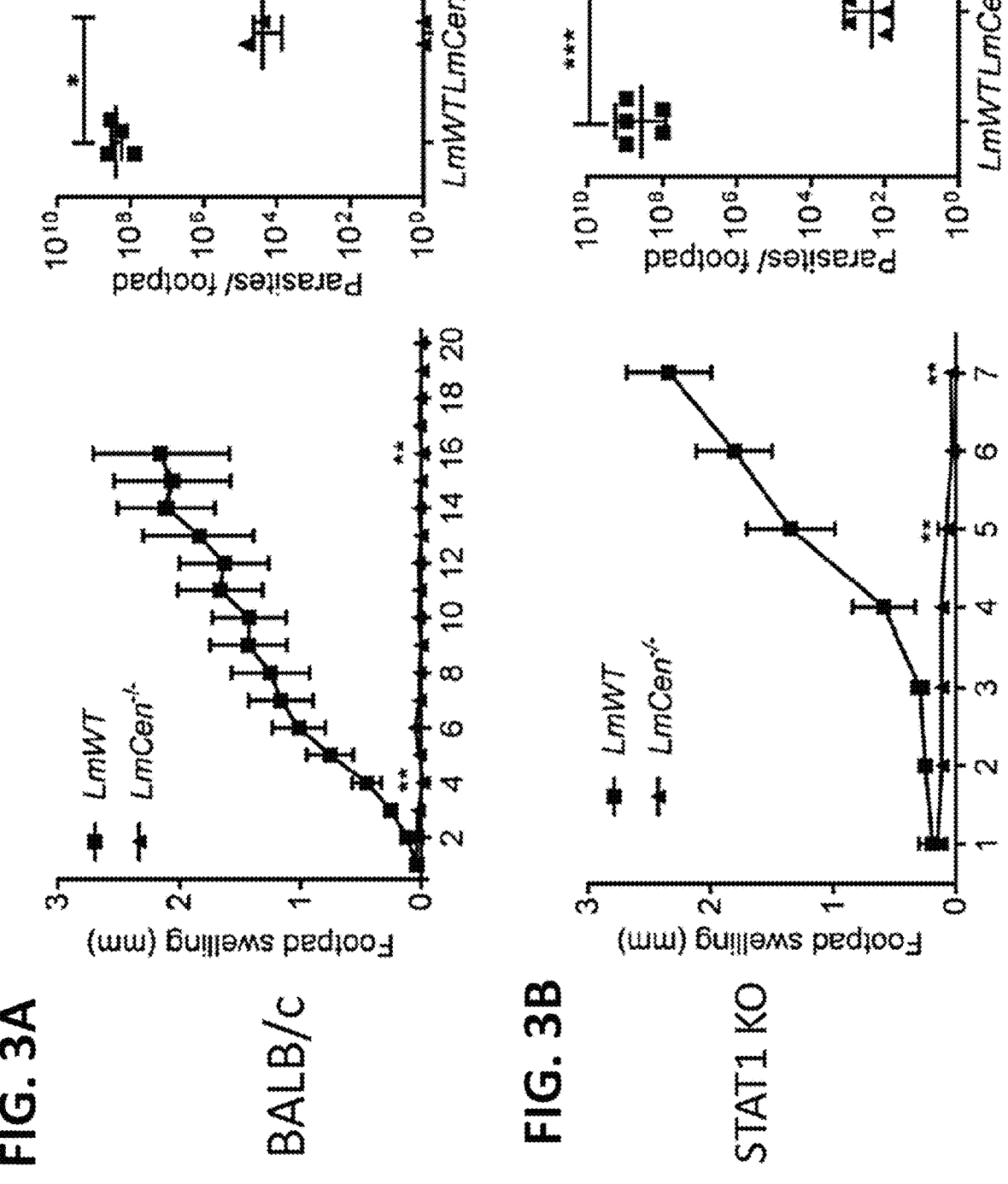

IFN-γ KO

Rag2-KO

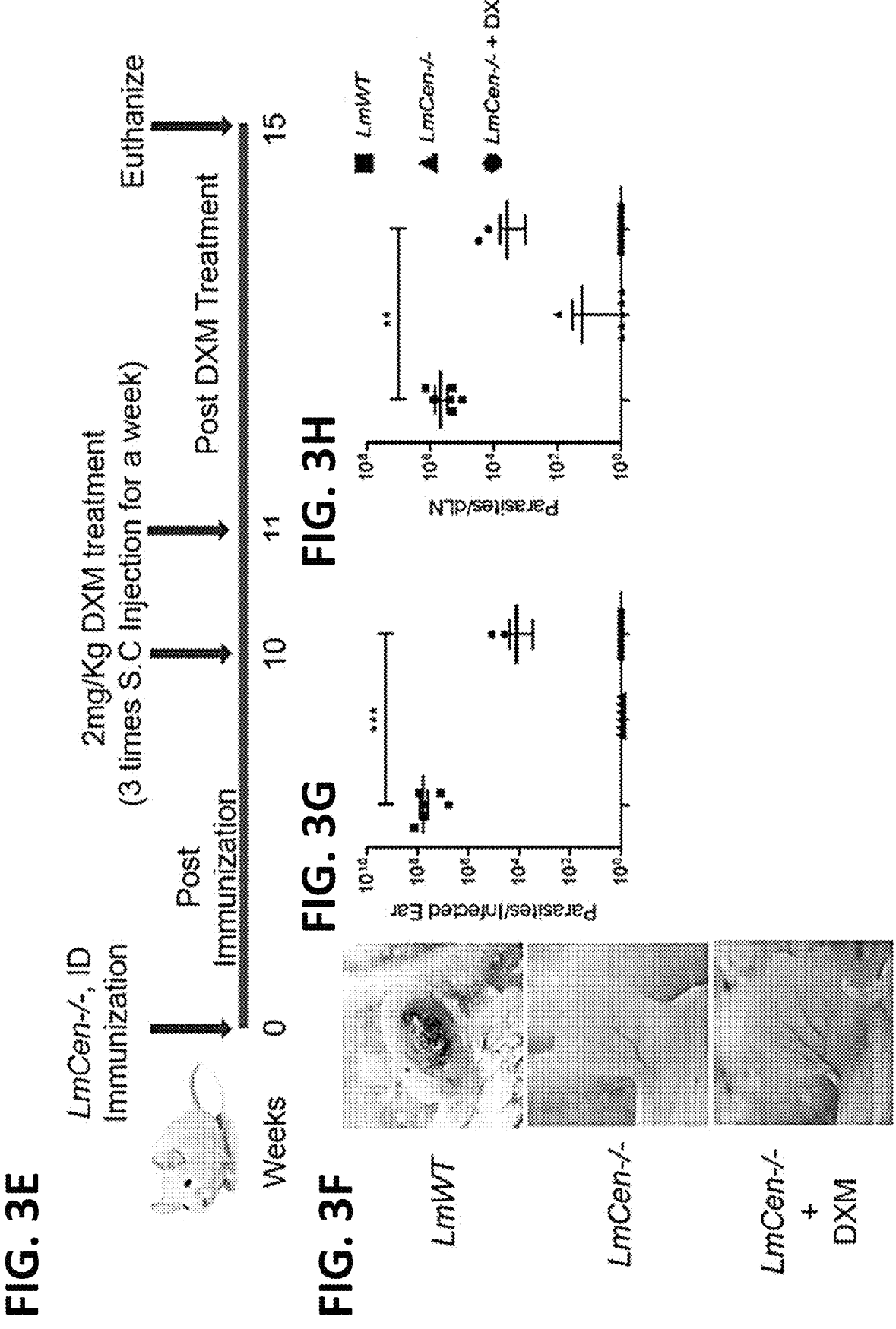

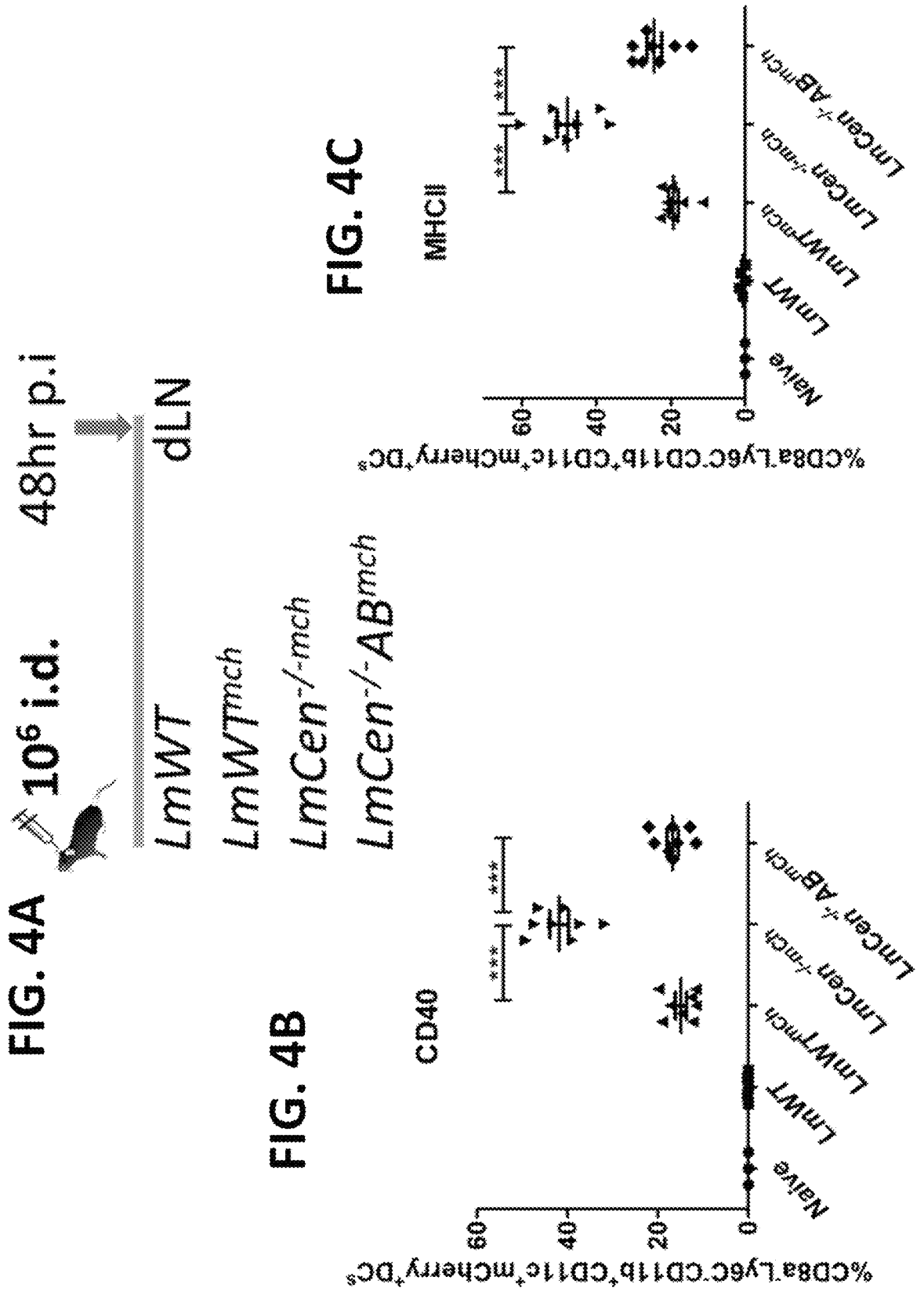

a ▦ Non-Imm Chal
b ▥ Healed Chal
▩ *LmCen*[-/-]Imm Chal a ▦ Non-Imm Chal
b ▥ Healed Chal
▩ *LmCen*[-/-]Imm Chal Rag2 KO

*Lm* WT

*Lm Cen⁻ᐟ⁻*

CD80

CD83

FIG. 12F
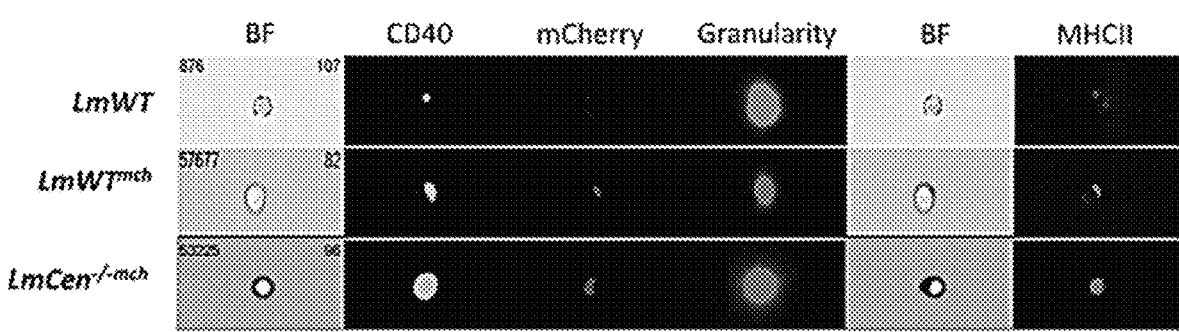
FIG. 12G
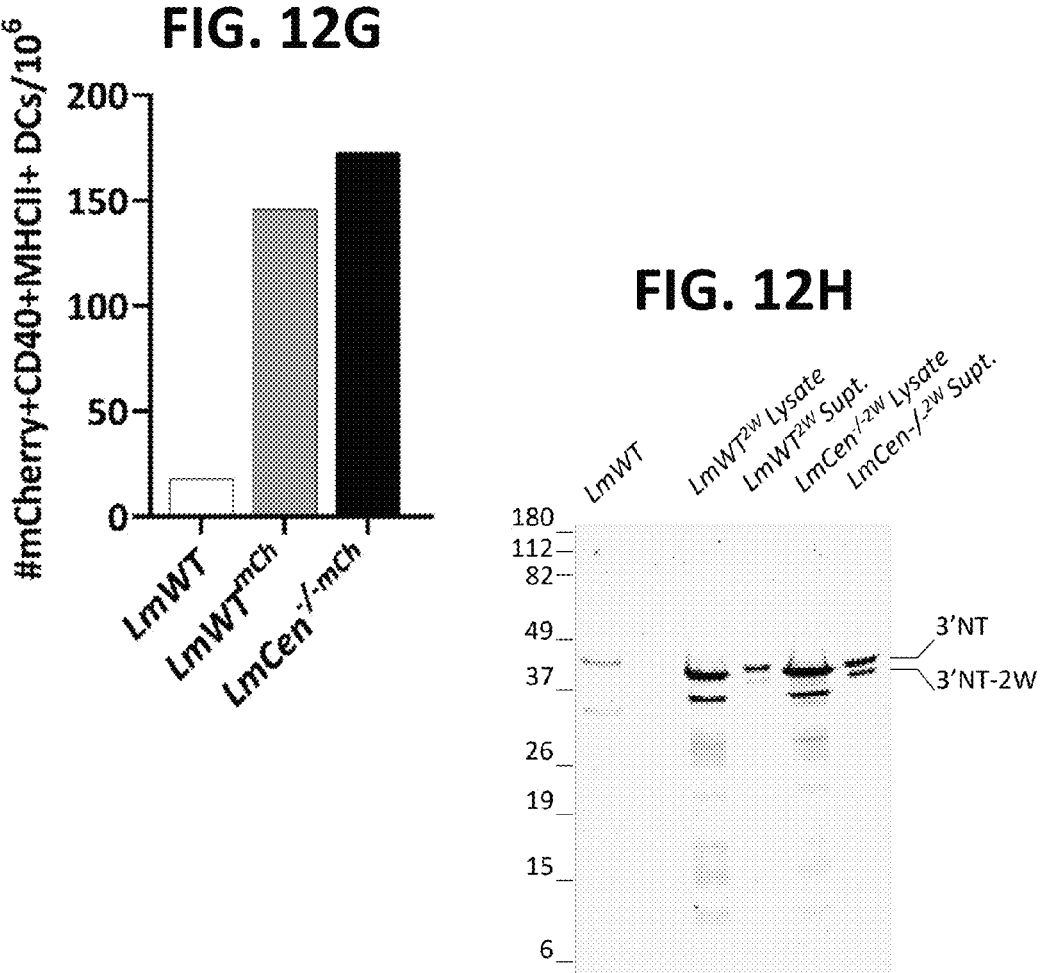
FIG. 12H

*LmCen⁻/⁻*, ID Immunization

*L. major wild type (WR 2885 Strain) needle Challenge*

Euthanize

Post Immunization

Post Challenge

Weeks    0        7

Non-Imm Chal
Imm Chal

Ear Lesion Diameter (mm)

Weeks Post Infection

FIG. 13C

Naive

Non-Imm Chal

Imm Chal challenge with LV39

Imm Chal

Non-Imm
Chal

Challenge with FV9

Imm Chal

Non-Imm
Chal

FIG. 14A
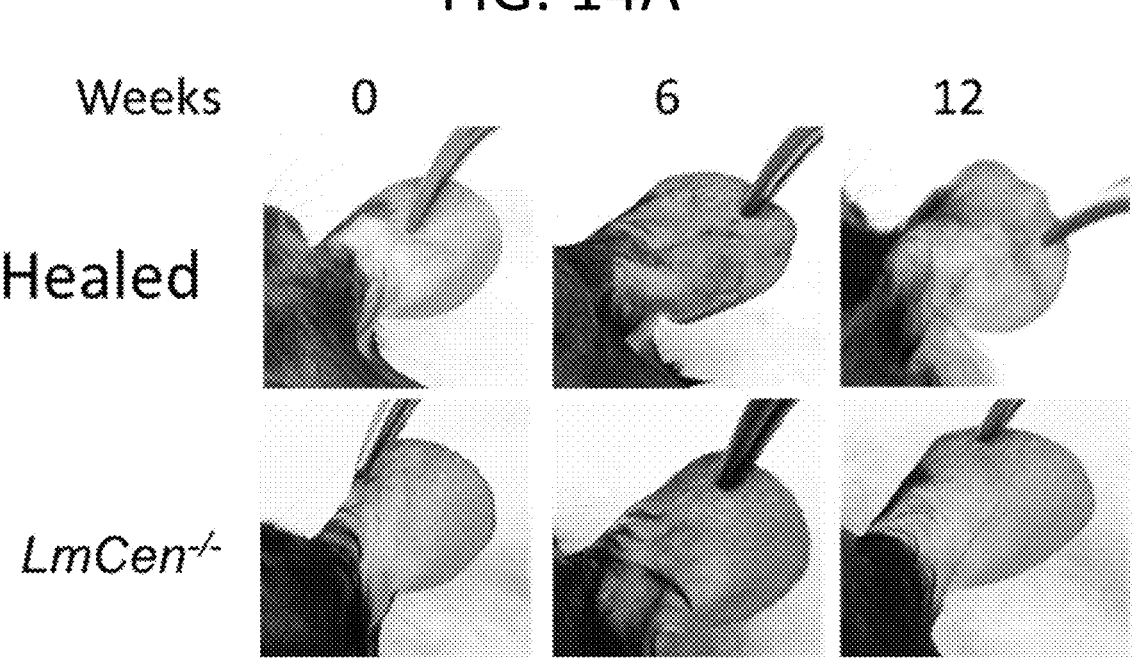
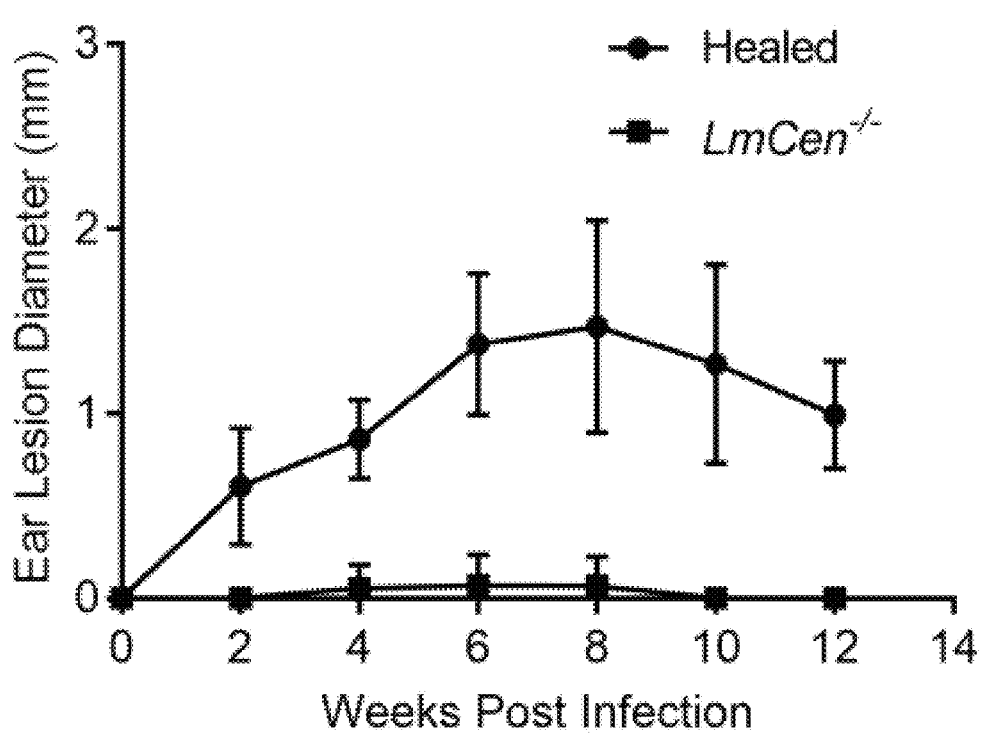

Non-Imm
Chal

Healed
Chal

*LmCen⁻/⁻*
Imm Chal

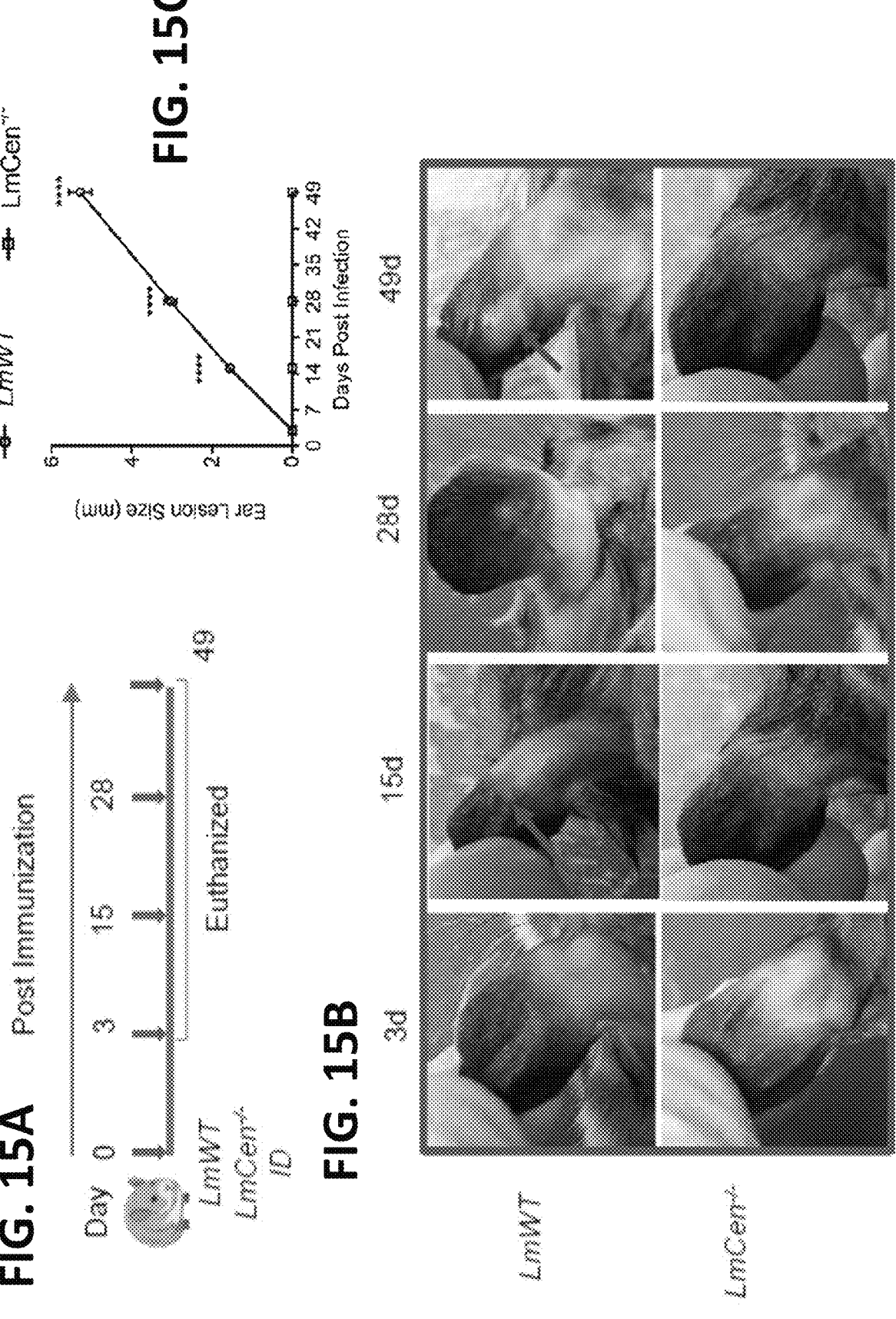

9M Post challenge

Non-Imm Chal

Imm Chal

Naive

Non-Imm Chal
(103gms)

Imm Chal
(160gms)

FIG. 18C

| | LmCen⁻/⁻ grown in serum containing media | LmCen⁻/⁻ grown in serum free media |
|---|---|---|
| Number of scaffolds | 37 | 37 |
| Total size of scaffolds | 30977190 | 30971967 |
| Total scaffold length as percentage of assumed genome size | 103.2573 | 103.2399 |
| Useful amount of scaffold sequences (>=25K nt) | 30977190 | 30971967 |
| % of estimated genome that is useful | 103.2573 | 103.2399 |
| Longest scaffold | 2564668 | 2567294 |
| Shortest scaffold | 262484 | 275137 |
| Number of scaffolds > 1K nt | 37 | 37 |
| Number of scaffolds > 10K nt | 37 | 37 |
| Number of scaffolds > 100K nt | 37 | 37 |
| Number of scaffolds > 1M nt | 11 | 9 |
| Number of scaffolds > 10M nt | 0 | 0 |
| N50 | 1014547 | 968089 |
| L50 | 11 | 11 |
| NG50 | 1027971 | 968089 |
| LG50 | 10 | 11 |
| %A | 20.03161036 | 20.0435 |
| %C | 29.60627804 | 29.60294 |
| %G | 29.38822727 | 29.38735 |
| %T | 20.28757289 | 20.28366 |
| Total Number of Ns | 212600 | 211400 |
| %N | 0.686311444 | 0.682553 |

FIG. 19
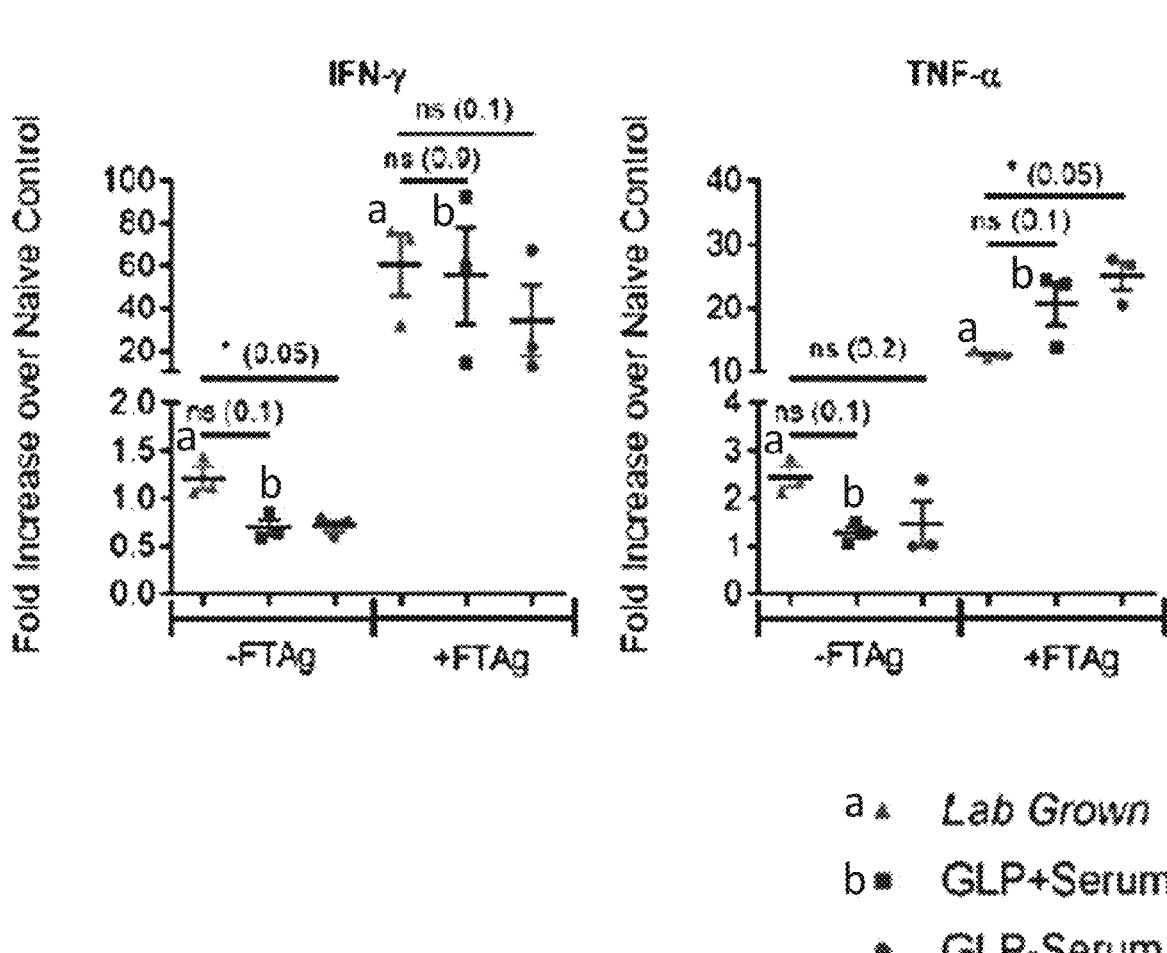
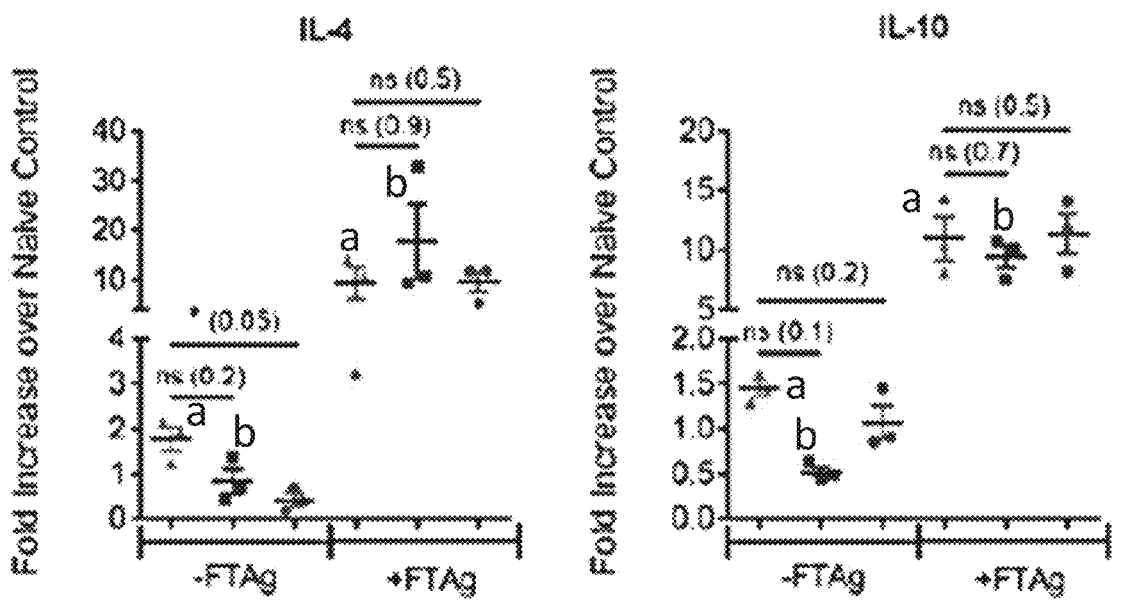

LIVE ATTENUATED *Leishmania* PARASITE VACCINES WITH ENHANCED SAFETY CHARACTERISTICS

CROSS REFERENCE TO RELATED APPLICATIONS

This application is the U.S. National Stage of International Application No. PCT/US2020/065745, filed Dec. 17, 2020, which was published in English under PCT Article 21(2), which claims the benefit of U.S. Provisional Application No. 62/949,080, filed Dec. 17, 2019. The above-listed applications are herein incorporated by reference in their entirety.

PARTIES TO JOINT RESEARCH AGREEMENT

The United States of America, as represented by the Secretary, Department of Health and Human Services; The Ohio State University; and McGill University are parties to joint research agreements governing inventions disclosed herein.

FIELD

The present application relates to modified *Leishmania* species, compositions thereof, and related methods.

BACKGROUND

Leishmaniasis is a neglected disease caused by infection with protozoans of the genus *Leishmania* that is transmitted by infected sand flies (Burza et al., *Lancet* 392, 951-970 (2018)). Worldwide, an estimated 1 billion people are at risk of infection in tropical and subtropical countries, with up to 1.7 million new cases in 98 countries occurring each year (Alvar, J. et al., PLoS One 7, e35671 (2012); WHO, *Relev. Epidemiol. Hebd.* (2016)). The disease pathology ranges from localized skin ulcers (cutaneous leishmaniasis, CL) to fatal systemic disease (visceral leishmaniasis, VL), depending on the species of the infecting *Leishmania* parasite (Burza et al., *Lancet* 392, 951-970 (2018); McCall et al., *PLoS Pathogens* 9, (2013)). Treatment options for leishmaniasis are limited, and there is poor surveillance in the most highly endemic countries (Burza et al., *Lancet* 392, 951-970 (2018); Matlashewski et al., The Lancet Global Health (2014)).

Unlike most parasitic infections, patients who recover from leishmaniasis naturally or following drug treatment develop immunity against re-infection, indicating that the development of an effective vaccine is feasible (Gillespie et al., *Vaccine* 34, 2992-2995 (2016); Alvar et al., *Vaccine* (2013), doi:10.1016/j.vaccine.2012.11.080; Selvapandiyan et al., *Vaccine* (2014), doi:10.1016/j.vaccine.2014.05.009). Furthermore, leishmanization is a process in which deliberate infections with a low dose of virulent *Leishmania major* provides greater than 90% protection against reinfection (Row, Br. *Med. J.* 1, 540 (1912); Marzinowsky, *Trans. R. Soc. Trop. Med. Hyg.* (1924), doi:10.1016/S0035-9203(24)90754-1; Khamesipour et al., *Vaccine* (2005), doi:10.1007/BF02809767). However, leishmanization is no longer practiced due to the resulting skin lesions that last for months at the site of inoculation.

SUMMARY

A prophylactic vaccine for protection against leishmaniasis is desirable for reducing transmission and supporting the elimination of this disease.

Disclosed herein are live, attenuated, and modified *Leishmania* species, such as a genetically modified *Leishmania* species, such as a *Leishmania* species including a non-native nucleic acid molecule (e.g., recombinant or transgenic *Leishmania* species) or a non-native/non-naturally occurring nucleic acid or protein sequence (e.g., a mutated *Leishmania* species). In some embodiments, the *Leishmania* species is a cutaneous or mucocutaneous *Leishmania* species; and the live, attenuated *Leishmania* species includes at least one modification, such as a genetic modification. In some examples, the at least one modification is an amastigote growth-arresting modification, such as a genetic modification that decreases or eliminates expression of a centrin, kharon1, biopterin transporter 1 (Bt1), p27, Lipophosphoglycan biosynthetic protein 2 (Lpg-2), ubiquitin fold modifier-1 (Ufm-1), and/or Ufm1 processing peptidase (Ufsp) gene in the modified *Leishmania*, thereby decreasing or eliminating the biological activity of the respective protein (such as decrease of at least 20%, at least 30%, at least 40%, at least 50%, at least 60%, at least 75%, at least 80%, at least 90%, at least 95%, at least 98%, at least 99%, or 100%). Thus, in some examples, the modified *Leishmania* species includes a functional deletion or genetic inactivation of one or more native gene sequences, resulting in an amastigote growth-arresting phenotype. In some examples, the at least one modification includes, or further includes, a serum-free growth modification, for example by selecting for a *Leishmania* species that can grow or replicate in serum-free media, such as media that includes M199 426.5 ml/L, penicillin 50 units/L, streptomycin 50 μg/L, 1M HEPES 12.5 ml/L, hemin 1000× (5 g/L) 1 ml/L, 25 mM adenosine 5 ml/L, and biotin 0.5 mg/L, but not serum. In some examples, a *Leishmania* species has a non-native/non-naturally occurring nucleic acid or protein sequence that results in the serum-free growth modification/phenotype.

Also disclosed herein are live, attenuated, and modified *Leishmania* species, wherein the *Leishmania* include at least one genetic modification, but do not include an antibiotic-resistance gene. In some embodiments, the at least one genetic modification is an amastigote growth-arresting modification. In some examples, the at least one modification further includes a serum-free growth modification. The live, attenuated *Leishmania* disclosed herein, in some embodiments, can include a *L. major* having at least one modification, wherein the *L. major* does not include an antibiotic-resistance gene and the at least one modification includes an amastigote growth-arresting modification, such as a centrin gene deletion/inactivation.

In addition, disclosed herein are immunogenic compositions that include any of the live, attenuated, and modified *Leishmania* disclosed herein, for example in combination with an adjuvant and/or pharmaceutically acceptable carrier. Vaccines are also disclosed herein that include any of the live, attenuated, and modified *Leishmania* or immunogenic compositions disclosed herein, for example in combination with an adjuvant and/or pharmaceutically acceptable carrier. Also disclosed are pharmaceutical compositions that include any of the live, attenuated, and modified *Leishmania*, immunogenic compositions, or vaccines disclosed herein.

Disclosed herein are methods of treating leishmaniasis in a subject. In some embodiments, the methods include administering any of the live, attenuated, and modified *Leishmania*, immunogenic compositions, vaccines, or pharmaceutical compositions disclosed herein. In some embodiments, the methods further include selecting a subject in need of a treatment for leishmaniasis. In some examples, the leishmaniasis is caused by *Leishmania major, L. donovani,* or *L. mexicana.*

Further disclosed herein are methods of producing an immunogenic composition. In some embodiments, the methods include introducing a first nucleic acid encoding a selection marker and gene-editing complexes into *Leishmania* promastigotes, selecting *Leishmania* promastigotes containing the selection marker, culturing the *Leishmania* promastigotes containing the selection marker, selecting *Leishmania* promastigotes with a slow-growing phenotype, and optionally culturing the *Leishmania* promastigotes with the slow-growing phenotype in serum-free media. Optionally, any of the methods for removing the selection marker as described herein can be used herewith.

The foregoing and other objects and features of the disclosure will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1G show generation of marker-free LmCen$^{-/-}$ parasite, and an example strategy for the generation of centrin-deficient *L. major* using CRISPR-Cas9. FIG. 1A shows the pLdCN vector used to express Cas9 and gRNAa and gRNAb in *Leishmania.* A2-IGS, *L. donovani* A2 gene intergenic sequence; rRNAP, *L. donovani* ribosomal RNA promoter; H, hepatitis delta virus ribozyme; HH, hammerhead ribozyme. FIG. 1B is a schematic of an exemplary gene deletion strategy showing gRNAa (SEQ ID NO: 8) and gRNAb (SEQ ID NO: 9) targeting sites in the *L. major* centrin gene locus and the expected gene deletion sequence after transfection of the cells with a 50 nucleotide oligonucleotide donor (SEQ ID NO: 3; Zhang. & Matlashewski, *MBio* 6, e00861-15 (2015)). The primers F1-R1 and F2-R2 used to detect this deletion are indicated. FIG. 1C shows an example PCR analysis with primers F1-R1 and F2-R2 revealing loss of the centrin gene. Lane 1, wildtype *L. major;* lane 2, *L. major* centrin null mutant. FIG. 1D shows an example sequence analysis confirming the flanking DNA breaks joined together by the transfected 50 nucleotide oligonucleotide donor (SEQ ID NO: 10). FIG. 1E shows an example immunoblot with an α-LdCentrin antibody showing the re-expression of Centrin in LmCen$^{-/-}$ parasites transfected with a pKSNeo-LmCEN plasmid (LmCen$^{-/-}$-AB, Addback). FIG. 1F shows that LmCen$^{-/-}$ was unable to induce ear cutaneous lesions in C57BL/6 mice compared to wildtype *L. major* or the centrin add-back parasites of LmCen$^{-/-}$ showing restored virulence. C57BL/6 mice (n=5 per group) were infected intradermally (1×10$^6$) with LmWT, LmCen$^{-/-}$ or LmCen$^{-/-}$ AB parasites, and the ear lesion development was monitored weekly. FIG. 1G shows parasite load in the infected ears of mice. Parasite burden was determined by limiting dilution assay. Statistical analysis was performed using an unpaired two-tailed t-test (***p<0.0001).

FIGS. 2A-2D show a whole genome analysis of the attenuated LmCen$^{-/-}$ *L. major.* FIG. 2A is a graph showing sequence coverage across each of the centrin gene family members in the LmCen$^{-/-}$ *L. major.* Only the targeted LmjF.22.1410 centrin gene has no sequence reads resulting from CRISPR gene editing. FIG. 2B shows a Southern blot analysis revealing the absence of the LmjF.22.1410 centrin gene in the genome of LmCen$^{-/-}$ parasite compared to wildtype *L. major,* LmWT. FIG. 2C shows the percent sequence coverage (Y-axis) for all protein coding genes from chromosome 1 to 36 (X-axis) by Illumina sequencing of the whole genome of the LmCeni$^{-/-}$ *L. major.* The solid line across the X axis is composed of 8307 dots where each dot represents a gene starting from chromosome 1 (left) to chromosome 36 (right) and is placed according to the portion of the open reading frame supported by sequencing reads. Open circles indicate genes where misalignments of sequencing Illumina reads occurred for some multicopy genes, although these genes were verified to be intact. Filled circles and line markers correspond to the 5 centrin genes across the genome in chromosomes 7, 22, 32, 34, and 36. Only the targeted centrin gene (LmjF.22.1410) has been deleted from the genome and therefore has 0% coverage. FIG. 2D shows coverage of the pLdCN CRISPR plasmid sequence generated from whole genome sequencing. No homologous plasmid sequences were detected in the LmCen$^{-/-}$ genome except for the positions ~5000 to ~6000 corresponding to the *Leishmania donovani* A2 gene intergenic sequence (A2-IGS) that were incorporated into the pLdCN plasmid for expression of the Neo$^R$ gene. Therefore, the A2-IGS genomic sequence reads can align to this portion of the plasmid, although the pLdCN CRISPR plasmid is not present in LmCen$^{-/-}$.

FIGS. 3A-3H shows the safety and non-pathogenicity characteristics of LmCen$^{-/-}$ parasites. BALB/c (FIG. 3A), STAT1 KO (FIG. 3B), IFN-γ KO (FIG. 3C) and Rag2 KO (FIG. 3D) mice were subcutaneously inoculated with the indicated doses of LmWT or LmCen$^{-/-}$ into the right hind footpad. BALB/c (n=4), IFN-γ KO (n=5) and Rag2 KO (n=6) mice were infected with 1×10$^7$ of LmWT (Friedlin V9) or LmCen$^{-/-}$, and STAT1 KO (n=5) mice were infected with 2×10$^8$ of LmWT (Friedlin V9) or LmCen$^{-/-}$. Following infection, footpad swelling was measured weekly by digital caliper. Parasite burden in infected footpad was measured at 5 weeks after infection in BALB/c, at 7 weeks in STAT1 KO or at 15 weeks in IFN-γ KO and Rag2 KO. For the lesion development studies (FIGS. 3A-3D, left panels), asterisks represent the first time point at which significant differences were observed between the LmWT and LmCen$^{-/-}$ groups. The differences in footpad swelling were statistically significant at all time points after the initial observation of the lesion. FIG. 3E shows a schematic representation of the DXM treatment: BALB/c mice were divided into three groups. Group-1 mice (n=6) were infected by intradermal injection of 10$^6$ total stationary phase *L. major* wildtype (LmWT) promastigotes in the ear dermis. Group-2 mice (n=6) and Group-3 mice (n=12) received an intradermal immunization of 1×10$^6$ total stationary phase centrin deleted *L. major* (LmCen$^{-/-}$) promastigotes in the ear dermis. Ten weeks post-inoculation, only Group 3 was treated with 2 mg/kg DXM over one week by 3 subcutaneous injections. All three groups of animals were euthanized four weeks after DXM treatment (15 weeks post-infection). FIG. 3F shows photographs of representative ear of LmWT infected (Group-1) and LmCen$^{-/-}$ (Group-2) (LmCen$^{-/-}$+DXM) (Group-3) mice. Compared to LmWT group, which develops severe pathology in the ear, LmCen$^{-/-}$ (±DXM) immunized mice displayed no ear pathology. FIGS. 3G and 3H show scatter dot plots of parasite load in infected ear (FIG. 3G), and draining lymph node (dLN) (FIG. 3H) of each LmWT and LmCen$^{-/-}$ (±DXM) immunized mice. Parasite burden was determined by limiting dilution assay. Results represent data pooled from two independent experiments with (n=3-6 mice per group each time). Statistical analysis was performed by unpaired two-tailed t-test (p<0.004, *p<0.0006).

FIGS. 4A-4E show the immunogenicity of LmCen$^{-/-}$ parasites. (FIG. 4A) Schematic showing that C57BL/6 mice (n=8) were injected intradermally with mCherry fluorescent protein expressing LmWT (LmWT$^{mCherry}$), LmCen$^{-/-}$ (LmCen$^{-/-mCherry}$) or LmCen$^{-/-}$AB (LmCen$^{-/-}$AB$^{mCherry}$) parasites and draining lymph nodes were collected 48 hours after the infection. Non-mCherry expressing LmWT parasites were used as control. Expression of CD40 (FIG. 4B) and MHCII (FIG. 4C) in LmWT, LmWT$^{mCherry}$, LmCen$^{-/-mCherry}$, LmCen$^{-/-}$AB$^{mCherry}$ immunized mice was measured by flow cytometric analysis. Statistical significance between the means of CD40 and MHCII expression levels (p<0.01; *p<0.001) are shown. To measure expression of IL-12 and IL-6 in vivo, parasitized dendritic cells were sort selected from draining lymph nodes of C57BL/6 mice (n=6) immunized with various parasite strains 48 hours after infection. Expression of IL-12 (FIG. 4D) and IL-6 (FIG. 4E) in LmWT$^{mCherry}$, LmCen$^{-/-mCherry}$, LmCen$^{-/-}$AB$^{mCherry}$ infected dendritic cells was measured by qRT-PCR analysis. The results are representative of two independent experiments. Statistical significance between the means of IL-12 and IL-6 levels normalized to GAPDH expression (***p<0.001) are shown.

(FIG. 5A) Schematic showing C57BL/6 mice (n=4-6) were injected intradermally with LmWT or LmCen$^{-/-}$ parasites secreting the 2W epitope. (FIG. 5B) Activated CD4$^+$ T cells expressing CD62L and IL-7R markers were identified using flow cytometric analysis 11 days post-infection. A gating scheme to identify the activated CD4$^+$ T cells expressing surface markers CD62L and IL-7R from the spleen and lymph nodes of infected mice is shown. (FIG. 5C) To enrich 2W epitope-specific CD4$^+$ T cell populations, 2W tetramers were used. The gating scheme to identify 2W$^+$ specific CD44$^+$CD4$^+$ 2W$^+$ T cell populations is shown. The dump contained markers for B cells (B220), macrophages (F4/80), DCs and monocytes (CD11c, CD11b). Seven weeks following infection, CD4$^+$ central memory T cells (CD4$^+$ T$_{CM}$; 2W$^+$CD62L$^+$IL-7R$^+$CCR7$^+$ T cells) were identified from the spleen and inguinal, axillary, cervical, and submandibular lymph nodes using flow cytometric analysis. The results are representative of three independent experiments. (FIG. 5D) Statistical significance between the CD4$^+$ T cell precursor central memory populations in LmWT and LmCen$^{-/-}$ groups on day 11. (FIG. 5E) Statistical significance between the CD4$^+$ T cell central memory populations in LmWT$^{2W}$ and LmCen$^{-/-2W}$ groups 49 days post-infection (t-test; *p<0.05, **p<0.01).

(FIG. 6A) Schematic representation of the needle challenge procedure. Mice were immunized by intradermal injection in the left ear dermis with 1×10$^6$ stationary phase centrin deleted L. major (LmCen$^{-/-}$) promastigotes. Seven weeks post-immunization, both immunized and age matched naïve animals were challenged with 750 metacyclic L. major wildtype parasites in the right ear by intradermal injection. All the animals were euthanized after 10 weeks post-challenge. (FIG. 6B) Ear lesion size was measured weekly for both LmCen$^{-/-}$ immunized (Imm Chal) and non-immunized (Non-Imm Chal) mice after intradermal challenge with LmWT parasites. The results are the mean±SEM. For the lesion development studies shown in FIG. 6B, asterisks represent the first time point at which significant differences were observed between immunized and non-immunized mice. The differences in ear lesion diameter were statistically significant at all time points after the initial observation of the lesion. FIG. 6C shows photographs (left panel) and histology (H&E stained, right panel) of representative challenged ears of LmCen$^{-/-}$ immunized and non-immunized mice after 10 weeks post-challenge. Arrows indicate inflammatory cells recruited to the area. FIGS. 6D and 6E show scatter dot plots of parasite load of challenged ear (FIG. 6D) and draining lymph node (FIG. 6E) of each LmCen$^{-/-}$ immunized and non-immunized mice. Parasite burden was determined by limiting dilution assay. The results are the mean±SEM. The data were pooled from two independent experiments (n=13 per group). Statistical analysis was performed using an unpaired two-tailed t-test (p<0.001, *p<0.0002).

(FIG. 7A) Schematic representation of the sand fly challenge procedure. Mice were immunized by intradermal injection in the left ear dermis with 1×10$^6$ stationary phase centrin deleted L. major (LmCen$^{-/-}$) promastigotes. Seven weeks post-immunization, both immunized and age matched naïve animals were challenged with ten L. major infected sand flies in the right ear. All the animals were euthanized after 10 weeks post-challenge. (FIG. 7B) Ear lesion thickness was measured weekly for both LmCen$^{-/-}$ immunized (Imm Chal) and non-immunized (Non-Imm Chal) mice after sand fly transmission. Only 1 mouse out of 12 developed a severe lesion. For the lesion development studies shown in FIG. 7B, asterisks represent the first time point at which significant differences were observed between immunized and non-immunized mice. The differences in ear lesion diameter were statistically significant at all time points after the initial observation of the lesion. FIG. 7C shows photographs (left panel) and histology (H&E staining right panel) of representative challenged ear of LmCen$^{-/-}$ immunized and non-immunized mice after 10 weeks post-challenge. Arrows indicate inflammatory cells recruited to the area. The results are the mean±SEM. FIGS. 7D and 7E show a scatter dot plot of parasite load of challenged ear (FIG. 7D) and draining lymph node (dLN) (FIG. 7E) of each LmCen$^{-/-}$ immunized and non-immunized mice. Parasite burden was determined by limiting dilution assay. Results are geometric means with 95% Cl of total 12-14 mice in each group. The data were pooled from two independent experiments. Statistical analysis was performed using a Mann-Whitney two-tailed test (*p<0.05; p<0.01; *p<0.0001).

(FIG. 8A) Schematic representation of the comparative protective immune response. C57BL/6 mice were injected intradermally with 1×10$^4$ metacyclic LmWT (Week-0) or 1×10$^6$ total stationary phase LmCen$^{-/-}$ parasites (Week 4) and immune responses of mice healed from primary LmWT infection (Leishmanized) and LmCen$^{-/-}$ immunized mice were compared following 8 weeks post-LmCen$^{-/-}$ immunization (Week 12). To determine the 20-hour post challenge immune response, healed, LmCen$^{-/-}$ immunized, as well as age matched naïve control mice, were needle challenged with 1×10$^5$ metacyclic L. major wildtype (LmWT) parasites in the contralateral ear (12 weeks). To determine the protective response, healed, LmCen$^{-/-}$ immunized and age matched naïve control mice were challenged with ten L. major infected sand flies in the right ear (week 12). All animals were euthanized after 5 weeks post-sand fly challenge (week 17) and parasite loads were determined. FIG. 8B shows a multiparameter analysis for single, double or triple cytokine secreting CD3⁺CD4⁺ CD44⁺ T cells after 20 hour in-vitro re-stimulation with freeze-thaw *L. major* antigen (LmAg) from pooled ear of healed and LmCen⁻/⁻ immunized group of mice plus naive splenic APCs. The results (mean±SEM) are representative of one independent experiment with 3 mice per group. Statistical analysis was performed by unpaired two-tailed t-test. (FIG. 8C) Results were also represented in pie charts to show the cytokine profile of CD3⁺CD4⁺CD44⁺ T cells in response to LmFTAg re-stimulation expressing any one cytokine (a, IL-2; b, IFN-γ; and b, TNF-α), any two cytokines (d, TNF-α⁺IFN-γ⁺; and e, TNF-α⁺IL-2⁺), or all three cytokines (f, IL-2⁺TNF-α⁺IFN-γ⁺). The data presented are representative of single experiments. Mean and SEM of three mice in each group are shown. ns, $p>0.2$. (FIGS. 8D and 8E) Analysis of the early immune response following needle challenge with wildtype *L. major*-parasites. Twenty hours post-challenge, ear-derived cells were analyzed for IFN-γ-producing total CD4+CD44hi T cells (FIG. 8D) and CD3⁺CD4⁺CD44ʰⁱT-bet⁺Ly-6C⁺ T effector cells (FIG. 8E) in response to 12-14 h in-vitro re-stimulation with freeze-thaw *L. major* antigen (LmAg) plus naive splenic APCs. The results (mean±SEM) are representative of two independent experiment with 3 mice per group. Statistical analysis was performed by unpaired two-tailed t-test (ns, p-0.13, *$p<0.04$). (FIGS. 8F and 8G) Five weeks post-challenge, both ear and draining lymph node parasite load were determined by serial dilution. The results are the geometric means with 95% CI of total 5-8 mice in each group. The data are representative of one independent experiment. Statistical analysis was performed using a non-parametric Mann-Whitney two-tailed test (ns, p-0.34; **$p<0.004$).

(FIG. 9A) Sequence of the *Leishmania major* centrin gene (LmjF.22.1410; SEQ ID NO: 16) and its flanking sequences. The CRISPR gRNAa and gRNAb targeting sites in the 5' and 3' centrin gene flanking sequences and PCR primers (underlined) used to confirm deletion of the centrin gene are indicated at the right. (FIG. 9B) PCR analysis showing loss of antibiotic resistance CRISPR pLdCN plasmid in LmCen(−) cells after culture in G418 free medium for one month. To remove the antibiotic resistance CRISPR plasmid, these LmCen(−) cells were cultured in G418 free medium for several weeks before being subject to cloning in a 96-well plate (free of G418). Once the cell density in the 96-well plates reached approximately 5×10⁶ per ml, 5 μl of the cell culture from each well of the 96-well plates was transferred to a second 96-well plate with 100 μl medium per well containing 100 μg/ml G418. The genomic DNA extracted from LmCen−/− cells which were still able or not able to grow in G418 containing medium were subject to PCR analysis with the CRISPR plasmid specific primers (LdrP+pspneoR). No CRISPR plasmid specific PCR band was detected in the LmCen−/− cells which had lost the ability to grow in G418 containing culture medium, and the 604 bp F2+R2 band from the genome derived sequence could be detected in both G418 resistant and sensitive LmCen−/− cells. (FIG. 9C) LmCen−/− cells (Cen(−)) grow slower than wild-type *L. major* (LmWT) in promastigotes culture. *L. major* promastigotes were inoculated in a 96-well plate at a concentration of 106 per ml, 120 μl per well and 5 wells per sample. Promastigote growth was monitored by measuring the optical density in these wells at a wavelength of 600 nm (OD₆₀₀) during the following 4 days. The data shown are the mean plus SEM. The cell density differences between LmWT and LmCen−/− cells at days 2, 3 and 4 post-inoculation were statistically significant ($p<0.05$). Data are representative of three independent experiments. (FIG. 9D) Human macrophages differentiated from monocytes were infected with stationary phase promastigote parasites from LmWT and LmCen−/− for six hours (10:1 parasite-to-macrophage ratio). The number of amastigotes in these cultures was determined over 8 days by microscopic observation of Diff-quik reagent stained slides. The data are expressed as the number of amastigotes per 100 macrophages. Error bars indicate the standard deviation (***$p<0.001$).

(FIG. 10A) Ear lesion diameters were measured after 4 weeks of dexamethasone (DXM) treatment (15 weeks post-parasite infection) in LmWT and LmCen−/− (±DXM) immunized mice. Results are mean±SEM, of 1 ear, 6-12 mice per group. (FIG. 10B) Agarose gel (1%) electrophoresis results for the characterization of LmCen−/− parasites isolated from LmCen−/− plus DXM treated group using *L. major* centrin gene-specific primers. Lane-1, PCR results from the genomic DNA of parasites isolated from LmCen−/− plus DXM treated group; Lane-2, PCR results from the genomic DNA of parasites isolated from LmWT group; Lane-3, PCR results from the plasmid DNA containing centrin gene as a positive control; and Lane 4, 1 kb DNA ladder (Bioline). The arrow indicates the absence of main product bands (centrin gene) of 450 bp in Lane-1. (FIG. 10C) Representative photographs of footpad of Rag2 KO mice at 15 weeks post subcutaneous infection with 1×10⁷ LmCen−/− or LmWT. (FIG. 10D) Parasite burden in spleen and liver of Rag2 KO mice at 15 weeks post subcutaneous infection with 1×10⁷ of LmCen−/− or LmWT into footpad.

FIGS. 12A-12J show LmCen−/− immunization induced immunogenicity. (FIG. 12A) C57BL/6 mice were infected with LmWT, LmWTᵐᶜʰᵉʳʳʸ, LmCen−/−ᵐᶜʰᵉʳʳʸ, LmCen−/− ABᵐᶜʰᵉʳʳʸ parasites and 48 hours following infection, draining lymph nodes were collected from the mice. Gating scheme to identify the parasitized CD11c+ dendritic cells from the infected mice is shown. Parasitized live DCs were identified as CD3−, CD8a−, Ly6C−, CD11b+CD11c+ mCherry+ cells. Expression of co-stimulatory molecules such as CD40, CD80, CD83, CD86 and MHCII was measured on parasitized DCs. Non-significant differences in the expression of CD80 (FIG. 12B), CD83 (FIG. 12C) and CD86 (FIG. 12D) between LmWT, LmCen−/− and LmCen−/−AB parasite infections are shown. (FIG. 12E) To measure expression of IL-12 and IL-6 in vivo (shown in FIGS. 4D and 4E), parasitized dendritic cells were sort selected from draining lymph nodes of C57BL/6 mice immunized with various parasites strains 48 hours after infection. Gating scheme to identify the parasitized Ly6c−, CD11b+, CD11c+ dendritic cells from the infected mice is shown. (FIG. 12F) Imageflow diagram showing the mCherry expression on the sort selected parasitized DCs and expression of CD40 and MHCII on the parasitized DCs. (FIG. 12G) Graph showing the enumeration of mCherry+ CD40+MHCII+DCs in three experimental groups in the image stream analysis. (FIG. 12H) Immunoblot showing the recombinant LmWT or LmCen−/− parasites expressing a secretory 2W epitope fused to 3' nucleotidase protein in parasite cell lysates and culture supernatants. (FIG. 12I) Flow cytometric analysis showing the binding of CD4 T cell populations from LmCen$^{-/-2w}$ infected mice to either PE-labeled 2W tetramer or an isotype control tetramer: 1-A(b) human CLIP 87-101 PVSKMRMATPLLMQA (SEQ ID NO: 13). (FIG. 12J) Flow cytometric analysis showing the binding of CD4+ T cell populations from naïve uninfected mice to either PE-labeled 2W tetramer or an isotype control tetramer: I-A(b) human CLIP 87-101 PVSKMRMATPLL-MQA (SEQ ID NO: 13).

FIGS. 13A-13G show protective efficacy of LmCen−/− parasites against virulent *L. major* needle challenge in BALB/c mice. (FIG. 13A) Schematic representation of the needle challenge procedure. BALB/c mice were immunized by intradermal injection in the left ear dermis with $1 \times 10^6$ stationary phase centrin-deleted *L. major* (LmCen−/−) promastigotes. Seven weeks post-immunization, both immunized and age matched naïve animals were challenged with 750 metacyclic *L. major* wild type parasites (strain WR2885) in the right ear by intradermal injection. All animals were euthanized after 10 weeks post challenge. (FIG. 13B) Ear lesion size was measured weekly for both LmCen−/− immunized (Imm Chal) and non-immunized (Non-Imm Chal) mice after intradermal challenge with LmWT parasites. The results are the mean±SEM of 1 ear, 5 mice per group. (FIG. 13C) Representative photographs of challenged ear of LmCen−/− immunized (Imm Chal) and non-immunized (Non-Imm Chal) mice after 10 weeks post challenge. Immunized challenged mice displayed significantly reduced ear lesion size and inflammation. Arrows indicate inflammatory cells recruited to the area. Parasite load of each LmCen−/− immunized and non-immunized mice in ear (FIG. 13D) and dLN (FIG. 13E). Parasite burden was determined by limiting dilution assay. The results are representative of one independent experiment with five mice per group (females, 5-8 weeks old). Statistical analysis was performed using an unpaired one-tailed t-test (*p<0.04; p<0.009, *p<0.0005). (FIG. 13F) BALB/c mice were immunized intradermally in the ear with $1 \times 10^7$ LmCen−/− and at 6 weeks post-immunization, mice were challenged intradermally in the alternate ear with 5,000 stationary phage FV9 *L. major* promastigotes. Representative photographs of ear lesions of immunized and non-immunized mice at 14 weeks post-challenge infection are shown. (FIG. 13G) BALB/c mice were immunized subcutaneously in the footpad with $2 \times 10^8$ LmCen−/− parasites and six weeks post-immunization were challenged intradermally in the ear with 10,000 LV39 *L. major* parasites. Representative photographs of ear lesion of immunized and non-immunized mice at 10 weeks post-challenge infection are shown.

FIGS. 14A-14D immunization induces comparable host protective immune response to leishmanization. C57BL/6 mice were injected intradermally with $10^4$ metacyclic LmWT or $1 \times 10^6$ total stationary phase LmCen−/− parasites and immune responses between healed from primary LmWT infection (Leishmanized) and LmCen−/− immunized mice were compared following 8 weeks post-LmCen−/− immunization. To determine the 24-hour post-challenge immune response, healed, LmCen−/− immunized and age-matched naïve control mice were needle challenged with $10^5$ metacyclic *L. major* wild type (LmWT) parasites in the contralateral ear (at 12 weeks). (FIG. 14A) Representative photographs of ears showing the course of lesion development and subsequent cure from primary LmWT infection in healed group of mice. Ear lesion size was measured weekly for both LmCen−/− immunized (LmCen−/−) and healed from primary infected group (Healed) of mice after intradermal inoculation of parasites. The results are the mean±SEM of 1 ear for 5 mice per group. (FIG. 14B) Gating strategies and multiparameter flow cytometry-based analysis for single, double, or triple cytokine secreting CD4$^+$CD44$^+$ T cells after a 20-hour in vitro re-stimulation with freeze-thaw *L. major* antigen (LmFTAg) from pooled ears of the naïve (no immunization and not challenged), healed, and LmCen−/− immunized groups of mice plus naive splenic APCs. Antigen-experienced cells were gated and divided into six distinct subpopulations, and the percentage of the various subpopulations were calculated. (FIG. 14C) Gating strategies and representative dot plots of an early immune response in the ears of age-matched non-immunized, healed, and LmCen−/− immunized mice following needle challenge with wild type *L. major*-parasites. Naïve mice injected with PBS group are in the control group. Twenty-four hours post-challenge, ear-derived cells were analyzed and represented as the percentage of IFN-γ-producing (i) CD4+ CD44Hi and (ii) CD4+CD44HiT-bet+Ly-6C+−T cells in response to 12-14 hours of in vitro re-stimulation with freeze-thaw *L. major* antigen (LmAg) plus naive splenic APCs. (FIG. 14D) Representative photographs of ear lesions in age-matched non-immunized, healed, and LmCen−/− immunized mice at 5 weeks after LmWT infection sand fly challenge. Only the age-matched, non-immunized group developed lesions (arrow) at 5 weeks post-challenge compared with healed and LmCen−/− immunized mice. Positivity for each antibody against intracellular cytokines was determined using fluorescence minus one (FMO) controls.

FIGS. 15A-15C show non-persistence and the nonpathogenic nature of live attenuated LmCen−/− parasites in a hamster model. (FIG. 15A) Schematic representation of experimental plan to determine the persistence of LmCen−/− parasites following intradermal immunization (ID). Lesion size was monitored in hamsters infected with $10^6$ total stationary phase of either LmWT or LmCen−/− parasites. Infected hamsters were sacrificed at the indicated days post-inoculation and parasite burden was determined at inoculation site (ear) and draining lymph node (dLN) by limiting dilution assay. (FIG. 15B) Representative photographs of ears of LmWT and LmCen−/− infected hamsters at 3, 15, 28, and 49 days post infection. Arrows indicate lesion development. (FIG. 15C) Ear lesion diameters were measured at the indicated days post-infection. Results are mean±SEM, 1 ear, total 6-15 hamsters per group. Open circle represents LmWT infected group and open square represents LmCen−/− immunized group) with total 6-15 hamsters per group. Statistical analysis was performed by Mann Whitney two-tailed test (Mean and SD of each group are shown; nsp-0.9, p<0.002, **p<0.0001).

(FIG. 16A) Schematic representation of experimental plan to determine the cross-protective efficacy of LmCen−/− parasites against an *L. donovani* infected sand fly (*Lutzomyia longipalpis*) challenge. Hamsters were immunized by intradermal injection in the left ear dermis with $1 \times 10^6$ stationary phase centrin-deleted *L. major* (LmCen−/−) promastigotes. Seven weeks post-immunization, both immunized and age matched non-immunized animals were challenged with thirty *L. donovani* infected sand flies in the right ear and subsequently analyzed at the indicated time points. (FIG. 16B) Kaplan-Meier survival curves of LmCen–/–-immunized hamsters following challenge with *L. donovani* (immunized, n=8) infected sand flies and compared with age-matched non-immunized challenged group (non-immunized, n=8). (FIG. 16C) Photo showing the clinicopathologic features of visceral leishmaniasis (VL) in a representative sick age-matched non-immunized hamster (Non-Imm Chal), compared with LmCen–/– immunized healthy hamsters (Imm Chal) after 9 months of sand fly-transmitted *L. donovani* challenge. (FIG. 16D) Photograph of two representative spleen samples for both LmCen–/– immunized and non-immunized challenged hamsters (n=10/group), as well as a naïve hamster (one spleen sample). The spleen size of all the hamsters was measured in centimeters.

FIGS. 18A-18D show whole genome sequencing and assembly of serum free LmCen–/– parasites. Complete genome sequencing of two strains of LmCen–/– (grown in media with or without fetal bovine serum) was performed using MiSeq genome sequencing reactions on an Illumina sequencing instrument. LmCen–/– sequence reads were aligned against a *Leishmania major* Friedlin strain reference genome (retrieved from tritrypdb.org) using HIVE-hexagon tools. Based on a haploid genome length of 32,000,000 bp, a read length of 150, a coverage of ≥148 was obtained [C=LN/G. C=coverage G=haploid genome length L=read length N=number of reads]. The sequence reads in each panel (nodes 3, 4, 35, and 41) are indicated as count forward and count reverse. The analysis of the whole genome sequence data is available (see hive.biochemistry.gwu.edu/review/Leishmania_publication/Spades_NIH_serum_free). Distribution of SNPs in the genome of LmCen–/– parasites grown in serum free conditions was compared to LmCen–/– with serum. (FIGS. 18A-18B) Four random contigs (nodes) out of 927 contigs constructed using Illumina sequence reads. (FIG. 18C) Table showing comparable scaffolds and no large-scale rearrangements between LmCen$^{-/-}$ parasites grown in media containing serum or serum free media. (FIG. 18D) Synteny graph showing similarity between LmCen$^{-/-}$ parasites grown in media containing serum and serum free media across their entire genomes.

FIG. 19 shows an immune response comparison. LmCen–/– grown in serum free medium are as immunogenic as LmCen–/– grown in serum containing medium. Gene expression in spleen cells with 24 hours of *L. major* freeze thaw antigen (FTAg) re-stimulation is shown; +FTAg of lab grown and GLP grade LmCen–/– (right side) parasite (stationary phase total $10^6$ parasites) immunized hamsters at 6 weeks post ID immunization were used. For gene expression, 2-ΔΔCT method was employed to determine the fold expression of each gene (normalized against γ-actin expression), and the data are plotted as fold change over naive hamsters. The results are representative of one independent experiment with 3 hamsters per group. The mean with SEM of each group is shown.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Jun. 3, 2022, 8.55 KB, which is incorporated by reference herein. In the accompanying sequence listing:

SEQ ID NO: 1 is an exemplary guide RNA.

SEQ ID NO: 2 is an exemplary guide RNA.

SEQ ID NO: 3 is an exemplary donor DNA.

SEQ ID NO: 4 is an exemplary *Leishmania major* centrin gene (LmjF.07.0710).

SEQ ID NO: 5 is an exemplary *Leishmania major* centrin protein.

SEQ ID NO: 6 is a *Leishmania major* centrin gene-specific forward primer.

SEQ ID NO: 7 is a *Leishmania major* centrin gene-specific reverse primer.

SEQ ID NO: 8 is a gRNAa targeting site in a *Leishmania major* centrin gene.

SEQ ID NO: 9 is a gRNAb targeting site in a *Leishmania major* centrin gene.

Figures 1A, 1B, 1C, 1D:
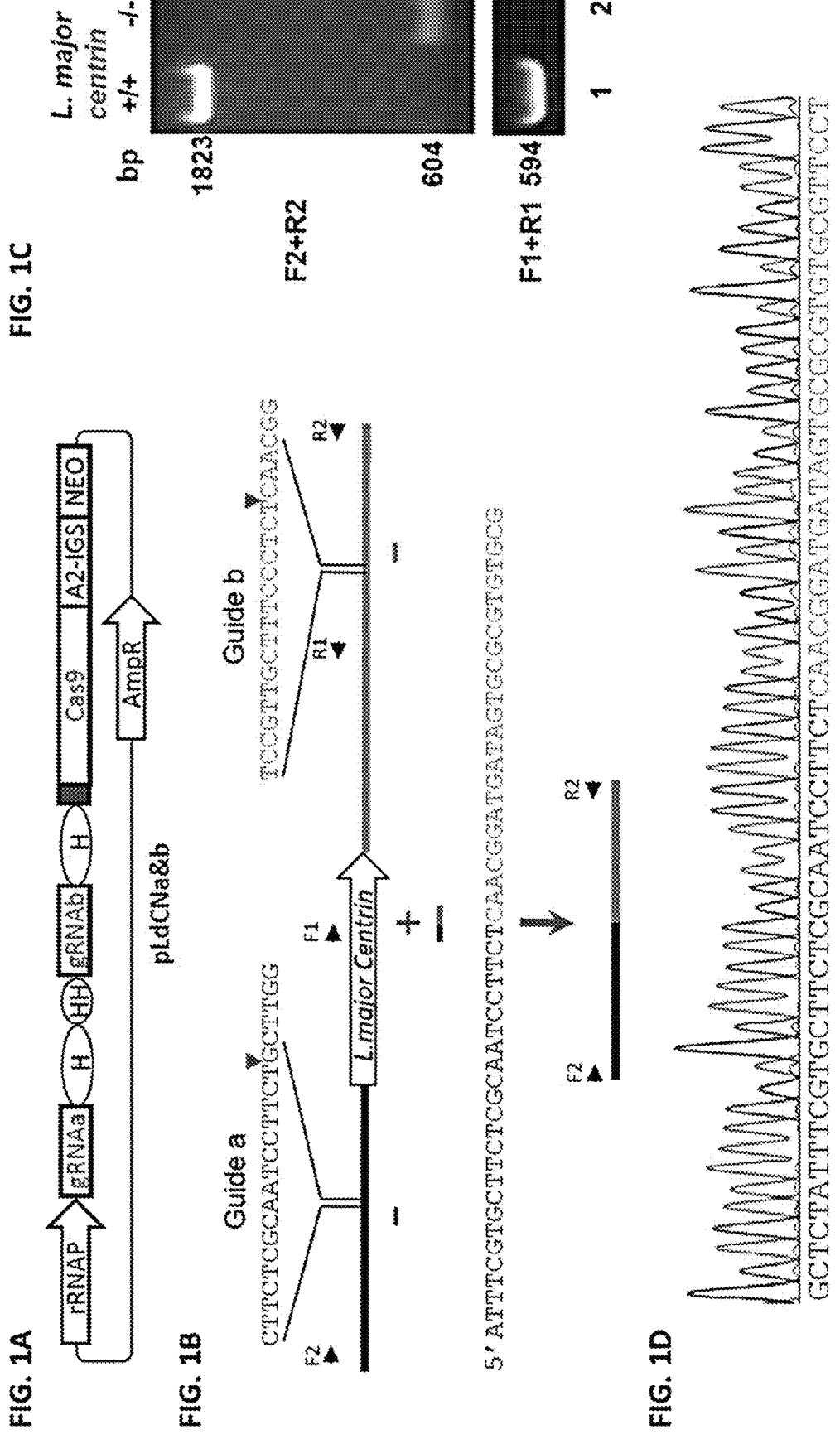

SEQ ID NO: 10 is a synthetic oligonucleotide (see FIG. 1D).

SEQ ID NO: 11 is an exemplary guide RNA.

SEQ ID NO: 12 is an exemplary guide RNA.

SEQ ID NO: 13 is an isotype control tetramer 1-A(b) human CLIP 87-101.

Figures 9A, 9B:
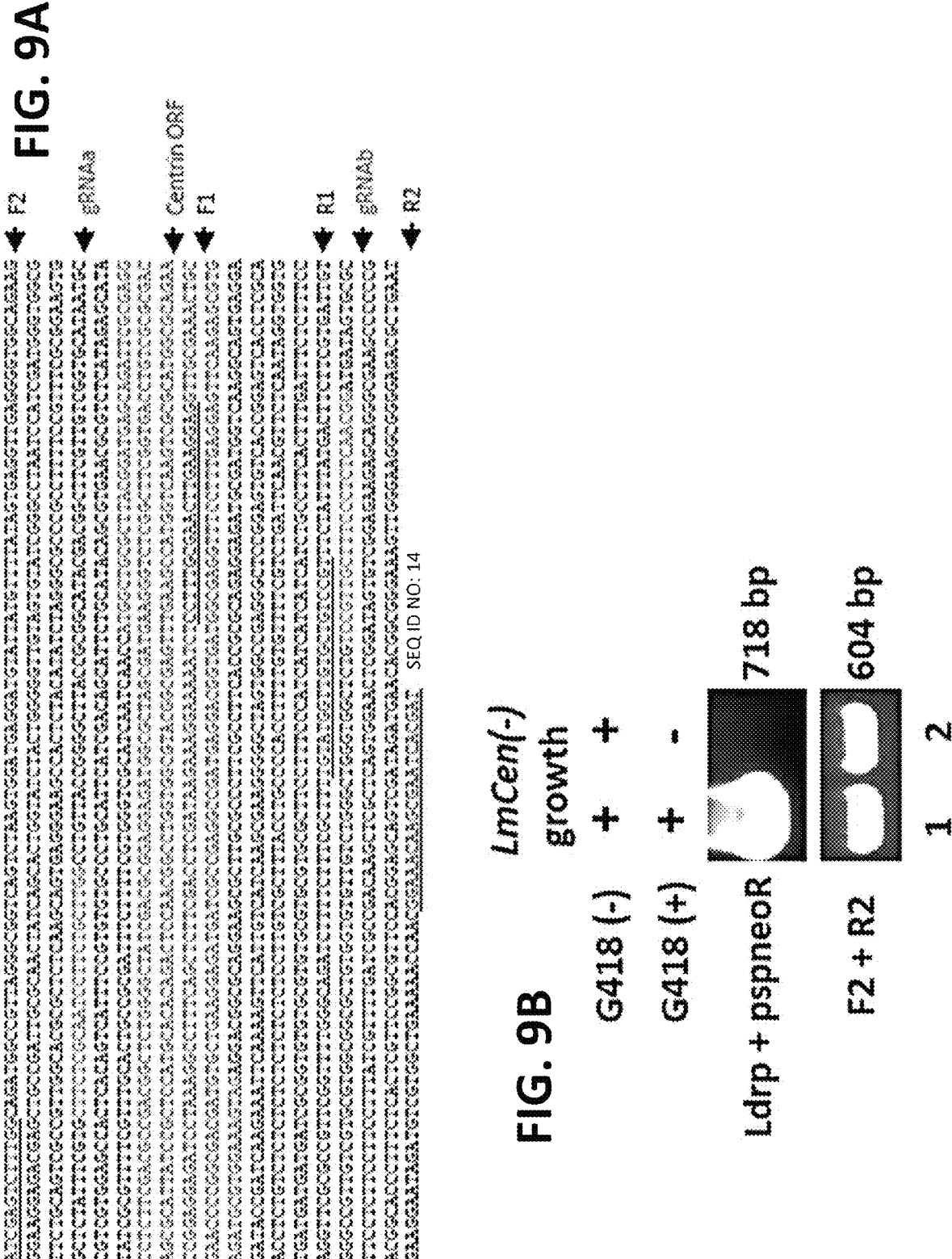
FIGS. 9A-9D show *Leishmania major* gene editing and growth.

SEQ ID NO: 14 is a *Leishmania major* centrin gene (LmjF.22.1410) and its flanking sequences (see FIG. 9A).

SEQ ID NO: 15 is the 2W1S peptide.

SEQ ID NO: 16 is an exemplary *Leishmania major* centrin gene (LmjF.22.1410).

DETAILED DESCRIPTION

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising an immunogenic composition" includes single or plural immunogenic compositions and is considered equivalent to the phrase "comprising at least one immunogenic composition." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. Dates of GenBank® Accession Nos. and TriTrypDB Transcript ID Nos. referred to herein are the sequences available on Dec. 17, 2019. All references, including journal articles, patents, and patent publications, and GenBank® Accession numbers cited herein are incorporated by reference in their entirety.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

In order to facilitate review of the various embodiments of the disclosure, the following explanations of specific terms are provided.

Adjuvant: A substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules. Exemplary biological adjuvants include IL-2, RANTES, GM-CSF, TNF-α, IFN-γ, G-CSF, LFA-3, CD72, B7-1, B7-2, OX-40L and 41 BBL.

Administer: As used herein, administering a composition to a subject means to give, apply, or bring the composition into contact with the subject, such as a composition that includes a live, attenuated, modified *Leishmania* provided herein. Administration can be local or systemic. Administration can be accomplished by any of a number of routes, such as, for example, oral, injection (such as subcutaneous, intramuscular, intradermal, intraperitoneal, intravenous, intrathecal and intradermal), sublingual, rectal, transdermal (for example, topical), intranasal, vaginal, and inhalation routes.

Antigen (Ag): A compound, composition, or substance that can stimulate the production of antibodies or a T cell response in an animal, including compositions (such as one that includes a modified *Leishmania* species or molecules therefrom, such as proteins, peptides, or nucleic acids) that are administered to an animal. Examples of antigens include, but are not limited to, peptides, lipids, polysaccharides, and nucleic acids containing antigenic determinants, such as those recognized by an immune cell.

An antigen reacts with the products of specific humoral or cellular immunity, including those induced by heterologous antigens, such as the disclosed antigens. "Epitope" or "antigenic determinant" refers to the region of an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and nuclear magnetic resonance.

Biopterin transporter 1 (Bt1): Biopterin transporter 1 aids in growth of *Leishmania* through transporting biopterin and folate. A variety of Bt1 molecules are included, such as various Bt1 nucleic acids and proteins. Biopterin transporter 1 sequences are publicly available. For example, TriTrypDB Transcript ID Nos. LmjF.35.5150, LbrM.34.5090, and LmxM.31.3720.1 disclose nucleic acid and protein sequences for Bt1 found in *Leishmania major, L. braziliensis,* and *L. mexicana,* respectively, incorporated by reference herein in their entireties. Additional Bt1 nucleic acid and protein sequences can be identified, including Bt1 variants that retain Bt1 biological activity (such as transport of biopterin and folate). Thus, a functionally deleted or genetically inactivated Bt1 includes those that cannot transport of biopterin and folate, and results in an amastigote growth-arrested modified *Leishmania.*

Cell culture: Cells grown under controlled conditions. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Centrin: Also known as caltractin, centrin is a calcium binding phosphoprotein in the EF-hand superfamily. Centrin is essential in the duplication of centrosomes in eukaryotes, including *Leishmania.* A variety of centrin molecules are included, such as various centrin nucleic acids and proteins. Centrin sequences are publicly available. For example, TriTrypDB Transcript ID Nos. LmjF.07.0710, LBRM2903_070014900, and LmxM.07.0710 disclose nucleic acid and protein sequences for centrin found in *Leishmania major, L. braziliensis,* and *L. mexicana,* respectively, incorporated by reference herein in their entireties. Additional centrin nucleic acid and protein sequences, including centrin variants that retain centrin biological activity (such as duplication of centrosomes), can be identified using known methods. Thus, a functionally deleted or genetically inactivated centrin includes those that cannot duplicate centrosomes, and results in an amastigote growth-arrested modified *Leishmania.*

Complementary: Ability to form base pairs between nucleic acids. Oligonucleotides and their analogs hybridize by hydrogen bonding, which includes Watson-Crick, Hoogsteen or reversed Hoogsteen hydrogen bonding, between complementary bases. Generally, nucleic acid molecules consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acids or two distinct regions of the same nucleic acid.

"Specifically hybridizable" and "specifically complementary" are terms that indicate a sufficient degree of complementarity such that stable and specific binding occurs between the probe (or its analog) and the nucleic acid target (e.g., DNA or RNA). The probe or analog may, but need not have, 100% complementarity to its target sequence to be specifically hybridizable. A probe or analog is specifically hybridizable when there is a sufficient degree of complementarity to avoid non-specific binding of the probe or analog to non-target sequences under conditions where specific binding is desired, for example in the methods disclosed herein. Such binding is referred to as specific hybridization.

Contact: Placement in direct physical association; includes both in solid and liquid form.

Double-strand breaks (in DNA): Breaks in which both strands of the double helix are severed. Three mechanisms are available for repair of double-strand breaks: non-homologous end joining (NHEJ), microhomology-mediated end joining (MMEJ), and homologous recombination (HR, an example of homology-directed repair).

Expression: The process by which the coded information of a gene is converted into an operational, non-operational, or structural part of a cell, such as the synthesis of a protein. Gene expression can be influenced by external signals. For instance, exposure of a cell to a hormone may stimulate expression of a hormone-induced gene. Different types of cells can respond differently to an identical signal. Expression of a gene also can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced. In an example, the disclosed *Leishmania* having a reduced or eliminated expression of centrin, kharon1, biopterin transporter 1 (Bt1), p27, Lipophosphoglycan biosynthetic protein 2 (Lpg-2), ubiquitin fold modifier-1 (Ufm-1), and/or Ufm1 processing peptidase (Ufsp) gene, and in some examples also a serum-free growth modification, can be used to treat or prevent leishmaniasis in a subject.

The expression of a nucleic acid molecule can be altered relative to a normal (wild type) nucleic acid molecule. Alterations in gene expression, such as differential expression, include but are not limited to: (1) overexpression; (2) underexpression; or (3) suppression of expression. Alternations in the expression of a nucleic acid molecule can be associated with, and in fact cause, a change in expression of the corresponding protein.

Genetic inactivation: When used in reference to the expression of a nucleic acid molecule, such as a gene, refers to any process which results in a decrease in production of a gene product (or even elimination of production of a gene product). A gene product can be RNA (such as mRNA, rRNA, tRNA, and structural RNA) or protein, such as a centrin, kharon1, biopterin transporter 1 (Bt1), p27, Lipophosphoglycan biosynthetic protein 2 (Lpg-2), ubiquitin fold modifier-1 (Ufm-1), and/or Ufm1 processing peptidase (Ufsp) protein. Therefore, gene inactivation includes processes that decrease transcription of a gene or translation of mRNA, such as a decrease of at least 20%, at least 30%, at least 40%, at least 50%, at least 60%, at least 75%, at least 80%, at least 90%, at least 95%, at least 98%, at least 99%, or even 100%.

For example, a mutation, such as a substitution, partial or complete deletion, insertion, or other variation, or combinations thereof, can be made to a gene sequence that significantly reduces (and in some cases eliminates) production of the gene product or renders the gene product substantially or completely non-functional. For example, a genetic inactivation of a centrin, kharon1, biopterin transporter 1 (Bt1), p27, Lipophosphoglycan biosynthetic protein 2 (Lpg-2), ubiquitin fold modifier-1 (Ufm-1), and/or Ufm1 processing peptidase (Ufsp) gene in *Leishmania*, results in

*Leishmania* having a non-functional or non-existent centrin, kharon1, biopterin transporter 1 (Bt1), p27, Lipophosphoglycan biosynthetic protein 2 (Lpg-2), ubiquitin fold modifier-1 (Ufm-1), and/or Ufm1 processing peptidase (Ufsp) protein, respectively, which results in a live, attenuated *Leishmania* that can be used to treat or prevent leishmaniasis. Genetic inactivation is also referred to herein as "functional deletion".

Gene-editing complex: Gene-editing complex refers to those gene-editing complexes that do not occur in nature (or non-naturally occurring gene-editing complexes). In example embodiments, the gene-editing complexes include CRISPR-Cas gene-editing complexes, TALEN gene-editing complexes, and Zinc finger nuclease (ZFN) gene-editing complexes. In specific, non-limiting examples, the gene-editing complex is a CRISPR-Cas9 gene-editing complex.

Guide sequence: As used herein, the term "guide sequence" refers to an RNA sequence that is part of the CRISPR complex and recognizes a target nucleic acid sequence. In example embodiments, the guide sequences are presented as DNA sequences which encode for the RNA sequences. In some embodiments, target recognition can occur through non-covalent interactions, including hydrogen bonding, recognition of a structural motif, nucleic acid sequence recognition, base pairing, the like, or any combination thereof. In other embodiments, target recognition can occur via covalent interactions. Exemplary target nucleic acid sequences include centrin, kharon1, biopterin transporter 1 (Bt1), p27, Lipophosphoglycan biosynthetic protein 2 (Lpg-2), ubiquitin fold modifier-1 (Ufm-1), and/or Ufm1 processing peptidase (Ufsp).

Homology-directed repair (HR): A mechanism in cells to repair double-stranded DNA lesions. The most common form of HR is homologous recombination (HDR). The HDR repair mechanism can only be used by the cell when there is a homologous piece of DNA present in the nucleus that serves as the repair template and occurs mostly in G2 and S phase of the cell cycle. In some embodiments, HR is used with CRISPR/Cas gene-editing, for example, to reduce off-target effects.

Host: A cell or organism which harbors another organism or biological entity, usually a parasite (such as a malaria parasite). In one example, a host is a human or non-human primate that can be or is infected by a *Leishmania* species (such as *L. infantum, L. aethiopica, L. amazonensis, L. Arabica, L. archibaldi, L. aristedesi, L. braziliensis, L. chagasi, L. colombiensis, L. deanei, L. donovani, L. enriettii, L. equatorensis, L. forattinii, L. garnhami, L. gerbil, L. guyanensis, L. herreri, L. hertigi, L. killicki, L. lainsoni, L. major, L. Mexicana, L. naiffi, L. panamensis, L. peruviana, L. pifanoi, L. shawi, L. tarentolae, L. tropica, L. turanica*, or *L. venezuelensis*). The term "host" is used interchangeably with the term "subject" herein.

Hybridize: A process where single-strand DNA or RNA molecules anneal to complementary DNA or RNA. Changing physiological conditions, for example by raising the surrounding temperature, can cause multi-strand nucleic acids to separate into single strands. These strands are complementary to each other but may also be complementary to other sequences present in their surroundings. Lowering the surrounding temperature allows the single-strand molecules to anneal or hybridize to each other.

Increase or Decrease: A statistically significant positive or negative change, respectively, in quantity from a control value (such as a value before treatment with the disclosed methods). An increase is a positive change, such as an increase at least 50%, at least 100%, at least 200%, at least 300%, at least 400% or at least 500% as compared to the control value. A decrease is a negative change, such as a decrease of at least 20%, at least 25%, at least 50%, at least 75%, at least 80%, at least 90%, at least 95%, at least 98%, at least 99%, or at least 100% decrease as compared to a control value. In some examples the decrease is less than 100%, such as a decrease of no more than 90%, no more than 95% or no more than 99%.

Inhibiting or treating a disease: Inhibiting the full development of a disease or condition, for example, in a subject who is at risk for a disease, such as leishmaniasis. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component (such as a nucleic acid, protein, or organelle) has been substantially separated or purified away from other biological components in the cell of the organism in which the component naturally occurs, for instance, other chromosomal and extrachromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis. When referring to organisms, such as *Leishmania*, refers to organisms that are substantially removed from other organisms, such as a host or host cells.

Kharon1: Kharon1 is a flagellum targeting protein found in Trypanosomes, such as *Leishmania* species. Kharon1 is involved in trafficking flagellar membrane proteins and cell division. A variety of kharon1 molecules are included, such as various kharon1 nucleic acids and proteins. Kharon1 sequences are publicly available. For example, TriTrypDB Transcript ID Nos. LmxM.36.5850.1, LINF_360068400-T1, and MHOM/BR/75/M2903 disclose nucleic acid and protein sequences for kharon1 found in *Leishmania mexicana, L. infantum*, and *L. braziliensis*, respectively, incorporated by reference herein in their entireties. Additional kharon1 nucleic acid and protein sequences, including kharon1 variants that retain kharon1 biological activity (such as flagella trafficking), can be identified using known methods. Thus, a functionally deleted or genetically inactivated kharon1 includes those that cannot affect flagella trafficking, and results in an amastigote growth-arrested modified *Leishmania*.

Leishmaniasis: A parasitic disease that is found in parts of the tropics, subtropics, and southern Europe. It is classified as a neglected tropical disease (NTD). Leishmaniasis is caused by infection with *Leishmania* parasites, which are spread by the bite of phlebotomine sand flies. The disease can present in three main ways: cutaneous, mucocutaneous, or visceral. The cutaneous form presents with skin ulcers, while the mucocutaneous form presents with ulcers of the skin, mouth, and nose, and the visceral form starts with skin ulcers and then later presents with fever, low red blood cells, and enlarged spleen and liver. Symptoms can include one or more of ulceration/lesions on the skin, weight loss, weakness, fever that lasts for weeks or months, enlarged spleen, enlarged liver, decreased production of blood cells, bleeding, and other infections.

Lipophosphoglycan biosynthetic protein 2 (Lpg2): Lpg2 aids in the *Leishmania* infection cycle through synthesizing a major lipophosphoglycan involved in host infectivity. A variety of Lpg2 molecules are included, such as various Lpg2 nucleic acids and proteins. Lpg2 sequences are publicly available. For example, TriTrypDB Transcript ID Nos. LmjF.34.3120, LbrM.20.2700, and LmxM.33.312 disclose nucleic acid and protein sequences for Lpg2 found in *Leishmania major, L. braziliensis*, and *L. mexicana*, respectively, incorporated by reference herein in their entireties. Additional Lpg2 nucleic acid and protein sequences, including Lpg2 variants that retain Lpg2 biological activity (such as synthesizing lipophosphoglycan), can be identified using known methods. Thus, a functionally deleted or genetically inactivated Lpg2 includes those that cannot synthesize lipophosphoglycan, and results in an amastigote growth-arrested modified *Leishmania*.

Mammal: This term includes both human and non-human mammals. Similarly, the term "subject" includes both human and veterinary subjects.

Modification: A change in the sequence of a nucleic acid or protein molecule. For example, amino acid or nucleic acid sequence modifications include mutations thereof, for example, substitutions, insertions, and deletions, or combinations thereof. Insertions include 3' or 5' end fusions or amino and/or carboxyl terminal fusions as well as intrasequence insertions of single or multiple amino acid residues or nucleotides. Deletions are characterized by the removal of one or more amino acid residues from a protein sequence or nucleotides from a nucleic acid sequence. In some embodiments herein, the modification (such as a substitution, insertion, or deletion) results in a change in function, such as a reduction or enhancement of a particular activity of a protein (such as an amastigote growth-arresting modification or a serum-free growth modification). Substitutional modifications are those in which at least one residue or nucleotide has been removed and a different residue or nucleotide inserted in its place. Substitutions, deletions, insertions, or any combination thereof may be combined to arrive at a final mutant sequence. Amino acid modifications can be prepared by modification of nucleotides in the DNA encoding the protein, thereby producing DNA encoding the modification. In particular examples, the presence of one or more modifications in a gene can significantly inactivate that gene. Molecular biology and recombinant techniques for making insertion, deletion, and substitution mutations at predetermined sites in DNA having a known sequence are known. A "modified" protein, nucleic acid, or organism (such as a *Leishmania* species) is one that has one or more modifications as outlined above.

p27: Also known as Ldp27, p27 is a protein involved in maintaining *Leishmania* within its host. p27 forms part of the cytochrome c oxidase (COX) complex and aids in oxidative phosphorylation in amastigotes. A variety of p27 molecules are included, such as various p27 nucleic acids and proteins. p27 sequences are publicly available. For example, TriTrypDB Transcript ID Nos. LmjF.28.0980: mRNA, LBRM2903_280016100.1, and LAEL147_000491900.1 disclose nucleic acid and protein sequences for p27 found in *Leishmania major, L. braziliensis*, and *L. aethiopica*, respectively, incorporated by reference herein in their entireties. Additional p27 nucleic acid and protein sequences, including p27 variants that retain p27 biological activity (such as oxidative phosphorylation in amastigotes), can be identified using known methods. Thus, a functionally deleted or genetically inactivated Lpg2 includes those that cannot affect s oxidative phosphorylation, and results in an amastigote growth-arrested modified *Leishmania*.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids, such as water, physiological saline, balanced salt solutions, aqueous dextrose, glycerol, or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example, sodium acetate or sorbitan monolaurate.

Protospacer-adjacent motif (PAM): A short sequence motif immediately adjacent to the target of a CRISPR complex. PAMs are different in different organisms and PAM recognition is promiscuous in some systems.

Recombinant: A recombinant nucleic acid, protein or organism (such as a *Leishmania*) is one that has a sequence (such as a gene or genome sequence of a *Leishmania*) that is not naturally occurring (e.g., having a gene deletion or insertion) or has a sequence that is made by an artificial combination of two otherwise separated segments of sequence. The term recombinant includes nucleic acids, proteins and organisms that have been altered by addition, substitution, or deletion of a portion of a natural nucleic acid molecule (such as a gene) or protein.

Ribonucleoprotein complex: As used herein, a "ribonucleoprotein complex" refers to a complex of protein and RNA. Examples of ribonucleoprotein (RNP) complexes include the ribosome, the enzyme telomerase, RNAse P, and small nuclear RNPs. In a specific embodiment, the ribonucleoprotein complex is CRISPR-Cas, CRISPR-Cascade, CRISPR-Csy, or any CRISPR-RNA-guided complex.

Single-stranded nucleic acid: A nucleic acid that only includes a single polymer strand (i.e., the nucleic acid polymer strand does not form non-covalent bonds with another nucleic acid polymer), such as single-stranded DNA (ssDNA). The nucleic acid molecule can be single-stranded in full (e.g., ssDNA formed through melting a double-stranded DNA molecule) or in part (e.g., a ssDNA region formed through damage and/or enzymatic activity). In example embodiments, an ssDNA can be a donor DNA.

Specific binding: Binding of an agent substantially or preferentially only to a defined target such as a defined oligonucleotide, DNA, RNA, or portion thereof. Thus, a nucleic acid-specific binding agent binds substantially only to a defined nucleic acid, (such as a target sequence in a target nucleic acid) and does not substantially bind to any other nucleic acid. In some examples, specific binding includes the hybridization of one nucleic acid molecule to another. For example, a nucleic acid molecule specifically binds another nucleic acid molecule if a sufficient amount of the nucleic acid molecule forms base pairs or is hybridized to its target nucleic acid molecule to permit detection of that binding (such as at least 90%, 91%, 92%, 93%, 94%, 95%, 96%, 97%, 98%, 99%, or 100% complementary).

Subject: As used herein, the term "subject" refers to a mammal and includes, without limitation, humans, domestic animals (e.g., dogs or cats), farm animals (e.g., cows, horses, or pigs), non-human primates, and laboratory animals (mice, rats, hamsters, guinea pigs, pigs, rabbits, dogs, or monkeys).

Subunit: As used herein, a "subunit" refers to a single protein molecule that assembles or coassembles with other protein or RNA molecules to form a protein or ribonucleoprotein (RNP) complex. Some naturally occurring proteins have a relatively small number of subunits and are therefore described as oligomeric, for example hemoglobin or DNA polymerase. Others may consist of a very large number of subunits and are therefore described as multimeric, for example microtubules and other cytoskeleton proteins. The subunits of a multimeric protein may be identical, homologous or totally dissimilar. For example, the CRISPR-Cascade or -Csy (such as CRISPR-Cas9) ribonucleoprotein complex includes multiple subunits, which assemble around a RNA.

Therapeutically effective amount (or effective amount): A quantity of a specific substance, such as a live, attenuated *Leishmania* species (or immunogenic composition, vaccine, or pharmaceutical composition thereof), sufficient to achieve a desired effect in a subject being treated (such as treating leishmaniasis). When administered to a subject, a dosage will generally be used that will achieve target tissue concentrations that has been shown to achieve a desired in vitro effect.

Ubiquitin fold modifier 1 (Ufm1): Also known as Ubm1, Ufm1 is a ubiquitin-like protein involved in parasite virulence and amastigote survival. A variety of Ufm1 molecules are included, such as various Ufm1 nucleic acids and proteins. Ufm1 sequences are publicly available. For example, TriTrypDB Transcript ID Nos. LmjF.16.1065, LbrM.16.1090, and LmxM.16.1065 disclose nucleic acid and protein sequences for Ufm1 found in *Leishmania major, L. braziliensis*, and *L. aethiopica*, respectively, incorporated by reference herein in their entireties. Additional Ufm1 nucleic acid and protein sequences, including Ufm1 variants that retain Ufm1 biological activity (such as ubiquitin-like activity), can be identified using known methods. Thus, a functionally deleted or genetically inactivated Ufm1 includes those that do not have ubiquitin-like activity, and results in an amastigote growth-arrested modified *Leishmania*.

Ufm1 processing peptidase (Ufsp): Ufsps are Ufm1-specific proteases involved in processing ubiquitin-like modifiers for activation. Amastigotes in Ufsps-null *Leishmania* show growth defects. A variety of Ufsp molecules are included, such as various Ufsp nucleic acids and proteins. Ufsp sequences are publicly available. For example, Gannavaram et al. disclose sequences from multiple species, including *Leishmania* (*PLoS Negl Trop Dis.*, 8(2): e2707, 2014, incorporated by reference herein in its entirety). Additional Ufsp nucleic acid and protein sequences, including Ufsp variants that retain Ufsp biological activity (such as Ufm1-specific proteolytic activity), can be identified using known methods. Thus, a functionally deleted or genetically inactivated Ufsp includes those that do not have Ufm1-specific proteolytic activity, and results in an amastigote growth-arrested modified *Leishmania*.

Vector: A nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like. A vector can be a viral vector. In another example a vector is a plasmid.

Vaccine: Composition that when administered to a subject, induces a decrease of the severity of the symptoms of a disorder or disease. In one embodiment, a vaccine decreases the severity of the symptoms of leishmaniasis and/or decreases the parasitic load.

Wild-type: The genotype or phenotype that is most prevalent in nature. The naturally occurring, non-mutated (or non-modified) version of a nucleic acid sequence. Among multiple alleles, the allele with the greatest frequency within the population is usually the wild-type. The term "native" can be used as a synonym for "wild-type."

Overview

Leishmaniasis is a debilitating and often fatal neglected tropical disease caused by *Leishmania* protozoa transmitted by infected sand flies. Vaccination through leishmanization with a live, attenuated vaccine (for example, using *Leishmania major*) has been used with efficacy, but it is no longer used because it produces skin lesions. A new type of leishmanization is described herein using a CRISPR genome-edited *Leishmania* cutaneous species (for example, *L. major*).

Disclosed herein are live, attenuated *Leishmania* species having at least one modification. In some embodiments, the *Leishmania* species is a cutaneous or mucocutaneous *Leishmania* species; and the at least one modification is an amastigote growth-arresting modification. In some examples, the *Leishmania* species includes one or more additional modifications, such as a serum-free growth modification. In some examples, the *Leishmania* species does not include an antibiotic-resistance gene.

In other embodiments, the live, attenuated *Leishmania* species do not include an antibiotic-resistance gene, and the at least one modification is an amastigote growth-arresting modification, a serum-free growth modification, or both.

The live, attenuated *Leishmania* species can include a variety of modified *Leishmania* species, such as modified mucocutaneous *Leishmania* (for example, *L. braziliensis*), or modified cutaneous *Leishmania* (for example, *L. major, L. tropica*, or *L. panamensis*). A variety of modifications can be included, such as mutations (for example, gene deletions). Various genes can be modified, for example genetically inactivated, such as genes involved in growth, for example, the centrin, kharon1, biopterin transporter 1 (Bt1), p27, lipophosphoglycan biosynthetic protein 2 (Lpg-2), ubiquitin fold modifier-1 (Ufm-1), or Ufm1 processing peptidase (Ufsp) gene. In specific, non-limiting examples, the modification can include a modification (such as a functional or genetic deletion) that results in amastigote growth arrest of the *Leishmania* (for example, deletion of the centrin gene). In specific, non-limiting examples, the live, attenuated *Leishmania* species can be modified *L. major*. For example, the modified *L. major* can include at least one modification in which the at least one modification includes a centrin gene deletion and an amastigote growth-arresting modification, and the *L. major* does not include an antibiotic-resistance gene.

In addition, disclosed herein are immunogenic compositions that include any of the live, attenuated *Leishmania* species disclosed herein (such as a composition that includes an adjuvant, a composition that is not contaminated by a transmissible spongiform encephalopathy (TSE) agent, or both). Vaccines are also disclosed herein that include any of the live, attenuated *Leishmania* species or immunogenic compositions disclosed herein. Also disclosed are pharmaceutical compositions that include any of the live, attenuated *Leishmania* species, immunogenic compositions, or vaccines disclosed herein.

Disclosed herein are methods of treating subjects for leishmaniasis. In some embodiments, the methods include administering any of the live, attenuated *Leishmania*, immunogenic compositions, vaccines, or pharmaceutical compositions disclosed herein. For example, the leishmaniasis can be visceral, cutaneous, or mucocutaneous leishmaniasis (such as leishmaniasis caused by *L. infantum, L. aethiopica, L. amazonensis, L. Arabica, L. archibaldi, L. aristedesi, L. braziliensis, L. chagasi, L. colombiensis, L. deanei, L. donovani, L. enriettii, L. equatorensis, L. forattinii, L. garnhami, L. gerbil, L. guyanensis, L. herreri, L. hertigi, L. killicki, L. lainsoni, L. major, L. Mexicana, L. naiffi, L. panamensis, L. peruviana, L. pifanoi, L. shawi, L. tarentolae, L. tropica, L. turanica*, or *L. venezuelensis*). In specific, non-limiting examples, the leishmaniasis is visceral leishmaniasis (such as leishmaniasis is caused by *L. donovani, L. infantum*, or *L. chagasi*). In specific, non-limiting examples, the leishmaniasis is cutaneous leishmaniasis (such as leishmaniasis caused by *L. major, L. mexicana, L. tropica, L. aethiopica, L. amazonensis, L. braziliensis, L. infantum*, or *L. panamensis*). In specific, non-limiting examples, the leishmaniasis is mucocutaneous leishmaniasis (such as leishmaniasis caused by *L. amazonensis* or *L. braziliensis*). In some embodiments, leishmaniasis is caused by *Leishmania major, L. donovani*, or *L. mexicana*, and administering any of the live, attenuated *Leishmania* species, immunogenic compositions, vaccines, or pharmaceutical compositions disclosed herein includes administration of a live modified *L. major*. In some examples, the at least one modification of the *L. major* includes a centrin gene deletion and a serum-free growth modification. In specific examples, the modified *L. major* does not include an antibiotic-resistance gene.

In some examples, the methods further include selecting a subject in need of a treatment for leishmaniasis.

Further disclosed herein are methods of producing an immunogenic composition. In some embodiments, the methods include introducing a first nucleic acid encoding a selection marker (such as an antibiotic resistance gene) and gene-editing complex into *Leishmania* promastigotes, selecting *Leishmania* promastigotes with the selection marker, culturing the *Leishmania* promastigotes with the selection marker, selecting *Leishmania* promastigotes with a slow-growing phenotype, and optionally culturing the *Leishmania* promastigotes with the slow-growing phenotype in serum-free media (for example, by culturing the *Leishmania* promastigotes in serially diluted media, wherein the final dilution comprises 0% serum). A variety of additional steps can optionally be included, such as introducing a second nucleic acid after *Leishmania* promastigotes with the selection marker are selected, wherein the second nucleic acid facilitates gene editing (such as single or double-strand nucleic acid, for example, a donor nucleic acid to facilitate gene editing). In example embodiments, the gene-editing complex comprises CRISPR/CAS9, such as including at least one guide RNA. In some examples, at least 1, at least 2, at least 4, at least 8, at least 12, at least 16, or at least 20, or about 1-2, 1-4, 2-4, 2-6, 2-8, or 2-20, or about 2 guide RNAs can be used.

In example embodiments, at least one guide RNA binds the nucleic acid flanking an amastigote growth-related gene, such as a centrin, kharon1, Bt1, p27, Lpg-2, Ufm-1, or Ufsp gene. In specific, non-limiting examples, at least one guide RNA binds the nucleic acid flanking centrin (such as SEQ ID NO: 1 and/or SEQ ID NO: 2). In specific, non-limiting examples, the donor nucleic acid includes a contiguous sequence complementary to the sequences flanking the amastigote growth-related gene (such as SEQ ID NO: 3). Other steps can include culturing single clones of the *Leishmania* promastigotes with the slow-growing phenotype in the presence and/or absence of antibiotic (such as geneticin) and selecting single clones of the *Leishmania* promastigotes that are not resistant to the antibiotic, which can select for promastigotes that have lost the gene editing complex, thereby producing *Leishmania* promastigotes the antibiotic resistance gene removed.

Live Attenuated *Leishmania*

Disclosed herein are live, attenuated modified *Leishmania* species. A variety of *Leishmania* species are included. For enhanced safety of the *Leishmania* species, the species can be one that does not penetrate a host beyond the skin or mucous membrane, such as cutaneous or mucocutaneous *Leishmania* species. Examples of cutaneous *Leishmania* species include *L. major, L. tropica*, and *L. panamensis*. Examples of mucocutaneous *Leishmania* species include *L. braziliensis*. In specific, non-limiting examples, the modified *Leishmania* species is modified *L. major.*

Further, the modified *Leishmania* species can include at least one modification, such as at least one, at least two, at least three, at least four, at least five, at least 10, at least 20, at least 30, at least 50, or at least 100, or about 1-100, 1-2, 1-5, 1-10, 1-25, or 1-50, or 1 or 2 modifications or types of modifications (such as serum-free growth modifications, amastigote growth-arresting modification, or both).

A variety of modifications are possible. For example, the modifications can be mutations, such as additions, substitutions, or deletions. In example embodiments, the mutations can facilitate or accompany serum-free growth of *Leishmania* species (also referred to herein as 'serum-free growth modifications' or 'serum-free growth mutations'). In example embodiments, the mutations result in amastigote growth arrest (also referred to herein as 'amastigote growth-arresting modifications' or 'amastigote growth-arresting growth mutations'). In specific, non-limiting examples, the mutations include both amastigote growth-arresting and serum-free growth mutations.

In example embodiments, the live, attenuated *Leishmania* include at least one amastigote growth-arresting modification. A variety of modifications can arrest amastigote growth in *Leishmania*. For example, various genes involved in amastigote growth can be mutated. In specific, non-limiting examples, the modifications can include deletion (such as a partial deletion or complete deletion) of at least one gene involved in amastigote growth. Examples of genes involved in amastigote growth include the centrin, KHARON1, Bt1, p27, Lpg-2, or Ufm-1 gene. In example embodiments, the modifications include mutation of the centrin gene. In specific, non-limiting examples, the live, attenuated *Leishmania* species includes a deletion of the centrin gene. In specific, non-limiting examples, the live, attenuated *Leishmania* species includes a deletion of the centrin gene in *L. major.* An example of a centrin gene includes:

```
                                (SEQ ID NO: 4; TriTrypDB
                         Transcript ID No. LmjF.07.0710)
ATGAGTATCGCGAGCAACACACCTTTAAGGCCGAGCACCTCCGCATCGAA

CGCGAACACCGAGCTCAGCAAGGATCAGCTGGAGGAAATCCGCGAGGCGT

TCGACTTATTCGACACGGATGGCAGTGGCACGATCGACGTGCGGGAGCTG

CGCGTTGCCATGCGGGCACTCGGCTTCGAGCCTCGTAAGGAGGAGCTTCA

GCAGCTTATCAACAGCGTCACCGGTGGCAGCGGCTACGAAGCAACCACTA

CGCGGCTGCCGAGCGCCGGCAATGTGAACGCGTCCAGCGACGTGATCACC

TTCTCGCAGTTTGTGCAGATTATGAAGCACAAGGTGTCACAACGGGACTC

GCGGGAGGAGATGCTGAAGGCGTTCGTGCTCTTCGACACAGAGGGCACTG

GCAAGATCTCGTTCCAGAACTTGAAGCGAGTGGCGGTGGAGCTTGGCGAG

AACATGACGGACGCCGAGCTGCAGGAGATGATCGACGAGGCGGACCGTGA

CGGGGACGGCGAGGTGAGCGAGGAGGAGTTTCTTCGCTTAATGAAGAAGA

CGTCGCTGTACTAA.
```

An example of a centrin protein includes:

```
                                (SEQ ID NO: 5; TriTrypDB
                         Transcript ID No. LmjF.07.0710)
MSIASNTPLRPSTSASNANTELSKDQLEEIREAFDLFDTDGSGTIDVREL

RVAMRALGFEPRKEELQQLINSVTGGSGYEATTTRLPSAGNVNASSDVIT

FSQFVQIMKHKVSQRDSREEMLKAFVLFDTEGTGKISFQNLKRVAVELGE

NMTDAELQEMIDEADRDGDGEVSEEEFLRLMKKTSLY.
```

In some examples, the live, attenuated *Leishmania* do not include an antibiotic-resistance gene. Any of the live, attenuated *Leishmania* species disclosed herein can be generated that do not include an antibiotic-resistance gene. In example embodiments, a modified *Leishmania* species can be generated that does not include an antibiotic-resistance gene. The ability to generate a modified *Leishmania* species that does not include an antibiotic resistance gene provides additional safety features for the modified species. For example, compositions administered to humans are not considered safe and will not be approved by drug regulatory agencies for human use if an antibiotic resistance gene is included. In example embodiments, the modified *Leishmania* species includes an amastigote growth-arresting modification, a serum-free growth modification, or both, and does not include an antibiotic resistance gene.

Various combinations of live, attenuated *Leishmania* with modifications and/or the absence of an antibiotic resistance gene are possible. In specific, non-limiting examples, the modified *Leishmania* species (such as *L. major, L. tropica, L. panamensis*, or *L. braziliensis*) includes an amastigote growth-arresting modification, but does not include an antibiotic resistance gene. In specific, non-limiting examples, the modified *Leishmania* species such as *L. major, L. tropica, L. panamensis*, or *L. braziliensis*) includes a serum-free growth modification, but does not include an antibiotic resistance gene. In specific, non-limiting examples, the modified *Leishmania* species such as *L. major, L. tropica, L.*

*panamensis*, or *L. braziliensis*) includes an amastigote growth-arresting modification and a serum-free growth modification, but does not include an antibiotic resistance gene.

In specific, non-limiting examples, the live, attenuated *Leishmania* is a modified *L. major*. For example, the modified *L. major* can include at least one serum-free growth modification, at least one amastigote growth-arresting modification, the absence of an antibiotic-resistance gene, or any combination thereof. In further examples, the modified *L. major* includes at least one serum-free growth modification, at least one amastigote growth-arresting modification, and the absence of an antibiotic-resistance gene. In specific, non-limiting examples, the modified *L. major* includes at least one serum-free growth modification, at least a centrin gene deletion, and the absence of an antibiotic-resistance gene.

Methods of Production

Further disclosed herein are methods of producing a live, attenuated modified *Leishmania* species, including immunogenic compositions, vaccines, or pharmaceutical compositions thereof. Various steps can be included in the methods. In example embodiments, the method includes the step of introducing a first nucleic acid encoding a selection marker (such as an antibiotic resistance gene) and gene-editing complex into *Leishmania* promastigotes. A variety of antibiotic resistance genes can be included, such as genes that confer resistance to gentamycin, chlorosulfuran imidazolinones, bialaphos, bromoxynil, kanamycin, neomycin, streptomycin, or related antibiotics, such as geneticin (also known as G418). The method can further include selecting *Leishmania* promastigotes with the selection marker. For example, antibiotics (such as gentamycin, chlorosulfuran imidazolinones, bialaphos, bromoxynil, kanamycin, neomycin, streptomycin, or related antibiotics, such as geneticin) can be used where the selection marker is the respective antibiotic resistance gene. In some examples, the method includes culturing the *Leishmania* promastigotes with the selection marker. The method can then include the step of selecting *Leishmania* promastigotes with a phenotype conferred by the gene-editing complex, such as a slow-growing phenotype. The method can also include the step of culturing the *Leishmania* promastigotes with the phenotype conferred by the gene-editing complex (such as a slow-growing phenotype) in serum-free media (for example, by culturing the *Leishmania* promastigotes in serially diluted media, wherein the final dilution comprises 0% serum).

Additional steps are possible, such as steps to remove the selection marker. For example, in some embodiments, the selection marker can be an antibiotic resistance gene. As removing this gene enhances the safety of administering the composition, example embodiments include additional steps to remove the gene. In some examples, method includes selecting for specific clones of the *Leishmania* promastigotes that have lost the antibiotic resistance gene. For example, the method can include the steps of culturing single clones of the *Leishmania* promastigotes (for example, clones with a slow-growing phenotype, such as *Leishmania* promastigotes with a growth-arresting modification) in the presence and absence of antibiotic and selecting single clones of the *Leishmania* promastigotes that are not resistant to the antibiotic, thereby producing *Leishmania* promastigotes with the antibiotic resistance gene removed.

In some embodiments, the methods further include steps to facilitate culture of live, attenuated *Leishmania* as disclosed herein in serum-free media. In example embodiments, the method includes serial dilution of serum-containing media in which the final dilution includes 0% serum. Various media and serum are included. For example, media can include cell or tissue culture media, such as provided in Arora (*Cell Culture Media: A Review*, dx.doi.org/10.13070/mm.en.3.175, incorporated herein by reference in its entirety), such as M199, Schneider's *drosophila* medium, RPMI-1640, and Novy-MacNeal-Nicolle (NNN) medium (for example, Limoncu et al, Journal of Clinical Microbiology, PMID: 9276434, incorporated herein by reference in its entirety). Other components, such as salts, antibiotics, buffers, specific cell growth/stability components, and the like can be included. In specific, non-liming examples, the media includes M199 426.5 ml/L (see, e.g., HiMedia, Medium 199: Product Information, 2011, accessed at himedialabs.com/TD/AT094A.pdf, incorporated herein by reference in its entirety), Pen Strep (100×) 5 ml (such as 10,000 units/ml of penicillin and 10,000 µg/ml of streptomycin or 50 units of penicillin and 50 µg of streptomycin) of this 100× solution is used in 1 L of medium, 1M HEPES 12.5 ml/L (pH 6.8 to 7.4), hemin 1000× (5 g/L) 1 ml/L, 25 mM adenosine 5 ml/L, and biotin 0.5 mg/L.

Figure 17A:
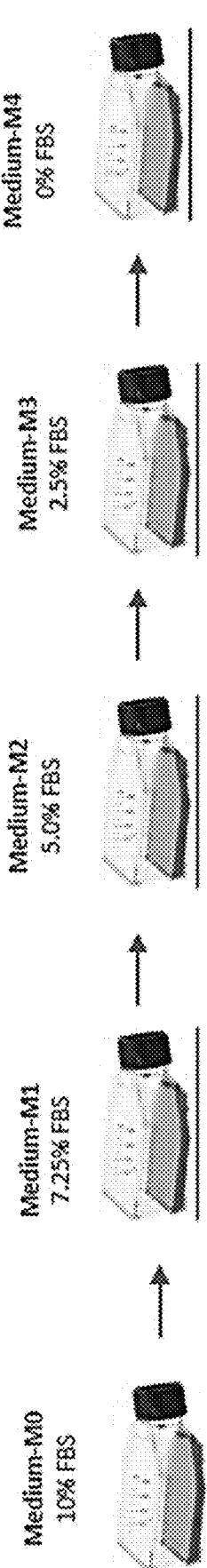
FIG. 17A shows a schematic diagram of an example serum weaning procedure, which can be used to identify a *Leishmania* species having a serum-free growth modification.
Figure 17B:
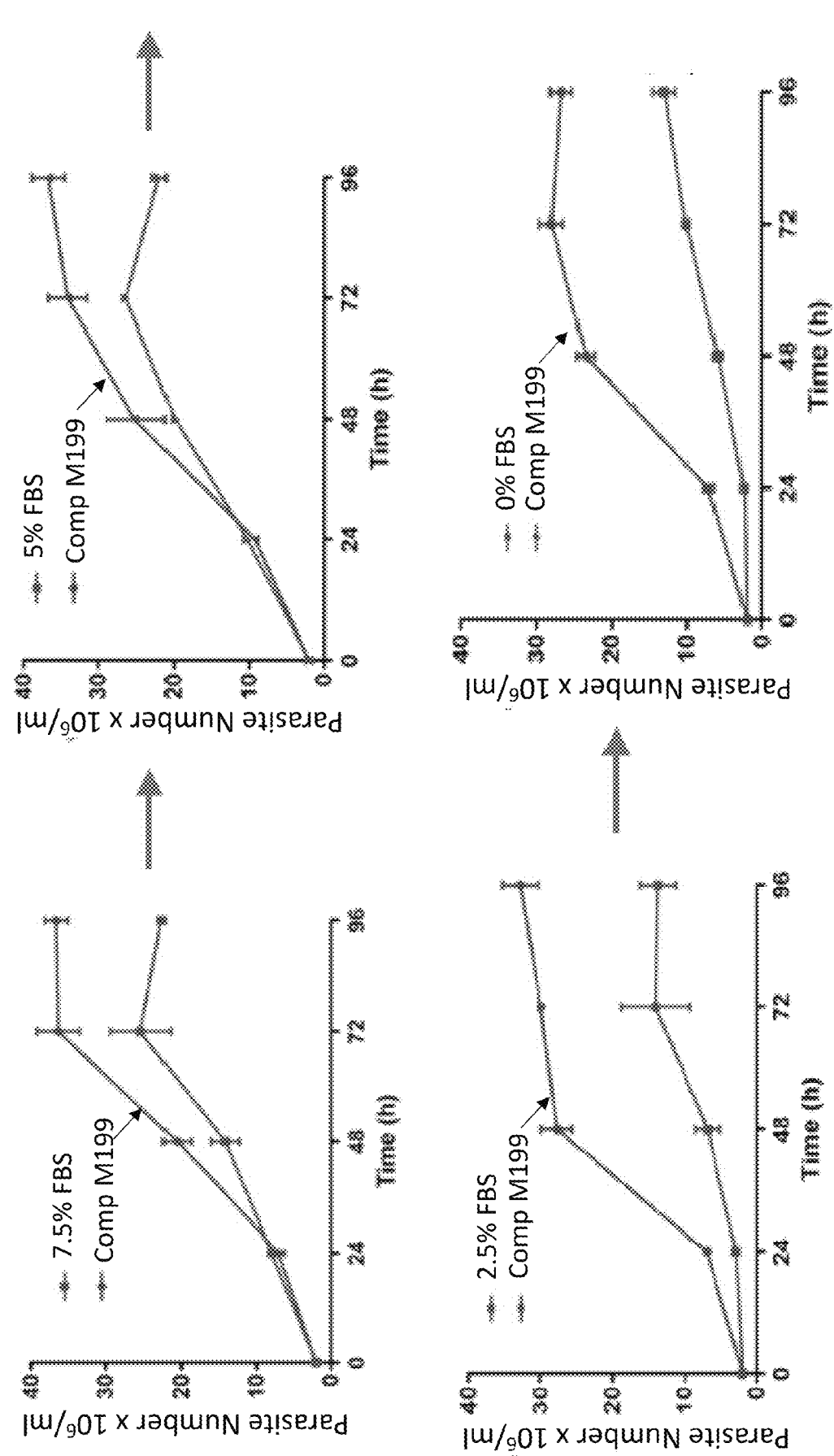
FIG. 17B shows a growth curve of LmCen–/– parasites in growth medium with sequentially reduced percentages of fetal bovine serum compared to parasites grown in medium containing 10% fetal bovine serum (Comp M199).

Serum can also be included in some steps or applications of the methods. For example, serum can be added to facilitate gene-editing or growth. In examples where serum-free media are desired, serum can be included in steps before the live, attenuated organisms are cultured in serum free media. A variety of serum types can be used, such as fetal bovine or fetal calf serum (FBS or FCS). Furthermore, the amount of serum used can vary. For example, at least about 1%, 2%, 3%, 4%, 5%, 6%, 7%, 8%, 9%, 10%, 11%, Or 12%, or about 0%-12%, 2%-10%, 1-2%, 1-3%, 1-5%, 2%-5%, 5%-10%, 5%-8%, 7%-10%, or 10%-12%, or 0%, 2.5%, 5%, 7.25%, and/or 10% serum can be used. In specific, non-limiting examples, FBS is used. In example embodiments, the serum included varies in amount through one or more serial dilution steps. For example, the amount of serum in the media can be decreased multiple times a periods of culture, such as at least 1, 2, 3, 4, 5, 6, 7, 8, 9, or 10 or about 1-10, 1-8, 1-5, 2-10, 2-5, or about 5 periods of culturing the live, attenuated *Leishmania* species in decreasing amounts of serum, for example, with the final culture in 0% serum. See exemplary serum-weaning procedure shown in FIGS. 17A-17B.

In further embodiments, the method includes steps directed to editing the genome of *Leishmania* promastigotes using the gene-editing complex. In example embodiments, the gene-editing complex is CRISPR/Cas. Therefore, additional steps are directed to this gene-editing complex, as described below.

CRISPR Gene Editing Systems

Genetic engineering through genome editing (the ability to insert, replace, and remove DNA) can confer disease resistance or remove malignant DNA, among many other applications. In specific examples, genetic engineering can be used to provide a safe, effective way of treating leishmaniasis.

CRISPR is an RNA-guided adaptive immune mechanism by which bacteria and archaea resist infection from invading viruses and plasmids. Foreign genetic material from a virus or a plasmid is acquired by and stored in a CRISPR complex, and this information is used to recognize and degrade complementary nucleic acids upon subsequent invasion. Efficient detection of invading DNA relies on complementary base pairing between the DNA target and the RNA guide sequence (such as crRNA and tracrRNA or single-guide RNA), in addition to recognition of a short sequence motif immediately adjacent to the target (that is, a proto-spacer-adjacent motif, PAM). This target nucleotide recognition mechanism allows for CRISPR technology to be adapted for genome editing. Upon recognition of the target sequence, the CRISPR-Cas complex introduces a break in the DNA, such as a double-strand break (for example, using the nuclease Cas9).

A variety of CRISPR systems are included, such as Cas9– (such as with crRNA and tracrRNA or single-guide RNA) or Cpf1-based CRISPR systems. In example embodiments, the CRISPR system is a Cas9-based CRISPR system. Cas9 is a nuclease that, when used in a CRISPR system, offers the simplicity of a single protein CRISPR system that can be programmed with at least one guide RNA (such as crRNA and tracrRNA or single-guide RNA) to target any complementary nucleic acid sequence flanked by a short PAM sequence motif (for example, WO 2014/093701 A1, incorporated herein by reference in its entirety). In example embodiments, the guide RNA can bind the nucleic acid flanking an amastigote growth-related gene (such as the centrin, KHARON1, Bt1, p27, Lpg-2, Ufm-1, or Ufsp gene). In specific, non-limiting examples, the guide RNA binds the nucleic acid flanking a centrin gene. Examples of guide RNA are shown below:

```
                        (SEQ ID NO: 1, guide RNA targeting
                    centrin and including cloning sites)
ATCGAAGACCTTTGTCTTCTCGCAATCCTTCTGCTGTTTTAGAGCTAGAA

ATAGCAAG (SEQ ID NO: 11)
CTTCTCGCAATCCTTCTGCTGTTTTAGAGCTAGAAATAGCAAGTTAAAAT

AAGGCTAGTCCGTTATCAACTTGAAAAAGTGGCACCGAGTCGGTGCTTTT

TT (SEQ ID NO: 2, guide RNA targeting
                    centrin and including cloning sites)
ATCGAAGACCCAAACTTGAGAGGGAAAGCAACGGACACCATGACGAGCTT

ACTC.

(SEQ ID NO: 12)
TCCGTTGCTTTCCCTCTCAAGTTTTAGAGCTAGAAATAGCAAGTTAAAAT

AAGGCTAGTCCGTTATCAACTTGAAAAAGTGGCACCGAGTCGGTGCTTTT

TT
```

In example embodiments, off-target effects from use of the CRISPR system can be reduced. For example, homologous recombination (HR) can be used (see, for example, US Pat Pub No: US 2017/0306306 A1, incorporated herein in its entirety). In some examples, HR can increase fidelity, for example, compared with the alternative repair process, non-homologous end-joining (NHEJ). In order to facilitate HR-mediated repair, an additional nucleic acid, 'donor DNA' (such as a single-strand or double-strand DNA), can also be supplied to the cell as a template for the desired mutation (for example, an amastigote growth-arresting modification as disclosed herein).

In specific, non-limiting examples, the donor DNA can be directed to gene deletion, such as in chromosomal repair after a gene is removed (for example, an amastigote growth-arresting gene, such as a centrin, kharon1, Bt1, p27, Lpg-2, Ufm-1, or Ufsp gene). For example, the donor DNA can be a contiguous sequence complementary to the sequences flanking the amastigote growth-related gene. In specific, non-limiting examples, the donor DNA is directed to deleting the centrin gene, such as through providing flanking sequences for chromosome repair after the gene is deleted. Thus, in some examples, the donor DNA is a contiguous sequence complementary to the sequences flanking this gene. Examples of donor DNA for deleting the centrin gene are as follows:

```
                                        (SEQ ID NO: 3)
ATTTCGTGCTTCTCGCAATCCTTCTCAACGGATGATAGTGCGCGTGTGC

G.
```

The CRISPR/Cas9 HR gene-editing complex can be introduced into *Leishmania* amastigotes in a variety of ways. In example embodiments, the gene-editing complex is introduced by at least one nucleic acid containing sequences that code for nuclease expression (for example, Cas9 expression), at least one guide RNA, or donor DNA, alone or in any combination. Examples of nucleic acids that contain such sequences include viral vectors (such as lentiviral, adenoviral, adeno-associated virus, and retroviral vectors) and non-viral vectors (such as standard or non-standard cloning vectors, for example, various nucleotide sequences directed to expressing nucleic acids, proteins, or peptides). See, for example, OriGene, CRISPR/Cas9 Genome Editing, as available Oct. 22, 2019, cdn.origene.com/assets/documents/crispr-cas9/crispr_manual.pdf, describing gene-editing complexes as well as vectors that can be used to express such complexes, In specific, non-limiting examples, the gene-editing complexes (such as CRISPR/Cas9 complexes as disclosed herein) can be introduced into *Leishmania* amastigotes using the pLdCN vector (see, for example, addgene, pLdCN: Plasmid #84290, as available Oct. 22, 2019, addgene.org/84290/).

Immunogenic and Pharmaceutical Compositions

Immunogenic and pharmaceutical compositions provided herein include live, attenuated *Leishmania* as disclosed. In some examples, the live, attenuated *Leishmania* (such as an immunogenic composition thereof) are provided as a vaccine. In example embodiments, the pharmaceutical compositions disclosed herein include the disclosed live, attenuated *Leishmania* (for example, provided as an immunogenic composition or a vaccine) and a pharmaceutically acceptable carrier. Such compositions can be administered to subjects by a variety of administration modes known to the person of ordinary skill in the art, for example, intramuscular, subcutaneous, intravenous, intra-arterial, intra-articular, intraperitoneal, or parenteral routes. In specific examples, the compositions can be administered via subcutaneous or intramuscular routes. Methods for preparing administrable compositions are known to those skilled in the art and are described in more detail in such publications as *Remington's Pharmaceutical Sciences*, by E.W. Martin, Mack Publishing Co., Easton, Pa., 22nd Edition, 2013.

Live, attenuated *Leishmania* described herein can be formulated in a variety of ways. In example embodiments, the live, attenuated *Leishmania* are formulated with pharmaceutically acceptable carriers (for example, as a pharmaceutical composition) to help retain biological activity while also promoting increased stability during storage within an acceptable temperature range. Potential carriers include, but are not limited to, physiologically balanced culture medium, phosphate buffered saline solution, water, emulsions (for example, oil/water or water/oil emulsions), various types of wetting agents, cryoprotective additives or stabilizers such as proteins, peptides or hydrolysates (for example, albumin, gelatin), sugars (for example, sucrose, lactose, sorbitol), amino acids (for example, sodium glutamate), or other protective agents.

Formulated compositions, especially liquid formulations, may contain a bacteriostat to prevent or minimize degradation during storage, including but not limited to effective concentrations (usually ≤1% w/v) of benzyl alcohol, phenol, m-cresol, chlorobutanol, methylparaben, and/or propylparaben. In example embodiments, the live, attenuated organisms (for example, in a disclosed immunogenic or pharmaceutical composition) are serum-free (such as a formulation with 0% serum. Serum-free compositions are a safer alternative to serum-containing compositions, which can, for example, be contaminated (such as with a transmissible spongiform encephalopathy (TSE) agent). Therefore, in example embodiments, the compositions are not contaminated with a transmissible spongiform encephalopathy (TSE) agent.

The compositions of the disclosure can contain as pharmaceutically acceptable carriers, substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate.

The disclosed compositions (such as immunogenic compositions, for example, vaccines, or pharmaceutical compositions) may optionally include an adjuvant to enhance an immune response of the host. Adjuvants, such as aluminum hydroxide (ALHYDROGEL®, available from Brenntag Biosector, Copenhagen, Denmark and Amphogel®, Wyeth Laboratories, Madison, N.J.), Freund's adjuvant, MPL™ (3-O-deacylated monophosphoryl lipid A; Corixa, Hamilton, Ind.), IL-12 (Genetics Institute, Cambridge, Mass.), TLR agonists (such as TLR-9 agonists), among many other suitable adjuvants, can be included in the compositions. Suitable adjuvants are, for example, toll-like receptor agonists, alum, AlPO4, alhydrogel, Lipid-A and derivatives or variants thereof, oil-emulsions, saponins, neutral liposomes, liposomes containing the vaccine and cytokines, non-ionic block copolymers, and chemokines. Non-ionic block polymers containing polyoxyethylene (POE) and polyxylpropylene (POP), such as POE-POP-POE block copolymers, MPL™ (3-O-deacylated monophosphoryl lipid A; Corixa, Hamilton, Ind.) and IL-12 (Genetics Institute, Cambridge, Mass.), among many other suitable adjuvants well known in the art, may be used as an adjuvant (Newman et al., 1998, *Critical Reviews in Therapeutic Drug Carrier Systems* 15:89-142). These adjuvants help to stimulate the immune system in a non-specific way, thus enhancing the immune response to a pharmaceutical product. In some embodiments, the adjuvant is selected to elicit a Th1 biased immune response in a subject.

In some instances, the adjuvant formulation includes a mineral salt, such as a calcium or aluminum (alum) salt, for example calcium phosphate, aluminum phosphate or aluminum hydroxide. In some embodiments, the adjuvant includes an oil and water emulsion, for example, an oil-in-water emulsion (such as MF59 (Novartis) or AS03 (GlaxoSmithKline)). One example of an oil-in-water emulsion comprises a metabolizable oil, such as squalene, a tocol such as a tocopherol, for example, alpha-tocopherol, and a surfactant, such as sorbitan trioleate (Span 85) or polyoxyethylene sorbitan monooleate (Tween 80), in an aqueous carrier.

In some instances, it may be desirable to combine a disclosed composition with other pharmaceutical products, which induce protective responses to other agents. For example, a composition including a live, attenuated organism as described herein can be administered simultaneously or sequentially with other vaccines recommended by the Advisory Committee on Immunization Practices (ACIP; cdc.gov/vaccines/acip/index) for the targeted age group (for example, children at or less than 5 years old, children at or less than one year old, children over 5 years old, or adults). As such, a disclosed composition described herein may be administered simultaneously or sequentially with vaccines against, for example, typhoid (for example, Ty21a), measles virus, rubella virus, varicella zoster virus, hepatitis B (HepB), diphtheria, tetanus and pertussis (DTaP), pneumococcal bacteria (PCV), *Haemophilus influenzae* type b (Hib), polio, influenza, and/or rotavirus.

In some embodiments, the composition can be provided as a sterile composition. The composition typically contains an effective amount of a disclosed live, attenuated organism. Typically, the amount of live, attenuated organism in each dose of the composition is selected as an amount which induces an immune response without significant, adverse side effects. In some embodiments, the composition can be provided in unit dosage form for use to induce an immune response in a subject, for example, to prevent or inhibit leishmaniasis in the subject. A unit dosage form contains a suitable single preselected dosage for administration to a subject, suitable marked or measured multiples of two or more preselected unit dosages, and/or a metering mechanism for administering the unit dose or multiples thereof.

Methods of Treatment

Disclosed herein are methods of treating subjects for leishmaniasis. The methods include administering the live, attenuated *Leishmania* disclosed herein (or immunogenic compositions, vaccines, or pharmaceutical compositions thereof) to a subject with or at risk of infection by *Leishmania*, thereby treating the subject. In some examples, the methods induce an immune response to *Leishmania* (such as *L. infantum, L. aethiopica, L. amazonensis, L. Arabica, L. archibaldi, L. aristedesi, L. braziliensis, L. chagasi, L. colombiensis, L. deanei, L. donovani, L. enriettii, L. equatorensis, L. forattinii, L. garnhami, L. gerbil, L. guyanensis, L. herreri, L. hertigi, L. killicki, L. lainsoni, L. major, L. Mexicana, L. naiffi, L. panamensis, L. peruviana, L. pifanoi, L. shawi, L. tarentolae, L. tropica, L. turanica,* or *L. venezuelensis*) in a subject. In some embodiments, the subject is a human. The immune response can be a protective immune response, for example, a response that prevents or reduces subsequent infection by *Leishmania*. Eliciting the immune response can also be used to treat or inhibit *Leishmania* infection and illnesses associated therewith (such as leishmaniasis).

A subject can be selected for treatment that has or is at risk for developing leishmaniasis, for example, due to exposure or the possibility of exposure to *Leishmania* (such as *L. infantum, L. aethiopica, L. amazonensis, L. Arabica, L. archibaldi, L. aristedesi, L. braziliensis, L. chagasi, L. colombiensis, L. deanei, L. donovani, L. enriettii, L. equatorensis, L. forattinii, L. garnhami, L. gerbil, L. guyanensis, L. herreri, L. hertigi, L. killicki, L. lainsoni, L. major, L. Mexicana, L. naiffi, L. panamensis, L. peruviana, L. pifanoi, L. shawi, L. tarentolae, L. tropica, L. turanica,* or *L. venezuelensis*). Following administration of a disclosed composition, the subject can be monitored for *Leishmania* infection, symptoms associated therewith, or both.

The methods can be used to treat infection by a variety of *Leishmania* species, including cutaneous, mucocutaneous, and visceral *Leishmania* species. Typical subjects for administration or treatment with the compositions and methods of the present disclosure include humans and any other animals susceptible to infection. For example, leishmaniasis is associated with malnutrition, population displacement, poor housing, a weak immune system and lack of financial resources as well as environmental changes such as deforestation, building of dams, irrigation schemes, and urbanization. All three types of *Leishmania* species (cutaneous, mucocutaneous, and visceral) can be diagnosed by seeing the parasites under the microscope, and visceral *Leishmania* infection can also be diagnosed through blood tests.

In example embodiments, the methods include selecting a subject with or at risk of a visceral *Leishmania* infection (visceral leishmaniasis). A variety of *Leishmania* species can cause infection (visceral leishmaniasis), such as *L. donovani, L. infantum,* or *L. chagasi.* Visceral *Leishmania* infection can be fatal, and signs and symptoms of visceral *Leishmania* infection (or visceralization) include fever, weight loss, fatigue, anemia, substantial swelling of the liver and spleen, and, in some cases, blackening of the skin. Visceral *Leishmania* infection can be primary or secondary (re-infection after recovery from leishmaniasis, which, in some examples, can be evidenced by small skin lesions that gradually increase in size and number, eventually resembling leprosy). Exemplary methods of diagnosing visceral *Leishmania* infection include visualization of the amastigotes in splenic aspirate or bone marrow aspirate and serological testing (e.g., using rK39 immunochromatographic test, the endemic latex agglutination test; the DAT anti-*leishmania* antigen test, and tests for erythrosalicylic acid). The methods include administering the live, attenuated organisms disclosed herein (or immunogenic compositions, vaccines, or pharmaceutical compositions thereof) to a subject with or at risk of infection by visceral *Leishmania,* thereby treating the subject. For example, the methods include administering live, attenuated organisms or compositions thereof with at least one serum-free growth modification, at least one amastigote growth-arresting modification, the absence of an antibiotic-resistance gene, or any combination thereof. In some embodiments, the methods include administering live, attenuated organisms or compositions thereof including a cutaneous or mucocutaneous *Leishmania* species with at least one serum-free growth modification, at least one amastigote growth-arresting modification, and the absence of an antibiotic-resistance gene. In specific, non-limiting examples, the live, attenuated organisms include *L. major* at least one serum-free growth modification, a centrin gene deletion, and the absence of an antibiotic-resistance gene.

In example embodiments, the methods include selecting a subject with or at risk of a cutaneous *Leishmania* infection (cutaneous leishmaniasis). A variety of *Leishmania* species can cause infection (cutaneous leishmaniasis), such as *L. major, L. mexicana, L. tropica, L. aethiopica, L. amazonensis, L. braziliensis, L. infantum,* or *L. panamensis.* Cutaneous *Leishmania* infection is a skin infection, which can be diagnosed in a variety of ways. For example, cutaneous *Leishmania* infection include a clinical diagnosis based on characteristic appearance of non-healing, raised, scaling lesions, which may ulcerate and become secondarily infected with other organisms, fine-needle aspiration of the lesion with visualization of the amastigote form of *Leish-*

*mania,* and PCR. The methods include administering the live, attenuated organisms disclosed herein (or immunogenic compositions, vaccines, or pharmaceutical compositions thereof) to a subject with or at risk of infection by cutaneous *Leishmania,* thereby treating the subject. For example, the methods include administering live, attenuated organisms or compositions thereof with at least one serum-free growth modification, at least one amastigote growth-arresting modification, the absence of an antibiotic-resistance gene, or any combination thereof. In some embodiments, the methods include administering live, attenuated organisms or compositions thereof including a cutaneous or mucocutaneous *Leishmania* species with at least one serum-free growth modification, at least one amastigote growth-arresting modification, and the absence of an antibiotic-resistance gene. In specific, non-limiting examples, the live, attenuated organisms include *L. major* at least one serum-free growth modification, a centrin gene deletion, and the absence of an antibiotic-resistance gene.

In example embodiments, the methods include selecting a subject with or at risk of a mucocutaneous *Leishmania* infection (mucocutaneous leishmaniasis). A variety of *Leishmania* species can cause infection (mucocutaneous leishmaniasis), such as *L. amazonensis, L. braziliensis,* or *L. aethiopica.* Mucocutaneous *Leishmania* infection can present as destructive and disfiguring lesions of the face. Exemplary methods of diagnosing mucocutaneous *Leishmania* infection include fine-needle aspiration of the lesion with visualization of the amastigote form of *Leishmania* and PCR. The methods include administering the live, attenuated organisms disclosed herein (or immunogenic compositions, vaccines, or pharmaceutical compositions thereof) to a subject with or at risk of infection by mucocutaneous *Leishmania,* thereby treating the subject. For example, the methods include administering live, attenuated organisms or compositions thereof with at least one serum-free growth modification, at least one amastigote growth-arresting modification, the absence of an antibiotic-resistance gene, or any combination thereof. In some embodiments, the methods include administering live, attenuated organisms or compositions thereof including a cutaneous or mucocutaneous *Leishmania* species with at least one serum-free growth modification, at least one amastigote growth-arresting modification, and the absence of an antibiotic-resistance gene. In specific, non-limiting examples, the live, attenuated organisms include *L. major* at least one serum-free growth modification, a centrin gene deletion, and the absence of an antibiotic-resistance gene.

Administration of a disclosed live, attenuated modified *Leishmania* species (such as a disclosed immunogenic composition, vaccine, or pharmaceutical composition thereof) can be for prophylactic or therapeutic purpose. When provided prophylactically, the live, attenuated *Leishmania* can be provided in advance of any symptom, for example, in advance of infection. The prophylactic administration serves to prevent or ameliorate any subsequent infection. In some embodiments, the methods can involve selecting a subject at risk for contracting leishmaniasis and administering a therapeutically effective amount of a disclosed live, attenuated organism to the subject. The live, attenuated *Leishmania* can be provided prior to the anticipated exposure to a *Leishmania* species so as to attenuate the anticipated severity, duration, or extent of an infection and/or associated disease symptoms, after exposure or suspected exposure to the pathogen, or after the actual initiation of an infection. When provided therapeutically, the disclosed live, attenuated organisms are provided at or after the onset of a symptom of *Leishmania* infection or after diagnosis of *Leishmania* infection.

In some embodiments, administration of a disclosed live, attenuated *Leishmania* to a subject can elicit the production of an immune response that is protective against or reduces the severity of complications of *Leishmania* infection, such as skin lesions, facial disfigurement, and visceralization of the *Leishmania*, when the subject is subsequently infected or re-infected with *Leishmania*. While the naturally circulating pathogen may still be capable of causing infection, there can be a reduced possibility of symptoms as a result of the vaccination and a possible boosting of resistance to subsequent infection by *Leishmania*.

The live, attenuated *Leishmania* described herein as well as compositions thereof (such as disclosed immunogenic compositions, vaccines, or pharmaceutical compositions thereof) are provided to a subject in an amount effective to induce or enhance an immune response against *Leishmania* in the subject, such as a human. The actual dosage of disclosed live, attenuated organism will vary according to factors, such as the disease indication and particular status of the subject (for example, the subject's age, size, fitness, extent of symptoms, susceptibility factors, and the like), time and route of administration, other drugs or treatments being administered concurrently, as well as the specific pharmacology of the composition for eliciting the desired activity or biological response in the subject. Dosage regimens can be adjusted to provide an optimum prophylactic or therapeutic response.

A composition including one or more of the disclosed live, attenuated *Leishmania* can be used in coordinate (or prime-boost) vaccination protocols or combinatorial formulations. In certain embodiments, novel combinatorial immunogenic compositions and coordinate immunization protocols employ separate immunogens or formulations, each directed toward eliciting an anti-pathogen immune response, such as an immune response to proteins from *Leishmania*. Separate immunogenic compositions that elicit an anti-pathogen immune response can be combined in a polyvalent immunogenic composition administered to a subject in a single immunization step, or they can be administered separately (in monovalent immunogenic compositions) in a coordinate (or prime-boost) immunization protocol.

There can be several boosts, and each boost can be the same or a different disclosed immunogen (such as several boosts with a live, attenuated *Leishmania* species with a centrin gene deletion or several boosts with a live, attenuated *Leishmania* species, each with different amastigote grow-arresting modifications). In some examples, the boost may be the same live, attenuated *Leishmania* species as another boost or the prime. The prime and boost can be administered as a single dose or multiple doses, for example two doses, three doses, four doses, five doses, six doses, or more can be administered to a subject over days, weeks, or months. Multiple boosts can also be given, such one to five (for example, 1, 2, 3, 4, or 5 boosts) or more. Different dosages can be used in a series of sequential immunizations. For example, a relatively large dose can be used in a primary immunization and then a boost with relatively smaller doses.

In some embodiments, the boost can be administered about two, about three to eight, or about four, weeks following the prime, or several months after the prime. In some embodiments, the boost can be administered about 5, about 6, about 7, about 8, about 10, about 12, about 18, about 24, about 36, about 48, or about 50 months after the prime, or more or less time after the prime. Periodic additional boosts can also be used at appropriate time points to enhance the subject's "immune memory." The adequacy of the vaccination parameters chosen, for example, formulation, dose, regimen, and the like, can be determined by taking aliquots of serum from the subject and assaying antibody titers during the course of the immunization program. In some examples, cytokines are measured following immunization. For example, cytokines can be measured to indicate efficacy and/or safety after vaccination (see, e.g., Eriksson et al., Influenza Other Respir Viruses. 2007 July; 1(4):139-46, incorporated herein by reference in its entirety). In addition, the clinical condition of the subject can be monitored for the desired effect, for example, prevention of *Leishmania* infection or improvement in disease state (for example, reduction in pathogen load). If such monitoring indicates that vaccination is sub-optimal, the subject can be boosted with one or more additional doses, and the administration parameters can be modified in a fashion expected to potentiate the immune response.

The amount utilized in an immunogenic composition is selected based on the subject population (for example, infant or elderly). An optimal amount for a particular composition can be ascertained by standard studies involving observation of antibody titers and other responses in subjects. It is understood that a therapeutically effective amount of a disclosed live, attenuated organisms or composition thereof (such as immunogenic compositions, vaccines, or pharmaceutical compositions thereof), can include an amount that is ineffective at eliciting an immune response by administration of a single dose, but that is effective upon administration of multiple dosages, for example, in a prime-boost administration protocol. In specific, non-limiting examples, each dose can be at least about $10^2$, $10^3$, $10^4$, $10^5$, $10^6$, $10^7$, $10^8$, $10^9$, or $10^{10}$, or about $10^2$-$10^{10}$, $10^3$-$10^9$, $10^4$-$10^8$, or $10^5$-$10^7$ cfu.

Upon administration of a disclosed live, attenuated organisms, the immune system of the subject typically responds to the immunogenic composition by producing antibodies specific for a pathogenic protein. Such a response signifies that an immunologically effective dose was delivered to the subject.

For each particular subject, specific dosage regimens can be evaluated and adjusted over time according to the individual need and professional judgment of the person administering or supervising the administration of the live, attenuated organism. The dosage and number of doses will depend on the setting, for example, in an adult or anyone primed by prior *Leishmania* infection or immunization, a single dose may be a sufficient booster. In naïve subjects, in some examples, at least two doses would be given, for example, at least three doses.

In some embodiments, the antibody response or the response to the leishmanin skin test (LST) of a subject will be determined in the context of evaluating effective dosages/immunization protocols. In most instances, it will be sufficient to assess the antibody titer in serum or plasma obtained from the subject or the LST in the skin of the subject. Decisions as to whether to administer booster inoculations and/or to change the amount of the therapeutic agent administered to the individual can be at least partially based on the antibody titer level or the LST. The antibody titer level can be based on, for example, an immunobinding assay which measures the concentration of antibodies in the serum which bind to a *Leishmania* protein. The LST can be based, for example, on the DTH reaction in the skin at the site of the LST.

Determination of effective dosages is typically based on animal model studies followed up by human clinical trials and is guided by administration protocols that significantly reduce the occurrence or severity of targeted disease symptoms or conditions in the subject, or that induce a desired response in the subject (such as a neutralizing immune response). Suitable models in this regard include, for example, murine, rat, porcine, feline, ferret, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of the composition (for example, amounts that are effective to elicit a desired immune response or alleviate one or more symptoms of a targeted disease). In alternative embodiments, an effective amount or effective dose of the composition may simply inhibit or enhance one or more selected biological activities correlated with a disease or condition, as set forth herein, for either therapeutic or diagnostic purposes.

Administration of a composition that elicits an immune response to reduce or prevent a *Leishmania* infection, can, but does not necessarily completely, eliminate such an infection, so long as the infection is measurably diminished. For example, administration of an effective amount of the composition can decrease the *Leishmania* infection (for example, as measured by infection of cells (such as macrophages), infection of draining lymph nodes, or by number or percentage of subjects infected by *Leishmania*, for example, a decrease of at least 10%, at least 20%, at least 50%, at least 60%, at least 70%, at least 80%, at least 90%, at least 95%, at least 98%, or even at least 100% (elimination or prevention of detectable *Leishmania*, as compared to a suitable control). In some examples, administration of an effective amount of the composition can decrease the number and/or size of *Leishmania* lesions (such as the diameter of a lesion) for example, a decrease of at least 10%, at least 20%, at least 50%, at least 60%, at least 70%, at least 80%, at least 90%, at least 95%, at least 98%, or even at least 100% (elimination or prevention of detectable *Leishmania* lesions, as compared to a suitable control). In some examples, administration of an effective amount of the composition can decrease the size or weight of a spleen and/or liver for example, a decrease of at least 10%, at least 20%, at least 50%, at least 60%, at least 70%, at least 80%, at least 90%, at least 95%, at least 98%, or even at least 100% (elimination or prevention of detectable *Leishmania* lesions, as compared to a suitable control). In some examples, administration of an effective amount of the composition can provide protection against a future *Leishmania* infection (for example, as measured by infection of cells, infection of lymph nodes, or by number or percentage of subjects infected by *Leishmania*, for example, a decrease in recurrence of a *Leishmania* infection by at least 10%, at least 20%, at least 50%, at least 60%, at least 70%, at least 80%, at least 90%, at least 95%, at least 98%, or even at least 100% (elimination of detectable *Leishmania* in re-infected subjects, as compared to a suitable control). In some examples, combinations of these effects are achieved. In some examples, administration of an effective amount of the composition can provide protection against a future infection by a different species of *Leishmania* than that used in the initial administration (for example, cross-protection is achieved, for example as measured by infection of cells, infection of lymph nodes, or by number or percentage of subjects infected by a different *Leishmania* species, for example, a decrease of infection by a different *Leishmania* species, by at least 10%, at least 20%, at least 50%, at least 60%, at least 70%, at least 80%, at least 90%, at least 95%, at least 98%, or even at least 100% (no detection of the different *Leishmania* species, as compared to a suitable control). In some examples, combinations of these effects are achieved.

In some embodiments, administration of a therapeutically effective amount of one or more of the disclosed live, attenuated *Leishmania* species to a subject induces a neutralizing immune response in the subject. To assess neutralization activity, following immunization of a subject, serum can be collected from the subject at appropriate time points, frozen, and stored for neutralization testing. Methods to assay for neutralization activity include, but are not limited to microneutralization assays, flow cytometry-based assays, and single-cycle infection assays.

In certain embodiments, the live, attenuated *Leishmania* species can be administered in combination with other anti-*Leishmania* therapeutic agents (such as liposomal amphotericin B, amphotericin, pentavalent antimonials, paromomycin, fluconazole, itraconazole, or combinations thereof) In some example, the live, attenuated *Leishmania* species is administered before or after the other agent. Sequential administration can mean immediately following or after an appropriate period of time, such as hours, days, weeks, months, or even years later. In some example, the live, attenuated *Leishmania* species is administered contemporaneously with the other agent.

The following examples are provided to illustrate certain particular features and/or embodiments. These examples should not be construed to limit the disclosure to the particular features or embodiments described.

Examples

Leishmanization with wildtype *L. major* has previously been the only successful human vaccine for leishmaniasis, but it is ethically unacceptable because it causes skin lesions that last for months. These examples disclose a new type of leishmanization live vaccination using an attenuated *L. major* strain (LmCen$^{-/-}$) that does not cause lesions, but retains the ability to provide immunological protection against experimental needle- and sand fly-transmitted *Leishmania* infection.

LmCen$^{-/-}$ is the first genetically engineered, gene-deleted *Leishmania* strain that is free of antibiotic-resistance markers and does not have off-target mutations. Mice immunized with LmCen$^{-/-}$ exhibited virtually no visible lesions following challenge with *L. major*-infected sand flies, while non-immunized animals developed large and progressive lesions with a 2 log-fold higher parasite burden. LmCen$^{-/-}$ immunization showed protection comparable to leishmanization, but LmCen$^{-/-}$ is safe because it does not produce disease in normal or immunocompromised mice and is marker-free, which is necessary for human vaccines.

Disclosed herein, CRISPR-Cas genome editing was used for *Leishmania* (Zhang, W. W. & Matlashewski, G., MBio 6, e00861-15 (2015); Zhang, W.-W., Lypaczewski, P. & Matlashewski, G., mSphere 2, 1-15 (2017)) to generate an attenuated *L. major* centrin gene-deletion mutant (LmCen$^{-/-}$). This represents a major milestone because LmCen$^{-/-}$ is the first gene-deleted *Leishmania* parasite to be developed without antibiotic-resistance selection genes, which is necessary for human use. *L. major* was used because this species is safe (for example, compared with visceral species, such as *L. donovani*), as *L. major* is a cutaneous species and, thus, remains in the skin at the site of infection, which does not cause visceral leishmaniasis (Burza, S., Croft, S. L. & Boelaert, Lancet 392, 951-970 (2018); McCall, L. I., Zhang, W. W. & Matlashewski, G., PLoS Pathogens 9 (2013)). As demonstrated herein, vaccination with LmCen$^{-/-}$ is safe, immunogenic, and protective against sand fly-transmitted *L. major* infection, that mimics natural infection in highly relevant cutaneous leishmaniasis animal models meeting efficacy and ethical standards for advancement to human clinical studies.

Figure 18A:
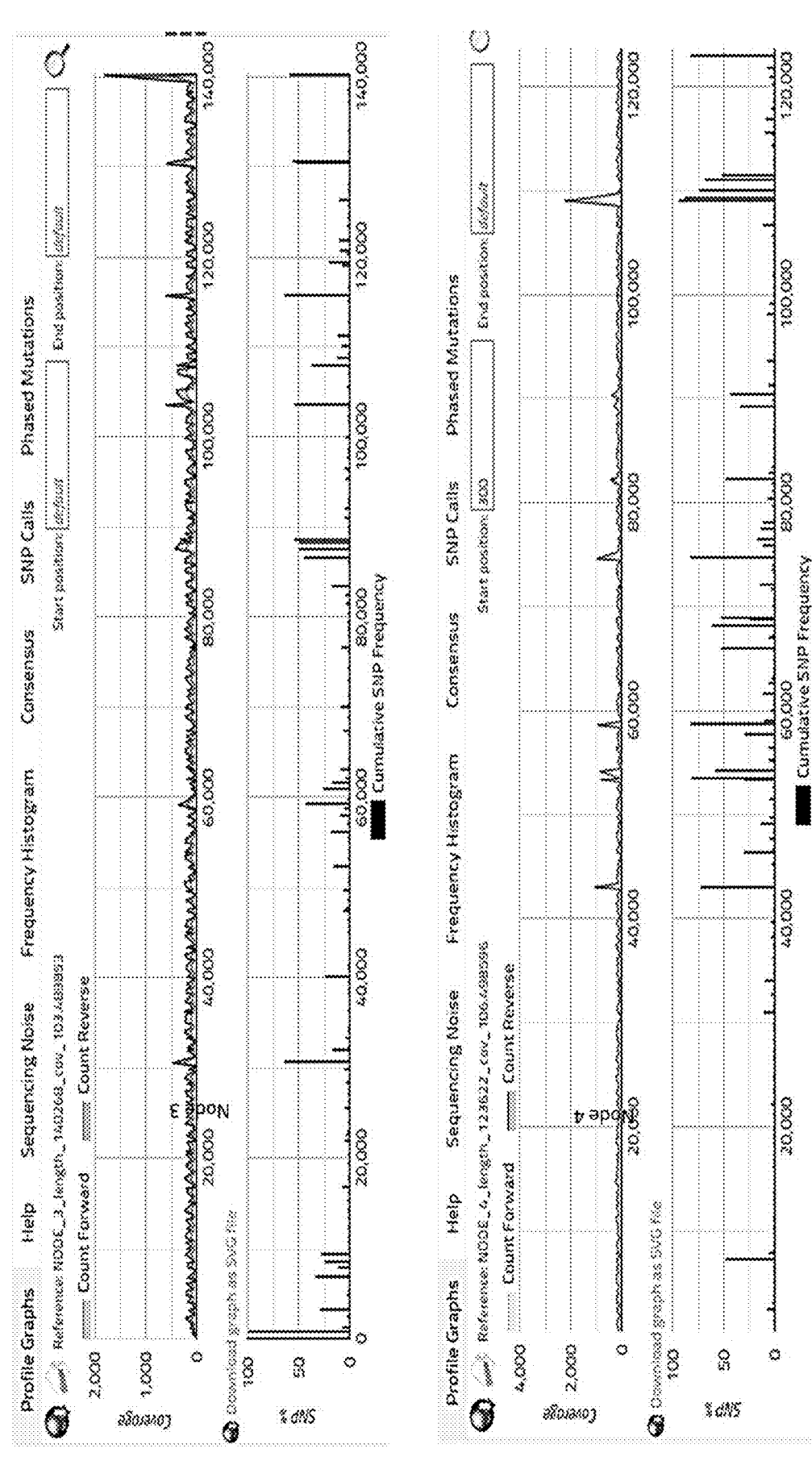
Figure 18B:
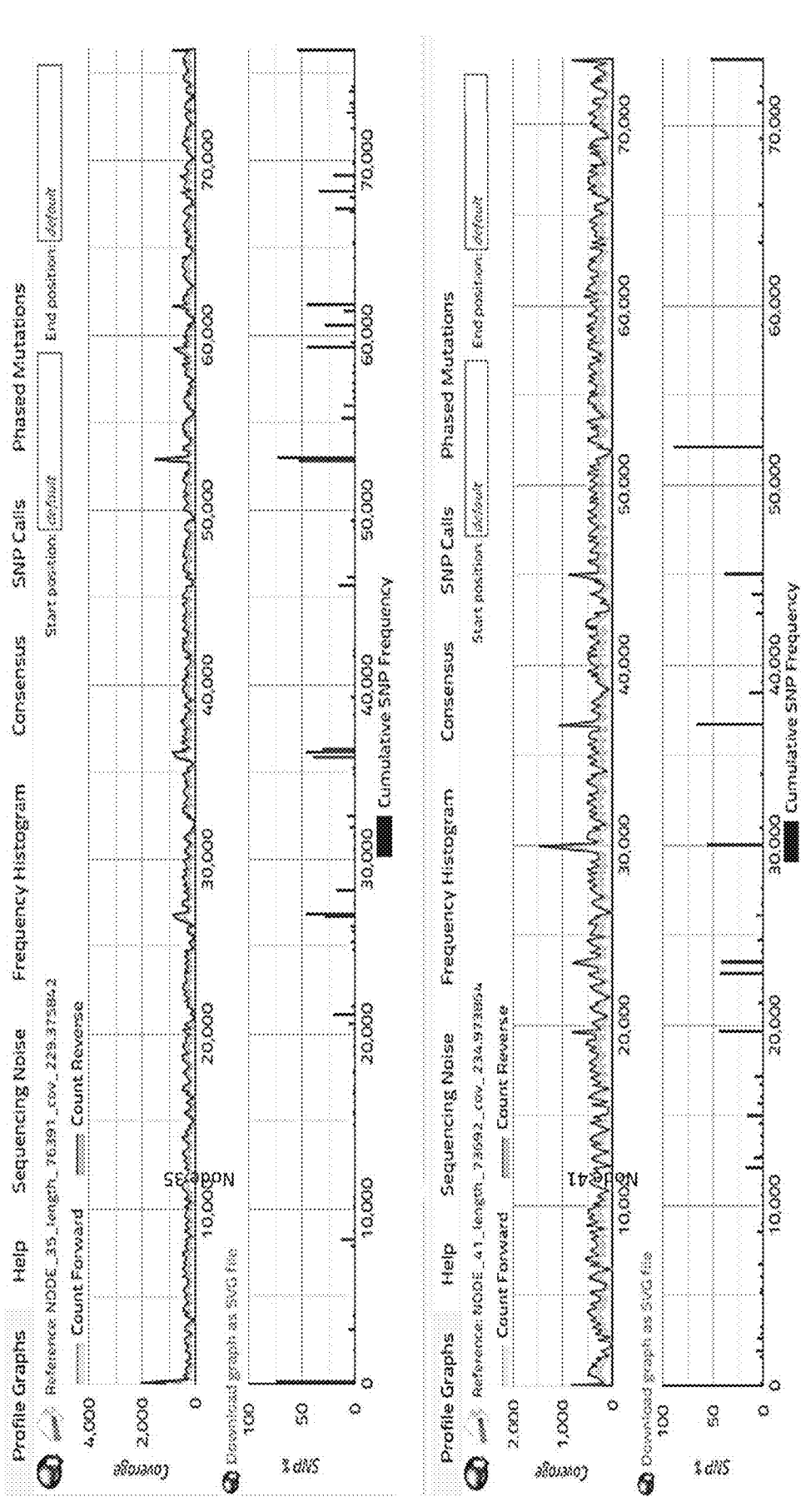
Figure 18D:
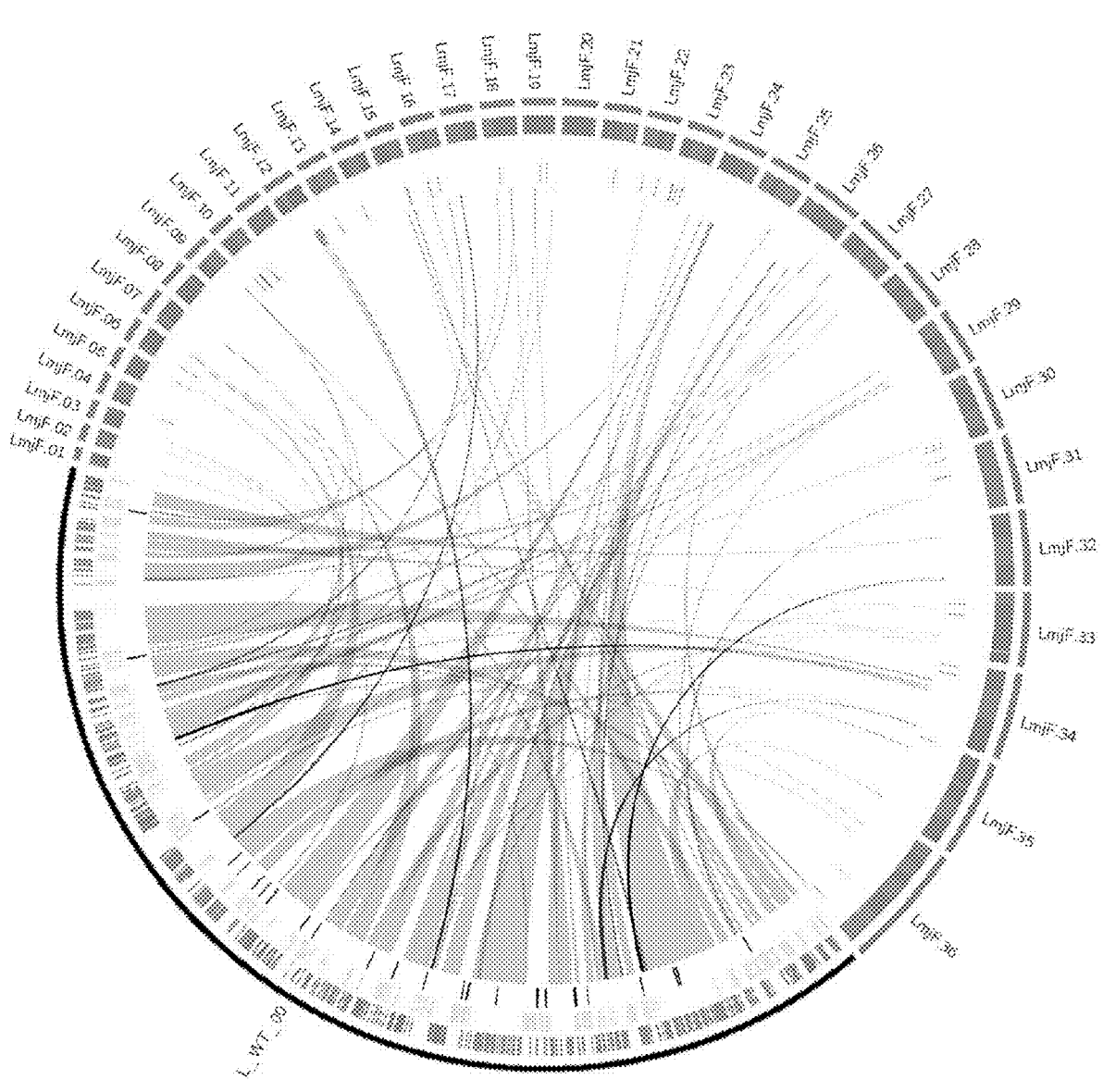

CRISPR-Cas genome editing was used to generate the marker free strain in order to delete genes with high specificity and fidelity without selection with antibiotic resistant marker genes (Zhang, W. W. & Matlashewski, G., MBio 6, e00861-15 (2015); Zhang, W.-W., Lypaczewski, P. & Matlashewski, G., mSphere 2, 1-15 (2017)). Selection was based on a reduced proliferation rate of the LmCen$^{-/-}$ mutant identified through single cell cloning, which is the first time such selection has been performed in *Leishmania*. A whole genome sequence analysis confirmed that only the centrin gene on chromosome 22 (ID:LmjF.22.1410) was deleted at the CRISPR guide RNA targeting sites, and the other centrin gene members on chromosomes 7, 32, 34 and 36 remained intact (FIGS. 2A-2D and 18A-18B). Furthermore, LmCen$^{-/-}$ parasites grown in media containing serum or in serum free media had comparable scaffolds with no large-scale rearrangements across their genomes (FIGS. 18C-18D). This CRISPR method did not induce off-target gene deletions, indels, or nonsynonymous SNPs in the LmCen$^{-/-}$ clone subjected to whole genome sequencing. By comparison, previous parasites with *L. donovani* centrin gene deletion generated by homologous recombination with antibiotic resistant marker genes did contain off-target genomic deletions of up to 5000 base pairs in non-coding regions and in the coding regions of the folate transporter and gp63 genes (Gannavaram, S. et al., Sci. Rep. 7, (2017)). These observations demonstrate that CRISPR-Cas gene editing in *Leishmania* using a donor DNA fragment for repair as detailed in FIG. 1 is more specific than traditional homologous recombination-based gene replacement with antibiotic resistance markers. Centrin gene-deleted *L. donovani* parasites have been the most extensively validated parasites in previous experimental vaccine studies using various animal models (Selvapandiyan, A. et al., J. Immunol. (2009); Fiuza, J. A. et al., Vaccine (2013), doi:10.1016/j.vaccine.2013.01.048; Dey, R. et al. J. Immunol. (2014), doi:10.4049/jimmunol.1303145; Gannavaram, S. et al., Methods in Molecular Biology (2016), doi:10.1007/978-1-4939-3387-7_35; Banerjee, A. et al., J. Immunol. (2017), doi:10.4049/jimmunol.1700674).

LmCen$^{-/-}$ induced comparable innate and adaptive responses compared with wildtype *L. major*, including leishmanization, showing that deletion of the centrin gene yields effective parasite detection by the host immune system. Parasitized dendritic cells exhibited increased expression of costimulatory molecules and pro-inflammatory cytokines IL-12 and IL-6. LmCen$^{-/-}$ immunized animals showed increased expression of the pro-inflammatory cytokines IFN-γ and TNF upon restimulation with *Leishmania* antigens. The increased expression of CD40, MHCII, and the inflammatory cytokines IL-12 and IL-6 that was observed in LmCen$^{-/-}$ parasites was abrogated in mice infected with a LmCen$^{-/-AB}$ mutant and was similar to the LmWT parasite infection, demonstrating that the differential activation is due to the attenuated virulence of LmCen-parasites.

Previous studies with *L. major* infection in C57BL/6 mice showed that a central memory CD4$^+$ T cell response is generated early in the infection (Colpitts, S. L. & Scott, P., J. Immunol. (2010), doi:10.4049/jimmunol.1000483). In this example, both LmWT and LmCen$^{-/-}$ parasites induce central memory (CD4$^+$CD44$^+$CD62L$^{hi}$IL-7R$^+$) T cells early during infection. However, unlike in LmWT infection, significantly more memory T-cells persisted in LmCen$^{-/-}$-immunized mice at 7 weeks-post-immunization when the majority of the parasites were cleared by the host. Persistence of a low-grade parasitemia is important for maintaining a memory and an effector response that mediate long-term protection against future infections (Zaph, C., Uzonna, J., Beverley, S. M. & Scott, P., Nat. Med. (2004), doi: 10.1038/nm1108; Sacks, D. L., Nature Immunology (2014), doi:10.1038/ni.2853; Peters N C, PLoS Pathog., 4; 10(12): e1004538, 2014). Previous human cutaneous leishmaniasis cases have used memory response as a surrogate marker for protection (Keshavarz Valian, H. et al., J. Clin. Immunol. (2013), doi:10.1007/s10875-012-9788-7). Further, the increased virulence in the centrin gene addback LmCen$^{-/-}$ AB parasites dampened the innate response similar to that observed with wildtype parasites, demonstrating that the stronger protective immune response to LmCen$^{-/-}$ is associated with the absence of centrin.

Previously, *Leishmania* vaccines were evaluated using mice with healed cutaneous lesions following a low dose of wildtype *L. major* infection as a gold standard animal model that mimics leishmanization in humans (Peters, N. C. et al., Mice. J. Immunol. (2012), doi:10.4049/jimmunol.1201676; Peters, N C et al., Trends Parasitol., 35(6):423-435, 2019; Glennie N D et al., J Exp Med., 24; 212(9):1405-14, 2015). In this example, LmCen$^{-/-}$ parasite immunization induced immunity was also compared with wildtype *L. major* infected, healed mice. The results demonstrated comparable immune responses in mice healed from wildtype infection or immunized with LmCen$^{-/-}$.

Previously, chronic parasite infections were shown to maintain Ly6C$^+$CD4$^+$ effector T cells, and upon challenge with LmWT parasites, the T cells were shown to be essential for IFN-γ production, which mediates protection (Peters N C et al PLOS Pathog 2014). In this example, upon challenge with LmWT parasites, both LmCen$^{-/-}$-immunized and healed mice generated a comparable percentage of CD4$^+$ Ly6C$^+$IFN-γ$^+$ effector T cells. Moreover, upon *L. major* infected sand fly challenge, both groups were protected, and the levels of protection were comparable in parasite burden. These results demonstrate that immunization with LmCen$^{-/-}$ parasites induces both CD4$^+$ central memory and effector responses. The residual parasite burden observed in both ear and lymph nodes in the LmCen$^{-/-}$ may aid in maintaining long-term protection, as shown previously (Peters N C., PLoS Pathog., 4; 10(12):e1004538, 2014; Scott P, Novais F O., Nat Rev Immunol., 16(9):581-92, 2016). However, unlike leishmanization, which involved inoculation with a low-dose of virulent parasites and resulted in lesions at the injection site, immunization with LmCen$^{-/-}$ parasites is safe, as demonstrated by the absence of visible lesions in susceptible and immunodeficient animals post-immunization, despite persistence of a low number of LmCen$^{-/-}$ parasites at the site of inoculation.

Numerous experimental vaccines have been developed for *Leishmania*, but most have not been tested against natural sand fly-transmitted infections. Previously, vaccines were tested by needle challenge versus sand fly transmission of a virulent parasite, and none were protective against the latter (Peters, N. C. et al., PLoS Pathog. (2009), doi:10.1371/journal.ppat.1000484; Peters, N. C. et al., J. Immunol. (2012), doi:10.4049/jimmunol.1201676). The examples herein demonstrate that markerless LmCen$^{-/-}$ immunization induces protection against sand fly-transmitted *L. major*. As mice that had healed from a-low dose infection could mount protection against a sand fly-transmitted infection, immunization with live parasites is an effective vaccination strategy (Peters, N. C. et al., PLoS Pathog. (2009), doi:10.1371/journal.ppat.1000484). The examples show that the major obstacle to using a live vaccine, the risk of disease development, is overcome by a markerless, second-generation live attenuated parasite that can confer protection without any associated pathology, as disclosed herein. Live attenuated LmCen$^{-/-}$ parasites elicited protective immunity in both susceptible (BALB/c) and resistant (C57BL/6) mice and against different strains of *L. major* (WR 2885, FV9, and LV39). These observations using a cutaneous model of infection are consistent with previous publications showing that immunization with LdCen$^{-/-}$ parasites were protective against visceral leishmaniasis in different animal models (Selvapandiyan, A. et al., J. Immunol. (2009), doi:10.4049/jimmunol.0900276; Fiuza, J. A. et al., Vaccine (2013), doi:10.1016/j.vaccine.2013.01.048; Dey, R. et al., J. Immunol. (2014), doi:10.4049/jimmunol.1303145; Banerjee, A. et al., J. Immunol. (2017), doi:10.4049/jimmunol.1700674; Fiuza, J. A. et al., PLoS Negl. Trop. Dis. (2016), doi: 10.1371/journal.pntd.0004322).

Thus, the example embodiments herein show that LmCen$^{-/-}$ parasites are safe and can protect against a sand fly challenge with a wildtype *L. major* infection.

Example 1: Materials and Methods

This example describes methods and materials that can be used in example embodiments of the disclosure.

*Leishmania* strain and culture medium: *L. major* Friedlin (FV9) and *L. major* LV39 used in this study were routinely passaged into the footpads of BALB/c mice. Amastigotes isolated from infected lesions were grown in M199 medium, and promastigotes were cultured at 27° C. in M199 medium (pH 7.4) supplemented with 10% heat-inactivated fetal bovine serum, 40 mM HEPES (pH 7.4), 0.1 mM adenine, 5 mg l$^{-1}$ hemin, 1 mg l$^{-1}$ biotin, 1 mg l$^{-1}$ biopterin, 50 U ml$^{-1}$ penicillin, and 50 μg ml$^{-1}$ streptomycin. Cultures were passaged to fresh medium at a 40-fold dilution once a week. A growth curve of *L. major* promastigotes was obtained by inoculating the parasite at 1×10$^6$/ml into the 96-well plate (150 μl/well) in quadruplicate; OD values were measured once a day for 4 days.

The *L. major* WR 20885 strain was used to infect sand flies. This strain of parasites was isolated from a soldier deployed to Iraq, and the parasites were grown at 27° C. in Schneider's medium supplemented with 10% heat-inactivated FCS, penicillin (100 U/ml), streptomycin (100 μg/ml), and 2 mM 1-glutamine. Compared with other strains, the WR2885 strain exhibits higher colonization and transmissibility by sand flies to mice, resulting in a more severe pathology (for example, larger lesion size and higher parasite loads) (Peters et al., J. Immunol. (2012), doi:10.4049/jimmunol.1201676; Gomes et al., J Invest Dermatol, 132 (12):2735-43, 2012).

CRISPR Plasmid Construction: The pLdCNLm221410a&b plasmid vector was generated as follows. 1) A 276-bp PCR fragment containing gRNALm221410a, hepatitis delta virus, and hammerhead ribozymes as well as gRNALm221410b guide coding sequences was amplified with primers Lm221410a and Ld221410b from a gRNA 241510+MT co-expression vector (Zhang, W.-W., Lypaczewski, P. & Matlashewski, mSphere 2, 1-15 (2017)). The PCR product from step 1 was digested with Bbs I and inserted into the Bbs I digested pLdCN vector (Zhang, W.-W., Lypaczewski, P. & Matlashewski, mSphere 2, 1-15 (2017)) to generate the pLdCNLm221410a&b plasmid vector, which was verified by sequencing analysis.

The guide RNA sequences and oligonucleotide donor used in this example embodiments are listed below, and their locations in the centrin locus are indicated in FIG. 9A.

```
gRNAa (Lm221410a):
                                      (SEQ ID NO: 11)
CTTCTCGCAATCCTTCTGCTGTTTTAGAGCTAGAAATAGCAAGTTAAAAT

AAGGCTAGTCCGTTATCAACTTGAAAAAGTGGCACCGAGTCGGTGCTTTT

TT gRNAb (Lm221410b):
                                      (SEQ ID NO: 12)
TCCGTTGCTTTCCCTCTCAAGTTTTAGAGCTAGAAATAGCAAGTTAAAAT

AAGGCTAGTCCGTTATCAACTTGAAAAAGTGGCACCGAGTCGGTGCTTTT

TT

Oligo donor (Lm221410):
                                      (SEQ ID NO: 3)
5'ATTTCGTGCTTCTCGCAATCCTTCTCAACGGATGATAGTGCG

CGTGTGCG
```

Selection of centrin gene-deleted clones and single cell cloning: *Leishmania* transfections were performed (Zhang, W. W. & Matlashewski, G., Mol. Microbiol., 77, 505-517 (2010). Briefly, 10 μg pLdCNLm221410a&b plasmid DNA was electroporated into 1×10$^8$ early stationary phase *L. major* promastigotes. The transfected cells were then selected with G418 (100 μg/ml) for 2 weeks. Once the transfected *L. major* culture was established, the surviving promastigotes were subjected to three rounds of transfection with the oligonucleotide donor (Lm221410 oligo donor); 10 μl 100 μM single-strand oligonucleotide donor was used per transfection, once every three days. After the third oligonucleotide donor transfection, the *Leishmania* promastigotes were counted and inoculated into 96-well plates at one promastigote per 100 μl medium per well. The growth of *Leishmania* cells in 96-well plates was monitored under microscope. After culture for three weeks in 96-well plates, parasites from the relatively slow-growing clones were expanded in 24-well plates. The slow-growing clones were selected because this represents the phenotype for loss of the centrin gene (Selvapandiyan, A. et al., J. Biol. Chem. (2001), doi:10.1074/jbc.M106806200). The genomic DNA extracted from the slow growth clones was subjected to PCR and DNA sequencing analysis to confirm deletion of the centrin gene.

To remove the pLdCNLm221410a&b plasmid from the centrin gene-deleted *L. major* strain, individual clones were grown in duplicate plates, where one plate contained media with G418, and the duplicate plate contained media without G418. Clones without the plasmid were identified because they could not survive in the presence of G418.

Genome sequence analysis of LmCen$^{-/-}$: Complete genome sequencing of two clones from LmCen$^{-/-}$ was performed using an MiSeq genome sequencing reaction on an Illumina® sequencing instrument (FIGS. 18A-18B). LmCen$^{-/-}$ sequence reads were aligned against *Leishmania major* Friedlin strain reference genome (retrieved from tritrypdb.org) using the Burrows-Wheeler Aligner Maximal Exact Match algorithm (BWA-MEM) (Li, H., arXiv:1303

Figure 2A:
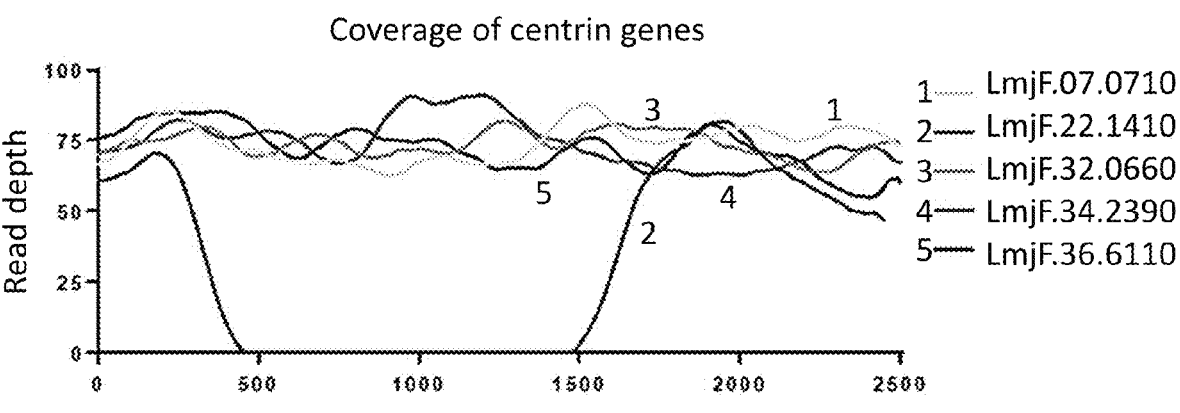

(2013)). The alignments were converted to BED files using samtools and processed using the bedtools software package (Li, H. et al., Bioinformatics 25, 2078-2079 (2009); Quinlan, A. R. & Hall, I. M., Bioinformatics, 26, 841-842 (2010)). The bedtools coverage command was used with the "-d" option in conjunction with the genomic intervals containing the centrin genes to count the read depth at each position in the coverage of centrin genes, which is shown in FIG. 2A with a 200 bp window. The bedtools coverage command was used in conjunction with gene coordinates extracted from a gff genomic annotation file (retrieved from tritrypdb.org) to compute the percent coverage of each gene, as shown in FIG. 2C. Genes with less than 100 percent coverage were manually inspected for a sharp drop-off in coverage (deletion) versus a gradual decline in close proximity to an inverse increase in coverage in a tandem gene (misalignment).

Re-expression of centrin in LmCen$^{-/-}$: The open reading frame encoding centrin gene was cloned into the SpeI sites of the *Leishmania* expression plasmid pKSNeo. LmCen$^{-/-}$ parasites were transfected with the plasmid, and recombinant parasites were selected using 50 μg/ml G418 to obtain LmCen$^{-/-}$ parasites re-expressing the centrin gene, which are referred to herein as LmCen$^{-/-}$ Addback (LmCen$^{-/-}$ AB).

Southern hybridization: Total genomic DNA was isolated from promastigotes with the Wizard genomic DNA purification kit (PROMEGA™ Biosciences). The DNA (5 μg) was digested with restriction enzymes (BglI), and the digestion products were separated on 1% agarose gels and transferred to positively charged nitrocellulose membranes. A Southern blot analysis of the resolved DNA was performed using a $^{32}$p-labeled *L. major* centrin ORF nucleotide sequence as a probe (Gannavaram, S. et al., Sci. Rep. 7 (2017)). The DNA fragments were ligated into pCR2.1-Topo vector, and the nucleotide sequence of the probe was determined to ensure fidelity. The plasmid containing the correct probe was digested with EcoRI, gel purified, and labeled using Random Prime It®-II kit with $^{32}$p-dCTP (Agilent Technologies).

Generation of mCherry expressing parasites: LmWT, LmCen$^{-/-}$, and LmCen$^{-/-}$ AB parasites were transfected with pLEXSY-cherry-Sat2 (Jena Biosciences) plasmid, and recombinant parasite clones stably expressing mCherry fluorescent protein were selected by plating on Nobel agar medium containing nourseothricin.

Generation of LmWT$^{2W}$ and LmCen$^{-/-2W}$ parasites: Wild-type *L. major* (LmWT) and LmCen-parasites expressing 2W1S peptide (EAWGALANWAVDSA; SEQ ID NO: 15) were used to analyze antigen-specific CD4$^{+}$ T cell populations. The 2W1S peptide was fused towards the 3' end of the *L. donovani* 3' nucleotidase/nuclease and expressed using the *Leishmania* expression plasmid pLexsy-Ble2 (Jena Biosciences). The coding sequences containing the 3' nucleotidase/nuclease and 2W (pLexsy-Ble2-2W) peptides were ligated into NcoI and NotI sites of pLexsy-Ble2 vector. *Leishmania* parasites were transfected with 5 μg of SwaI linearized pLexsy-Ble2-2W plasmid DNA. Clones of the recombinant parasites were selected on bleomycin containing Nobel agar plates (Ismail, N., Kaul, A., Bhattacharya, P., Gannavaram, S. & Nakhasi, H. L., Front. Immunol. (2017), doi:10.3389/fimmu.2017.01788). An immunoblot with an α-Ldon 3' nucleotidase antibody confirmed the presence of secreted chimeric protein in the culture supernatants.

Mice infection and immunization: Female 5- to 6-wk-old C57BL/6 and BALB/c mice were immunized and/or infected with 1×10$^6$ total stationary phase LmCen$^{-/-}$ or *L.*

*major* wildtype (LmWT) parasites by intradermal injection in the left ear in 10 W PBS. For challenge infections, age-matched naive and seven-week post-immunized mice (both C57BL/6 and BALB/c) were challenged in the right ear with 750 metacyclic *L. major* (WR 2885 strain) wildtype promastigotes intradermally. The numbers of *L. major* (WR 2885) parasites in the infectious inoculum were determined by a titration analysis revealing that 750 metacyclic parasites cause reproducible pathology in BALB/c mice ear. For leishmanization, mice were infected with 1×10$^4$ metacyclic promastigotes of *L. major* Friedlin (FV9) strain by intradermal needle injection in the ear. After 12 weeks post-infection, healed mice were challenged on the contralateral ear with 1×10$^5$ metacyclic *L. major* wildtype (LmWT) parasites by needle inoculation.

Lesion size was monitored up to 10 weeks post-challenge by measuring the diameter of the ear lesion using a direct reading Vernier caliper. Parasite burden in the challenged ear and draining lymph node (dLN) was estimated using a limiting dilution analysis (Zhang, W. W. & Matlashewski, G., Mol. Microbiol., 77, 505-517 (2010)). Briefly, two sheets of ear dermis were separated; deposited in DMEM containing 100 U/ml penicillin, 100 μg/ml streptomycin, and 0.2 mg/ml Liberase CI purified enzyme blend (Roche Diagnostics Corp.); and incubated for 1-2 h at 37° C. Digested tissue was processed in a tissue homogenizer (Medimachine; Becton Dickinson) and filtered through a 70-μm cell strainer (Falcon® Products). Parasite titrations in the ear and dLN were performed by serial dilution (1:1 dilutions) of tissue homogenates in 96-well flat-bottom microtiter plates (Corning®, Corning, N.Y.) in M199 cell culture media in duplicate and incubated at 26° C. without CO$_2$ for 7-10 days. The greatest dilution yielding viable parasites was recorded, and the data are presented as the mean parasite dilution±SD. For histology, challenged ears were fixed after 10 weeks post-WT parasite infection in fixative solutions (10% buffered formalin phosphate solution), and paraffin-embedded sections were stained with hematoxylin and eosin (H&E) (Histoserv Inc.).

BALB/c mice were immunized subcutaneously in the footpad with 2×10$^8$ LmCen$^{-/-}$ parasites of the Friedlin strain or injected with PBS. After 6 weeks, both groups were challenged with 10$^4$ virulent metacyclics of LV39 *L. major* parasites intra-dermally in the ear. Ear lesions of vaccinated and non-vaccinated mice (PBS group) challenged with *L. major* LV39 metacyclic promastigotes were measured at least once a week from week 1 post-challenge to week 10 post-challenge.

BALB/c, IFN-γ KO and Rag2 KO mice were subcutaneously inoculated with 1×10$^7$ of LmWT (Friedlin V9) or LmCen$^{-/-}$ into the right hind footpad. Following infection, footpad swelling was measured weekly by digital caliper. Parasite burden in the infected footpad was measured at 5 weeks after infection in BALB/c or at 15 weeks in IFN-γ KO and Rag2 KO mice. STAT-1 KO mice were injected subcutaneously in the footpad with 2×10$^8$ LmCen$^{-/-}$ parasites of the Friedlin strain or infected with 2×10$^8$ *L. major* WT parasites of the Friedlin strain. Footpad swelling of both groups was measured at least once a week from week 1 post-injection to week 7. After 7 weeks, both groups were sacrificed, and the parasite burden was determined. Footpad lesions were excised and then homogenized with a cell strainer in 3 ml of Schneider's *Drosophila* medium (Gibco®, US) supplemented with 20% heat-inactivated fetal calf serum and penicillin-streptomycin (0.1%).

Sand fly infection and transmission of *L. major* to immunize mice: Female *Lutzomyia longipalpis* (Jacobina strain)

sand flies were infected by artificial feeding through a chick skin membrane on a suspension of $5\times10^6$ *L. major* (WR 2855 strain) procyclic promastigotes/ml of heparinized defibrinated blood containing penicillin and streptomycin. Flies with mature infections were used for transmission (Kamhawi, S., Belkaid, Y., Modi, G., Rowton, E. & Sacks, D., Science (2000), doi:10.1126/science.290.5495.1351). One day before transmission, the sucrose diet was removed. Mice were anesthetized by intraperitoneal injection of 30 µl of ketamine/xylazine (100 mg/ml). Ointment was applied to the eyes to prevent corneal dryness. Ten infected flies were applied to right ears of both LmCen$^{-/-}$-immunized and age-matched naïve C57BL/6 mice through a meshed surface of vials, which were held in place by custom made clamps. The flies were allowed to feed on the exposed ear for a period of 2-3 h in the dark at 23° C. and 50% humidity. Following exposure, the number of flies per vial with or without a blood meal was counted to determine the influence of feeding intensity on transmission frequency. Animals were sacrificed after 10 weeks post-sand fly exposure, and organ parasite burden was determined by serial dilution as described herein.

Human macrophage infection: Human elutriated monocytes were obtained from healthy blood donors. Only monocytes that tested CMV-negative were used. Monocytes were re-suspended at $2\times10^5$ cells/ml in RPMI medium containing 10% FBS and human macrophage colony-stimulating factor (20 ng/ml, ProSpec), plated at a volume of 0.5 ml in eight-chamber LAB-TEK™ tissue culture slides (Miles Laboratories) and incubated for 7 days for differentiation into macrophages. The differentiated macrophages were infected with stationary phase LmWT or LmCen$^{-/-}$ promastigotes (10:1 parasite-to-macrophage ratio). After incubation for 6 hours at 37° C. in 5% $CO_2$, the free extracellular parasites were removed by RPMI washes, and the cultures were incubated in macrophage culture medium for an additional 24 hours. The culture medium was removed, and macrophages infected with LmWT or LmCen$^{-/-}$ were stained with DIFF-QUIK™ staining reagent. Percentages of infected macrophages were determined by counting a minimum of 100 macrophages per sample under the microscope. Results are shown as mean±SEM for three independent counts for each infection on days 1-8.

Expression of costimulatory molecules in parasitized DCs: Expression of costimulatory signals in parasitized DCs was detected using LmWTmCherry or LmCen$^{-/-}$ mCherry parasites. LmWT parasites that do not express mCherry fluorescent protein were used as control. The mice were intradermally infected with $1\times10^6$ stationary phase LmWTmCherry or LmCen$^{-/-}$mCherry promastigotes. At 48 hours post-infection, the mice were sacrificed, and parasitized DCs (Ly6c$^-$CD11b$^+$ CD11c$^+$mCherry$^+$) from lymph nodes from different groups of mice were analyzed. Single-cell suspensions were prepared from lymph nodes, and RBCs were lysed using ACK lysing buffer. The cells were then labeled with Aqua LD, AF700-α-CD3, BV650-α-CD8a, Pacific blue-α-Ly6c, PerCP-Cy5.5-α-CD11b, PE-Cy7-α-CD11c. CD8a-Ly6c-CD11b$^+$CD11c$^+$mCherry$^+$ DCs from lymph nodes of mice infected with fluorescent parasites were selected on an LSRFORTESSA™ flow cytometer, and the expression of MHCII (APC-Cy7), CD40 (PE-Dazzle594), CD80 (BV605), CD83 (BV711), CD86 (PECy5) on the mCherry$^+$DCs was estimated using FLOWJO™ v10 software.

RT-PCR: The total RNA was extracted from the parasitized DCs using RNAqueous Microkit (Ambion). The total RNA was reverse transcribed into cDNA using random hexamers and a high-capacity cDNA reverse transcription kit (Applied Biosystems). Gene expression was determined using TAQMAN™ Gene Expression Master Mix and pre-made TAQMAN™ Gene Expression assays (Applied Biosystems) with a CFX96 Touch real-time system (Bio-Rad). The data were analyzed with CFX MANAGER™ software. The TAQMAN™ Gene Expression Assay ID (Applied Biosystems) of different primers used was as follows: IL-12 (Mm00434174); IL-6 (Mm00446190) and GAPDH (Mm99999915). Expression values were determined using the $2^{-\Delta\Delta Ct}$ method in which samples were normalized to GAPDH expression.

Expression of central memory markers in CD4$^+$ T cell populations: Mice were immunized with $3\times10^6$ LmWT- or LmCen$^{-/-}$-expressing 2W1S peptide (LmWT2W, LmCen$^{-/-}$ 2W) via intradermal injection in the left ear. Age-matched naïve mice were used as a negative control. In each study, at least 4 mice were used per group. At each experimental time point, spleens, inguinal, axillary, superficial cervical, submandibular, and parotid lymph nodes were collected. Single cell suspensions from these organs were used to enrich for 2W-specific CD4$^+$ T cells using tetramer reagents on Miltenyi LS columns. Enriched cells were labeled and analyzed using flow cytometry. 2W1S: I-A$^b$-streptavidin-phycoerythrin (2W-PE) tetramers were obtained.

Enrichment of specific CD4$^+$ T cell populations by flow cytometry: Tetramer staining was performed following the published protocol (Fiuza, J. A. et al., PLoS Negl. Trop. Dis. (2016), doi:10.1371/journal.pntd.0004322). Cell suspensions were treated with 3 ml of ACK lysis buffer for 5 min at RT. After washing, the cells were stained with 2W-PE tetramers for 1 h in the dark at RT. The cells were labeled with α-PE magnetic beads for 30 minutes on ice. Epitope-specific CD4$^+$ T cells were enriched on Miltenyi LS magnetic columns (Sacks, D. L., Nature Immunology (2014), doi:10.1038/ni.2853). The cells were stained with surface markers on ice with conjugated α-B220, α-CD11b, α-CD11c, and α-F4/80 all conjugated with eFluor 450; AF700-α-CD3, BV785-α-CD4, BV650-α-CD8a, FITC-α-CD44, BV605-α-CD62L, PE-Cy7-α-IL7R and PerCP-Cy5.5-α-CCR7. The cells were then analyzed using an LSRFORTESSA™ (Becton Dickinson). The data were analyzed using FLOWJO™ software v10 (TreeStar).

Image stream analysis: Sort-selected parasitized DCs were evaluated using an imaging flow cytometer (ImageStream®, Amnis®, Seattle, USA), acquiring 5000 images in the bright field channel and the fluorescence emission channels at 577 nm (mCherry), 610 nm (PE-Dazzle 594-CD40), and 762 nm (APC-Cy7-MHCII) for each sample. The acquired images were analyzed using IDEAS® software (Amnis®). A scatter plot of the aspect ratio/area was used to gate for single cells. Image analyses were performed to determine the expression of CD40 and MHCII on the mCherry-expressing and non-mCherry-expressing parasitized DCs.

Measurement of cytokine expression from ear-derived CD4$^+$ T cell populations by flow cytometry: To determine the comparative immune response at pre- or 20 hours-post-*L. major* WT needle challenge, single-cell suspensions from ears of the healed (leishmanized) and LmCen$^{-/-}$-immunized mice were incubated with $1\times10^6$ T cell-depleted (Miltenyi Biotech) naïve spleen cells (APCs) with 50 µg/ml freeze-thaw *L. major* antigen (LmAg) in flat bottom 48-well plates at 37° C. for 12-14 hours. During the last 4 hours of culture, a protein transport inhibitor (BD GOLGIPLUG™, BD Biosciences) was added to the wells. The cells were then blocked at 4° C. with rat α-mouse CD16/32 (5 µg/ml) from BD BioSciences for 20 minutes. For surface staining, the cells were then stained with α-mouse CD3 AF-700 (BD BioSciences), α-mouse CD4 BV-650 (Biolegend®), and α-mouse CD44 FITC (BD BioSciences) or α-mouse CD3 BV421 (BD BioSciences), α-mouse CD4 BV-650 (Biolegend®), α-mouse Ly-6C APC-Cy7 (BD BioSciences), and α-mouse CD44 FITC (BD BioSciences) for 30 minutes (each with 1/300 dilution; 4° C.). The cells were then stained with LIVE/DEAD fixable aqua (Invitrogen®/Molecular Probes®) to stain dead cells. Cells were washed with wash buffer and fixed with the CYTOFIX/CYTOPERM™ Kit (BD Biosciences) for 20 minutes (room temperature). Intracellular staining was performed with α-mouse IL-2 APC (BD BioSciences), α-mouse IFN-γ PE-Cy7 (Biolegend®), and α-mouse TNF-α PerCP-Cy5.5 (Biolegend®) α-mouse IL-2 APC (BD BioSciences) for 30 min (each with 1:300 dilution; 4° C.). In some experiments samples were treated with Foxp3 Fixation/Permeabilization Buffer (EBIOSCI-ENCE™) and then stained with α-mouse T-bet-BV786 (Biolegend®) according to the manufacturer's instructions. Cells were acquired using a FACSYMPHONY™ (BD Biosciences, USA) analyzer equipped with 350, 405, 445, 488, 561, 638, and 785 nm LASER lines using FACSDIVA™ software (v8). The data were analyzed using the FLOWJO™ software version 9.9.6 (BD, San Jose Calif.). For analysis, the first doublets were removed using the width parameter; dead cells were excluded based on staining with the Live/Dead® Aqua dye. Lymphocytes were identified according to their light-scattering properties. CD4+ T-cells were identified as CD3+ lymphocytes uniquely expressing CD4. Upon further gating, intracellular cytokines were measured in CD44$^{hi}$Ly-6C+T-bet+ cells. Fluorescence minus one control was used for proper gating of positive events for the designated cytokines.

Measuring cytokines by ELISA: C57BL/6 mice were injected with $1\times10^6$ stationary-phase promastigotes of LmWT or LmCen$^{-/-}$ intradermally into the ears. At 3 weeks post-infection, ear draining lymph nodes were isolated, and cells were cultured at $5\times10^5$ cells per well in 96-well culture plates in 200 μl RPMI medium (supplemented with 10% heat-inactivated fetal bovine serum, 100 U/ml penicillin, and 100 μg/ml streptomycin). After 72 hours of culture with or without crude *Leishmania* antigen, culture supernatants were collected and stored at −30° C. Concentrations of IFN-γ and TNF-α were measured using a sandwich ELISA per the manufacturer (R&D Systems®) instructions.

Immunosuppression by dexamethasone injection: To determine the safety of centrin-deficient LmCen$^{-/-}$ parasites under immune-suppressive conditions, 4- to 6-week-old BALB/c mice were divided into three groups. Group-1 (n=6) was infected with $1\times10^6$ stationary-phase LmWT parasites; Group-2 (n=6) and Group-3 (n=12) animals were immunized with $1\times10^6$ stationary-phase LmCen$^{-/-}$ parasites in a 10 μl volume of PBS through intradermal (into the ear dermis) routes. After 10 weeks post-infection, only Group-3 animals were treated with 2 mg/kg Dexamethasone sodium phosphate (Sigma Aldrich) in PBS by subcutaneous injection three times for one week. Four weeks after this treatment (total 15 weeks post-infection), all of the groups were sacrificed and evaluated for parasite burden by serial dilution, as described herein Development of pathology and lesion size in the ear was assessed at 15 weeks post-infection by measuring the diameter of the lesion.

Characterization of centrin-deleted parasites isolated from the LmCen$^{-/-}$ plus DXM-treated group was performed using polymerase chain reaction (PCR). The total genomic DNA was isolated from the parasites recovered from the LmWT and LmCen$^{-/-}$ plus DXM-treated group according to the manufacturer's information (DNeasy® Blood & Tissue Kit, Qiagen®). Polymerase chain reaction was performed using a *L. major* centrin gene-specific primer (For-5'-ATGGCTGCGCTGACGGATGAACAGATTCGC-3' (SEQ ID NO: 6); Rev-5'-CTTTCCACGCATCTGCAGCAT-CACGC-3' (SEQ ID NO: 7)), which targets amplification of 450-bp. A reaction mixture was prepared, which contained 10×Buffer (Invitrogen), 0.2 mmol/l each deoxyribonucle-otide (Invitrogen®), 1 μmol/l each primer, 1.25 units of Taq polymerase (Invitrogen®), and 200 ng of DNA samples in a final volume of 50 μl. The PCR conditions were as follows: denaturation at 94° C. for 3 minutes followed by 35 cycles of 94° C. for 20 s, 58° C. for 20 s, and 68° C. for 35 s with a final extension of 68° C. for 5 minutes. The amplification reactions were analyzed using 1% agarose gel electrophoresis followed by ethidium bromide staining and visualization under UV light. DNA from the reference plasmid (PCR 2.1 TOPO) containing the centrin gene was used as a positive control.

Statistical analysis: Statistical analysis of the differences between means of groups was determined using the unpaired two-tailed Student's t test with the GraphPad Prism 5.0 software. In the examples, *p<0.05, p<0.005, and *p<0.0005 were considered significant.

Example 2: Results

Generation and selection of centrin-deficient *L. major* (LmCen$^{-/-}$) by CRISPR-Cas: CRISPR-Cas genome editing was used to delete *Leishmania* genes with or without integration of antibiotic selection markers into the genome (Zhang, W. W. & Matlashewski, G., MBio 6, e00861-15 (2015); Zhang, W.-W., Lypaczewski, P. & Matlashewski, G., mSphere 2, 1-15 (2017)). The experimental approach used to delete the centrin gene (Gene ID: LmjF.22.1410) from *L. major* is detailed in FIGS. 1A-1B. Two guide sequences targeted to the 5' and 3' flanking sequences of the centrin gene were designed and cloned into the *Leishmania* CRISPR vector pLdCNa&b (Zhang, W. W. & Matlashewski, G., MBio 6, e00861-15 (2015), FIG. 1A) and transfected into *L. major* (Friedlin V9) promastigotes. To delete the centrin gene sequence precisely at the locations determined by the 2 guide RNA sequences flanking the centrin gene without using marker gene replacement, a 50-nucleotide oligonucleotide donor DNA sequence was transfected into the promastigotes containing the CRISPR expression vector pLdCN (Zhang, W.-W., Lypaczewski, P. & Matlashewski, G., mSphere 2, 1-15 (2017)). The donor DNA consisted of 25 nucleotides 5' from the upstream gRNAa cleavage site and 25 nucleotides 3' from the downstream gRNAb cleavage site (FIG. 1B). The exact targeted sequences flanking the centrin gene and diagnostic PCR primers are shown in FIG. 9A.

Figure 9C:
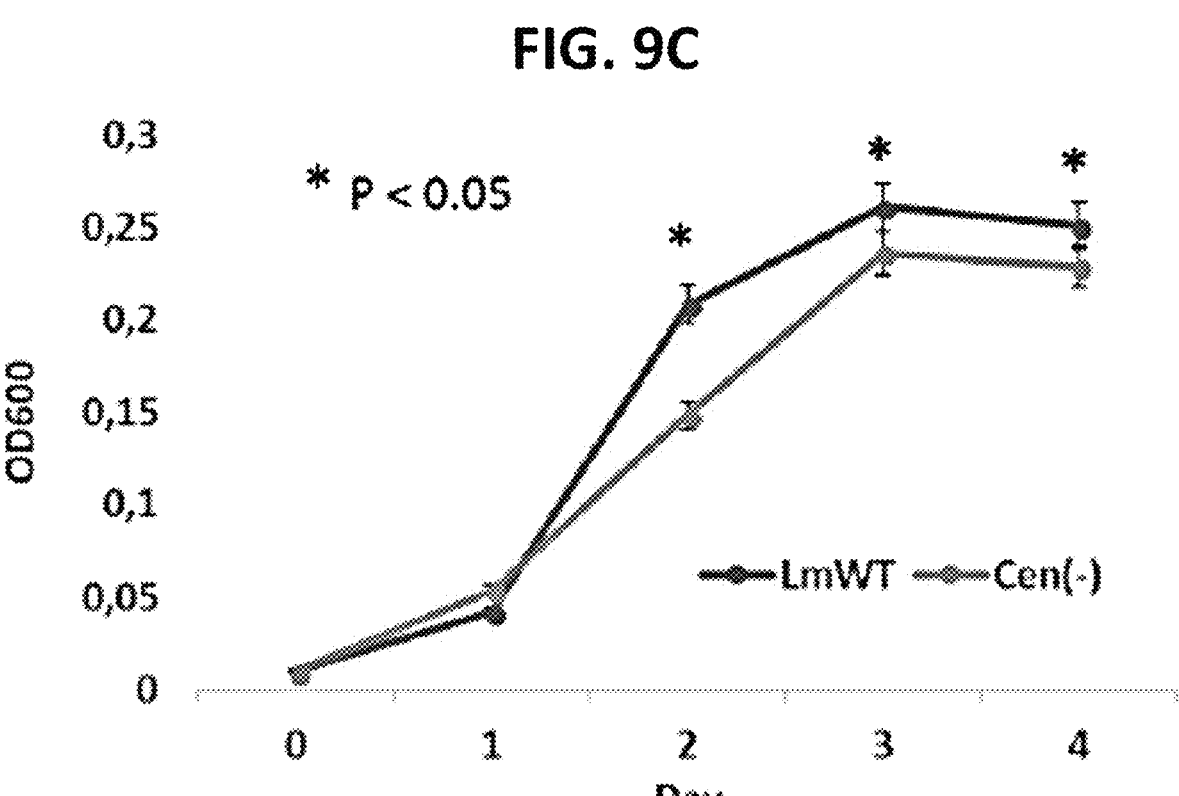

*L. donovani* centrin-null promastigotes proliferate slower than wildtype promastigotes (Selvapandiyan, A. et al., J. Biol. Chem. (2001), doi:10.1074/jbc.M106806200). Because centrin-null promastigotes were selection-marker-free, this slower proliferation phenotype was used to identify centrin null *L. major* promastigotes. The CRISPR-genome-edited *L. major* promastigotes were subjected to single-cell cloning in 96-well plates; the relatively slow-growing clones were identified, expanded, and subjected to PCR analysis with the primers flanking the centrin gene, as shown in FIG. 1B. An example of PCR analysis for a slow-growing clone with the loss of the centrin gene is shown in FIG. 1C. A sequence analysis of the 604-bp PCR product shown in FIG. 1C confirmed that the centrin gene-containing sequence was precisely deleted at the predicted gRNA target sites, and the chromosome was fused through the donor sequence, as intended (FIG. 1D). The gRNA/Cas9-expressing pLdCN plasmid was subsequently removed from the $L.$ $major$ centrin-null mutant (LmCen$^{-/-}$) using single-cell cloning and maintaining replica cultures in the presence and absence of G418 to identify clones sensitive to G418 without the neomycin resistance gene present in the pLdCN CRISPR gene-editing plasmid. Plasmid DNA from the G418-sensitive LmCen$^{-/-}$ parasite could not be amplified, further demonstrating loss of the pLdCN plasmid (FIG. 9B). Also shown in FIG. 9C, the LmCen$^{-/-}$ parasite retained the phenotype of slower proliferation compared with the WT $L.$ $major.$ This difference in proliferation facilitated identification and isolation of the slower growing centrin gene-deleted clones using visual and microscopy examination of the 96-well plate after one week in culture.

LmCen$^{-/-}$ promastigotes failed to produce lesions in infected mice: Whether the LmCen$^{-/-}$ lost the ability to cause cutaneous infections and whether adding back the centrin gene through plasmid transfection (add-back, LmCen$^{-/-}$AB) could restore cutaneous infection was examined. The centrin gene was inserted into the $Leishmania$ pKSNeo expression plasmid (Zhang, W. W., Charest, H. & Matlashewski, G., Nucleic Acids Res. (1995), doi:10.1093/ nar/23.20.4073; Zhang, W. W. & Matlashewski, G., Mol. Microbiol. 77, 505-517 (2010)) and transfected into LmCen$^{-/-}$ promastigotes; expression of the centrin protein was confirmed by western blotting using an α-LdCen antibody that recognizes $L.$ $major$ centrin (FIG. 1E). LmCen$^{-/-}$ infection was investigated following intradermal injection of $1 \times 10^6$ stationary phase promastigotes in the ear of C57BL/6 mice. As shown in FIG. 1F, LmCen$^{-/-}$ failed to produce swelling in the infected ear by 5-6 weeks, whereas wildtype $L.$ $major$ (LmWT) Friedlin V9 and the LmCen$^{-/-}$ with the add-back centrin gene (LmCen$^{-/-}$ AB) induced significant swelling. At 6 weeks following infection, the LmCen$^{-/-}$-infected mice had few (<10) detectable parasites compared to both the LmWT- and LmCen$^{-/-}$ AB-infected mice, both of which had significantly more parasites (~$2 \times 10^6$) (FIG. 1G). These observations confirm that at 6 weeks post-infection, marker-free LmCen$^{-/-}$ is unable to induce pathology at the site of injection in mice due to deletion of the centrin gene.

Figure 9D:
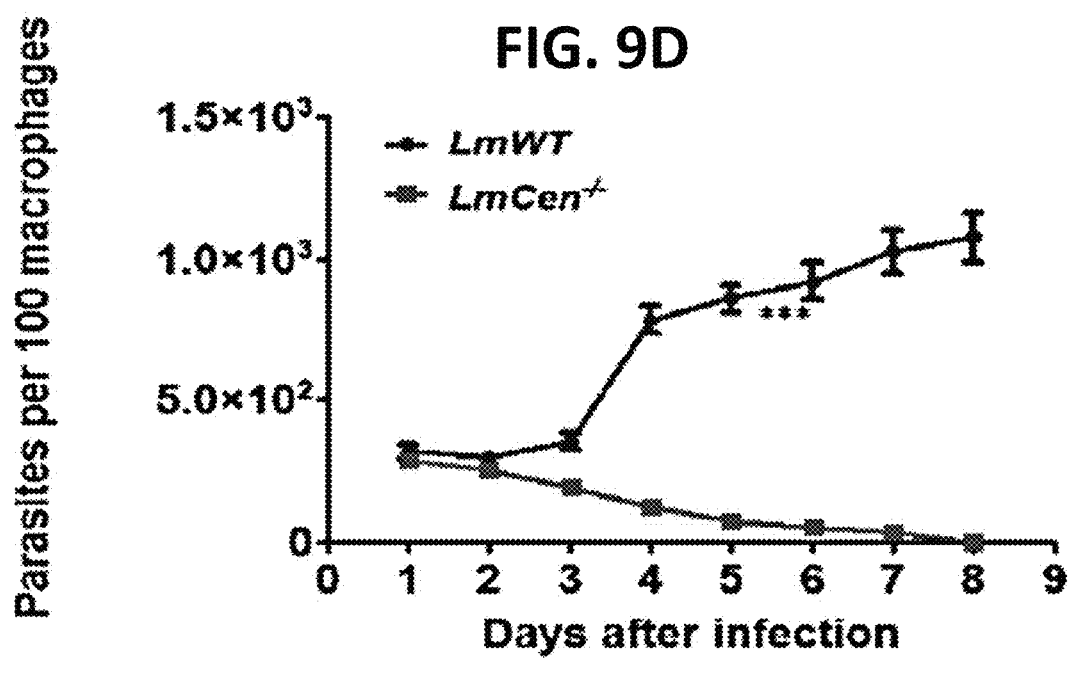

Next, LmCen$^{-/-}$ survival was examined in human macrophages in vitro because they are the obligate host cells for intracellular replication of $Leishmania$ amastigotes (FIG. 9D). At 24 hours post-infection, the number of parasites per macrophage was similar in the LmCen$^{-/-}$ and LmWT-infected cells. However, LmCen$^{-/-}$ amastigotes were cleared from the macrophages by 8 days, whereas LmWT parasites reached >10 parasites/macrophage. These results demonstrate that the LmCen$^{-/-}$ promastigotes effectively infected human macrophages but, subsequently, were unable to intracellularly proliferate.

Figure 2B:
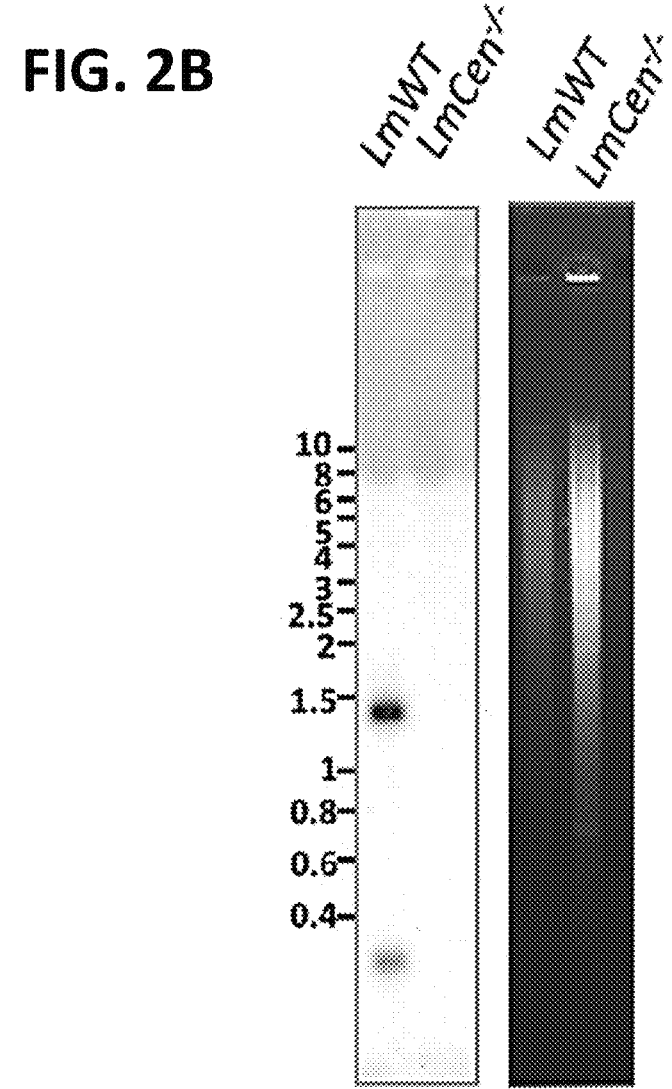
Figure 2C:
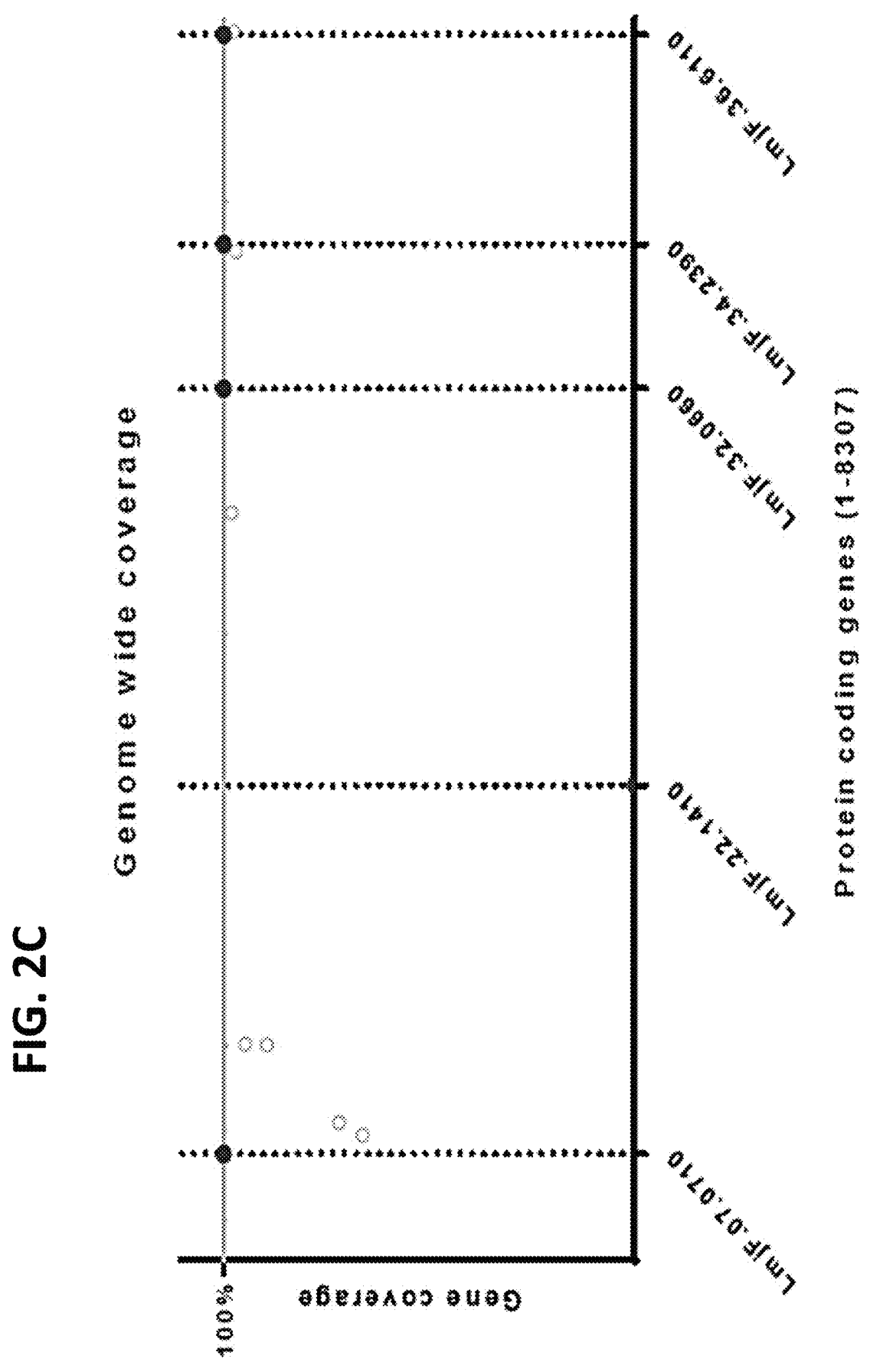

LmCen$^{-/-}$ contains no off-target gene deletions: Because the CRISPR generated LmCen$^{-/-}$ strain was attenuated, the integrity of the genome was established using a whole genome sequencing analysis to confirm that attenuation was solely due to removal of the centrin gene. This analysis confirmed that the targeted ~1 kb genome region containing the 450 bp centrin gene (ID:LmjF.22.1410) was deleted from chromosome 22, and the remaining centrin gene homologs on chromosomes 7, 32, 34, and 36 remained intact in the genome (FIG. 2A). Southern blot analysis confirmed that the targeted centrin gene in LmCen$^{-/-}$ was deleted and not translocated to another region of the genome (FIG. 2B). Whole genome sequencing was performed to determine whether there were any off-target gene deletions in the edited genome. As shown in FIG. 2C, the blue line includes over 8,000 circles, each circle representing a single gene from chromosome 1 through 36 (left to right), whereas the red circles represent members of the centrin gene family located on chromosomes 7, 22, 32, 34, and 36. Approximately 100% coverage was obtained for all 8307 genes in the genome, indicating the absence of partial or complete gene deletions, except for the targeted centrin gene (LmjF.22.1410), which showed 0% coverage due to deletion through CRISPR gene editing. A handful of genes with less than 100% coverage are tandem repeat genes for which the coverage calculation software misaligned some reads; these genes were manually inspected and were found intact. Compared with the $L.$ $major$ Friedlin reference genome, the genome contained no indels, and 20 genes included nonsynonymous SNPs that were all natural variants previously identified in other $L.$ $major$ strains. This example demonstrates that the LmCen$^{-/-}$ genome is intact and produces no off-target gene mutations.

Figure 2D:
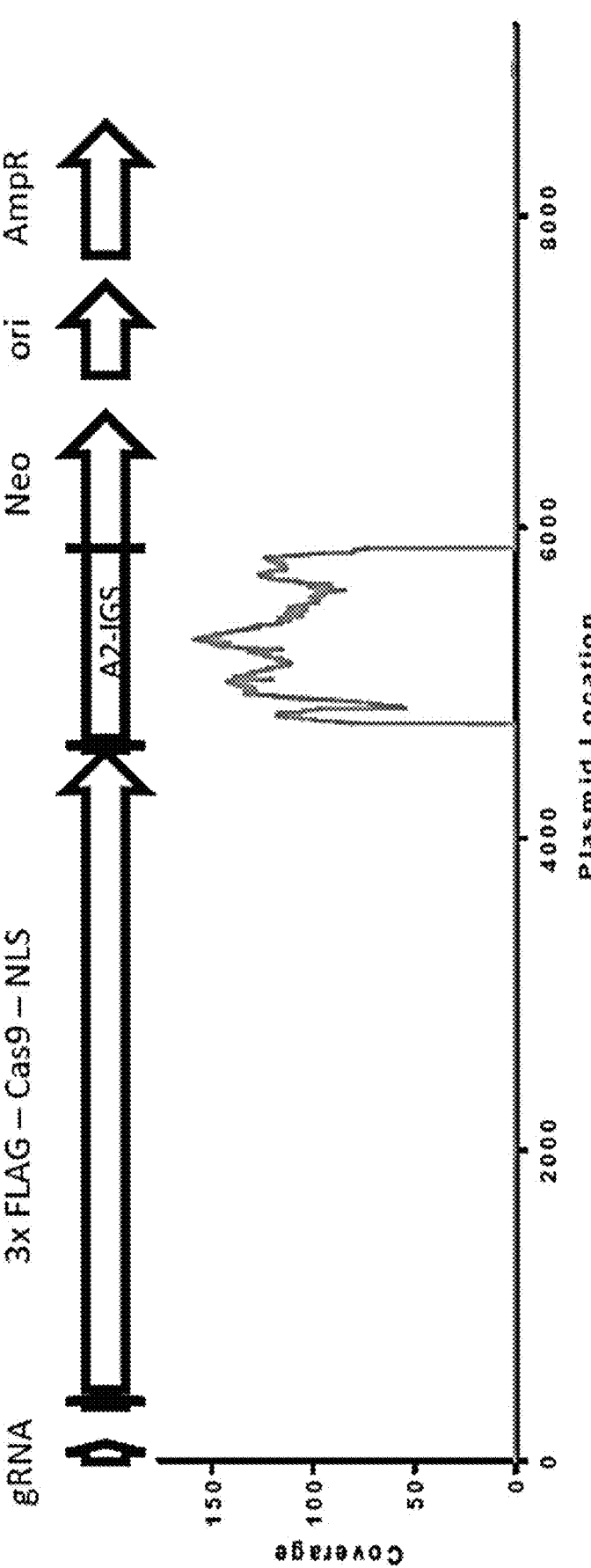

The genomic DNA sequence reads were also searched for the presence of pLdCN CRISPR plasmid DNA sequences to confirm loss of this plasmid. As shown in FIG. 2D, the only LmCen$^{-/-}$ genomic DNA sequences in common with the pLdCN CRISPR plasmid is the A2 gene intergenic sequence (A2-IGS), which is part of a A2 pseudogene sequence in the $L.$ $major$ genome. The A2-IGS sequence from $L.$ $donovani$ was engineered into the pLdCN CRISPR plasmid to process the Neo$^R$ gene transcript (Zhang, W. W. & Matlashewski, G., MBio 6, e00861-15 (2015)). There were no other detectable plasmid sequences or antibiotic resistance genes in the genome of LmCen$^{-/-}$. It is noteworthy that the $L.$ $donovani$ ribosomal RNA promoter (rRNAP) sequence in the pLdCN CRISPR plasmid is sufficiently divergent from the $L.$ $major$ rRNAP sequence that it was not identified in the MiSeq DNA sequences by the Maximal Exact Match (bwa-mem) sequence alignment algorithm used. Taken together, the results presented in FIG. 2D and FIG. 9B in combination with the loss of G418 resistance demonstrate that the pLdCN CRISPR gene-editing plasmid is no longer present in LmCen$^{-/-}$. LmCen$^{-/-}$ is the first marker-free gene deleted $Leishmania$ strain to be generated in a laboratory.

Figures 3C, 3D:
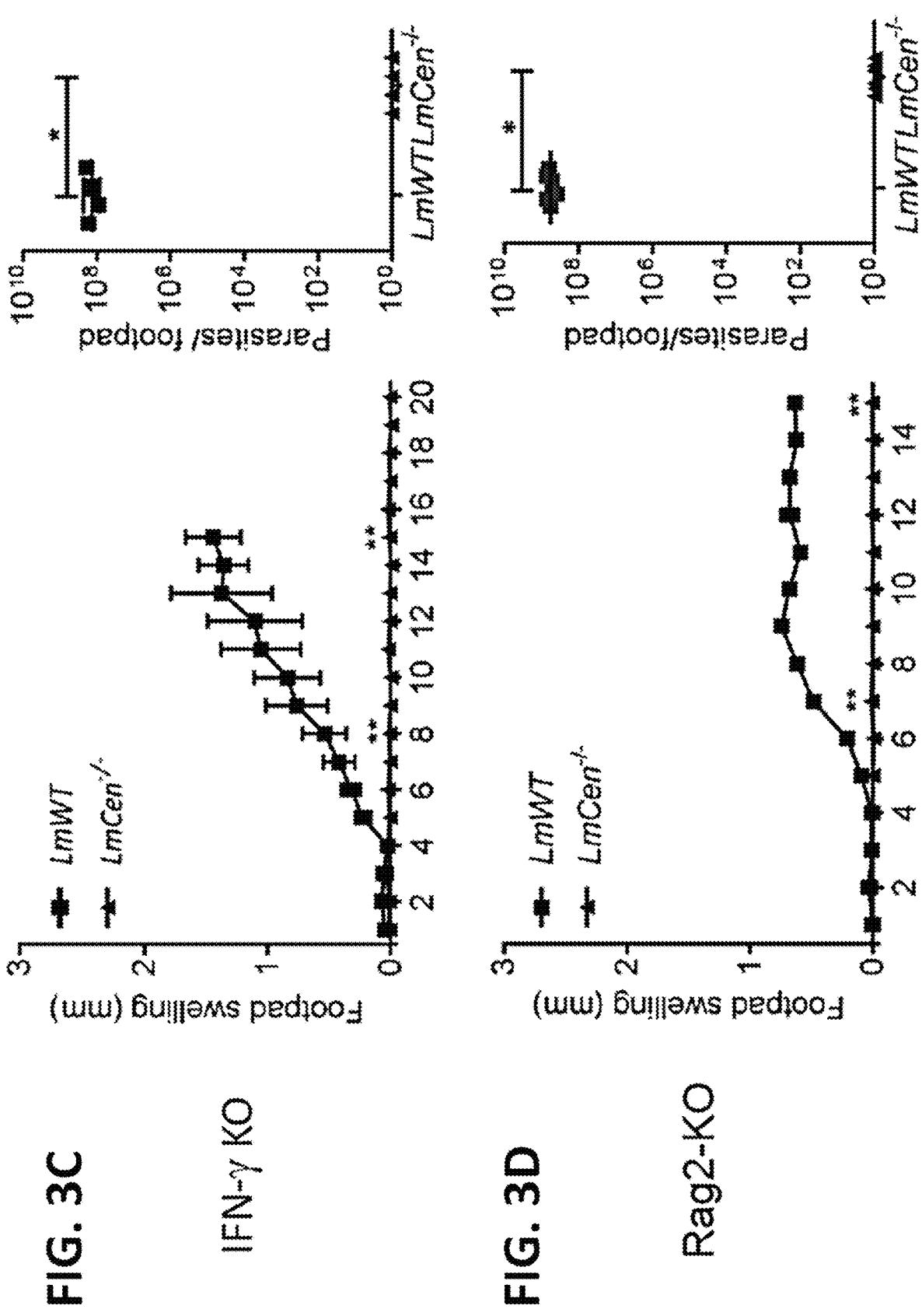
Figure 10B:
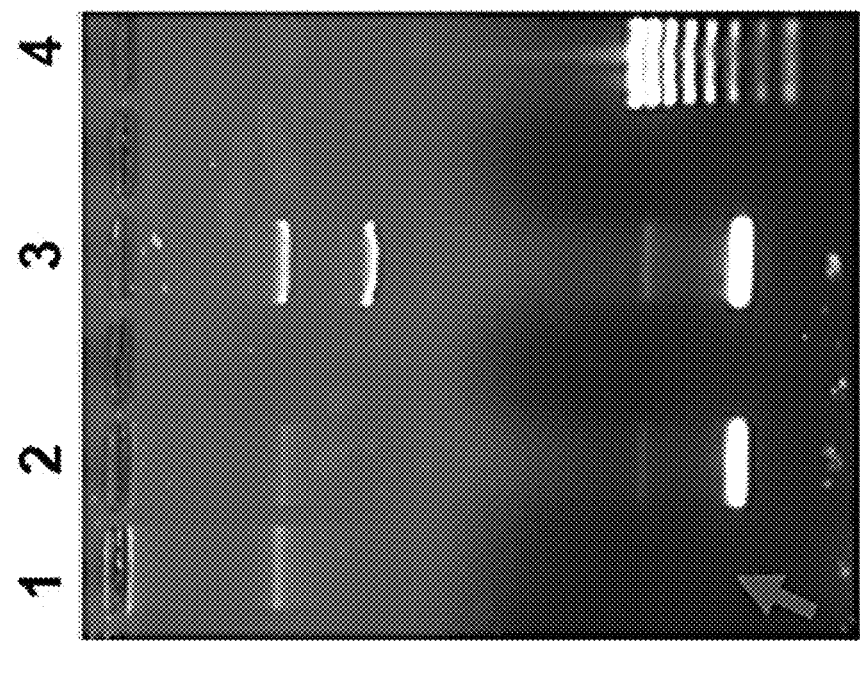
FIGS. 10A-10D show safety and non-pathogenicity.
Figure 10A:
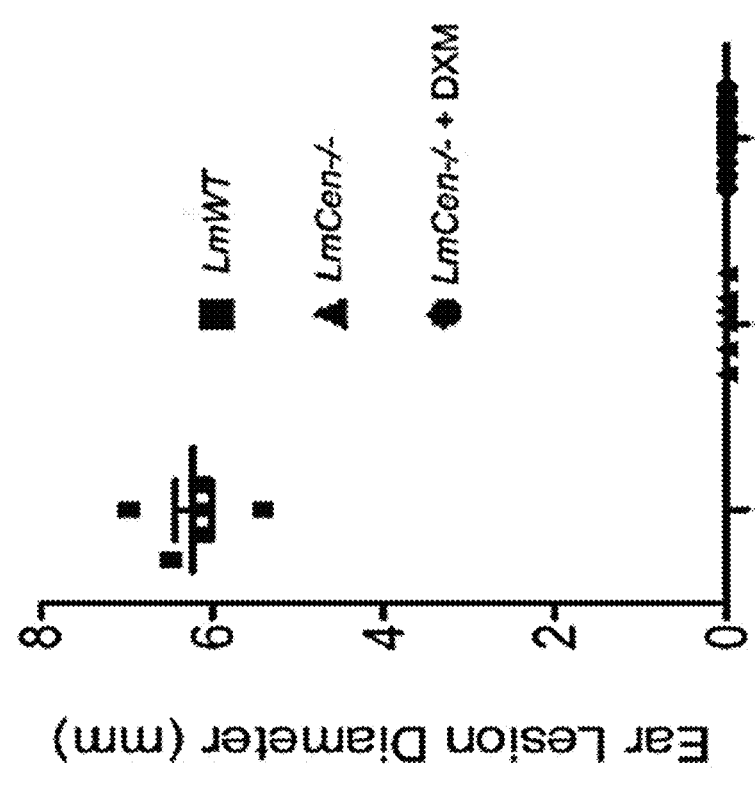
Figures 10C, 10D:
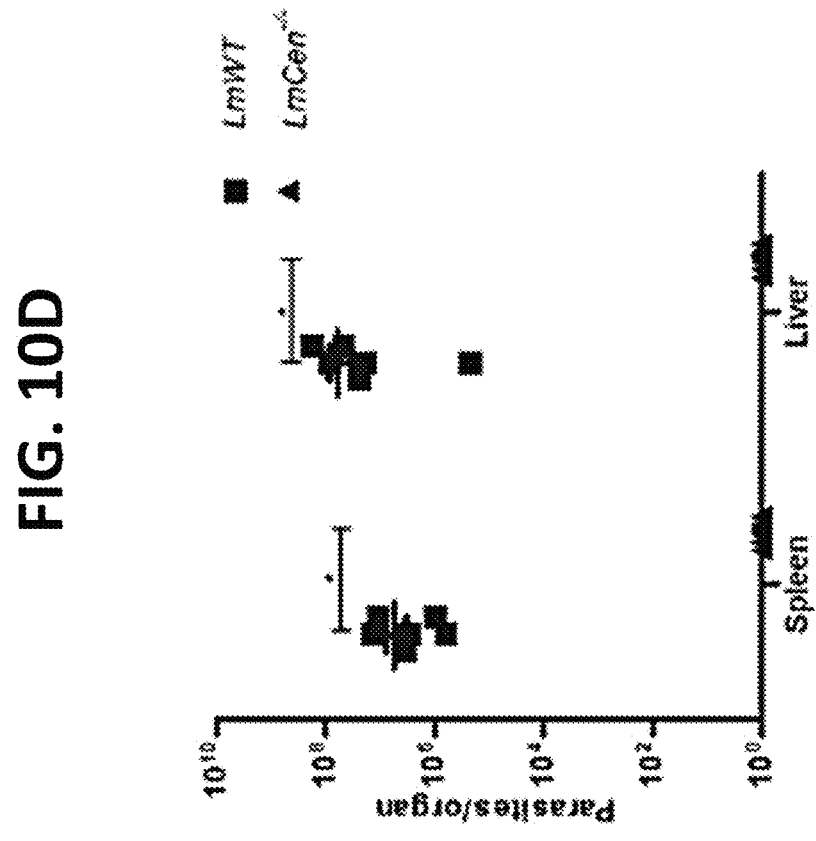

Immunization with live LmCen$^{-/-}$ is safe and does not cause lesions in highly susceptible mice: As shown in FIG. 1F, LmCen$^{-/-}$ was unable to induce ear cutaneous lesions in C57BL/6 mice due to the removal of the centrin gene. However, to assess the safety of LmCen$^{-/-}$ as a potential live vaccine, it was necessary to investigate its attenuation in a more susceptible mouse strain (BALB/c) and in immune deficient mice. BALB/c mice injected subcutaneously in the footpad with $1 \times 10^7$ stationary phase LmCen$^{-/-}$ showed no footpad swelling over 20 weeks (FIG. 3A), the study endpoint, and a significantly lower parasite burden (approximately 4 log-fold reduction) as compared to BALB/c mice injected with LmWT (FIG. 3A). In some animals, LmCen$^{-/-}$ parasites were completely cleared by the study end point. Likewise, STAT-1 KO immune-deficient mice injected with $2 \times 10^8$ LmCen$^{-/-}$ stationary phase parasites showed no footpad swelling during the 7 weeks following injection (FIG. 3 B), whereas footpad swelling started at 4 weeks after injection with LmWT (FIG. 3B). The parasite burden at 7 weeks in STAT-1 KO mice injected with LmWT was significantly higher than the mice injected with LmCen$^{-/-}$ attenuated parasites (approximately 6 log-fold reduction, FIG. 3B). In another test, IFN-γ KO mice showed severe footpad swelling accompanied by a drastic increase in the number of the parasites after injection with $1 \times 10^7$ LmWT, while injection with the same dose of LmCen$^{-/-}$ did not show footpad swelling in 20 weeks, and the parasites were cleared from the site of injection (FIG. 3C). The recombination activating gene 2 deficient (Rag2 KO) mice, which lack conventional T cells and B cells, showed mild footpad swelling and a high parasite burden in the footpad after 15 weeks following injection with LmWT (FIG. 3D). In contrast, injection with LmCen$^{-/-}$ did not show swelling (FIG. 3D; FIG. 10C), and the parasites were cleared from the site of injection (FIG. 3D) as well as the spleen and liver (FIG. 10D). These results demonstrate that LmCen$^{-/-}$ is non-pathogenic even in highly immunocompromised mice.

To rule out the survival of any undetectable LmCen$^{-/-}$ parasites beyond 7 weeks post-immunization, LmCen$^{-/-}$ infected BALB/c mice were treated with 2 mg/kg dexamethasone (DXM), a known immune suppressor, three times for a week starting at 10 weeks post-infection (FIG. 3E). All the groups were sacrificed at 4 weeks after the DXM treatment to determine parasite burdens. As shown in FIG. 3F and FIG. 10A, LmCen$^{-/-}$-infected mice with or without DXM treatment resulted in no lesions, while LmWT-infected, but DXM-untreated mice developed open ulcerative lesions in the ear. Moreover, only 2 of 12 DXM-treated mice infected with LmCen$^{-/-}$ showed parasites in the inoculated ear (FIG. 3G) and draining lymph node (FIG. 3H). In 1 of 6 untreated LmCen$^{-/-}$-immunized animals, a low parasite number was detected in the draining lymph node (<100 parasites, FIG. 3H), and none in the ear (FIG. 3G). In LmWT infected mice, a significantly higher parasite load was observed in the ear and draining lymph node compared with LmCen$^{-/-}$-infected mice (±DXM) (FIGS. 3G and 3H), which correlated with ear lesion size (FIG. 3F). Further, a PCR analysis using L. major centrin gene-specific primers confirmed the absence of the centrin gene in the parasites isolated from DXM-treated mice (FIG. 10B, lane 1, red arrow). The results demonstrate that centrin-deleted live LmCen$^{-/-}$ parasites are unable to revert or cause pathology and are safe as a live vaccine.

Figure 4E:
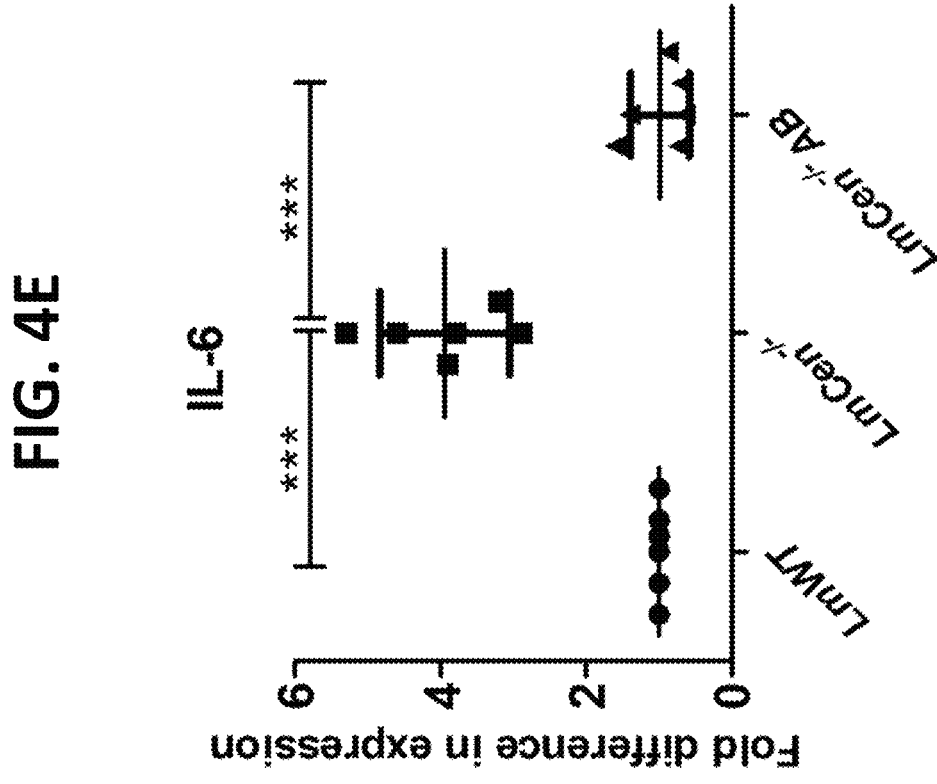
Figure 12A:
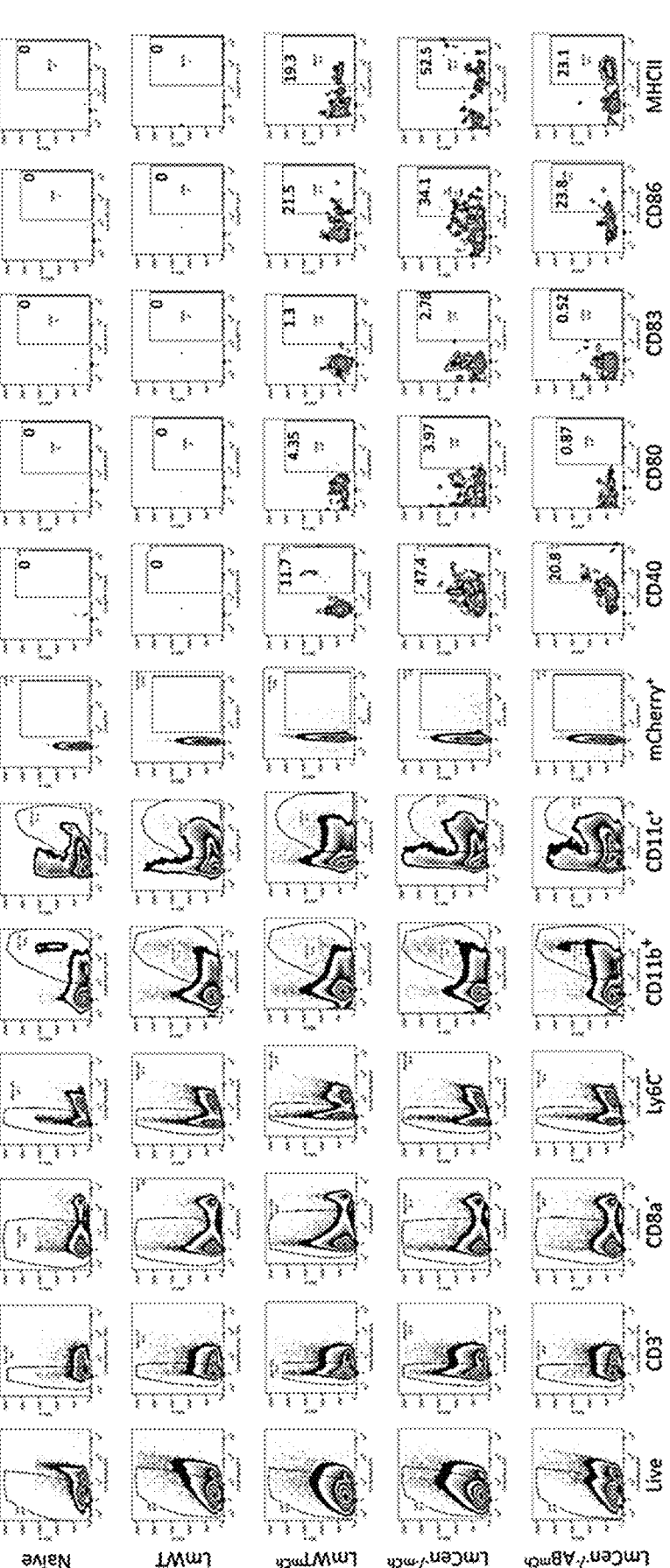
Figures 12B, 12C:
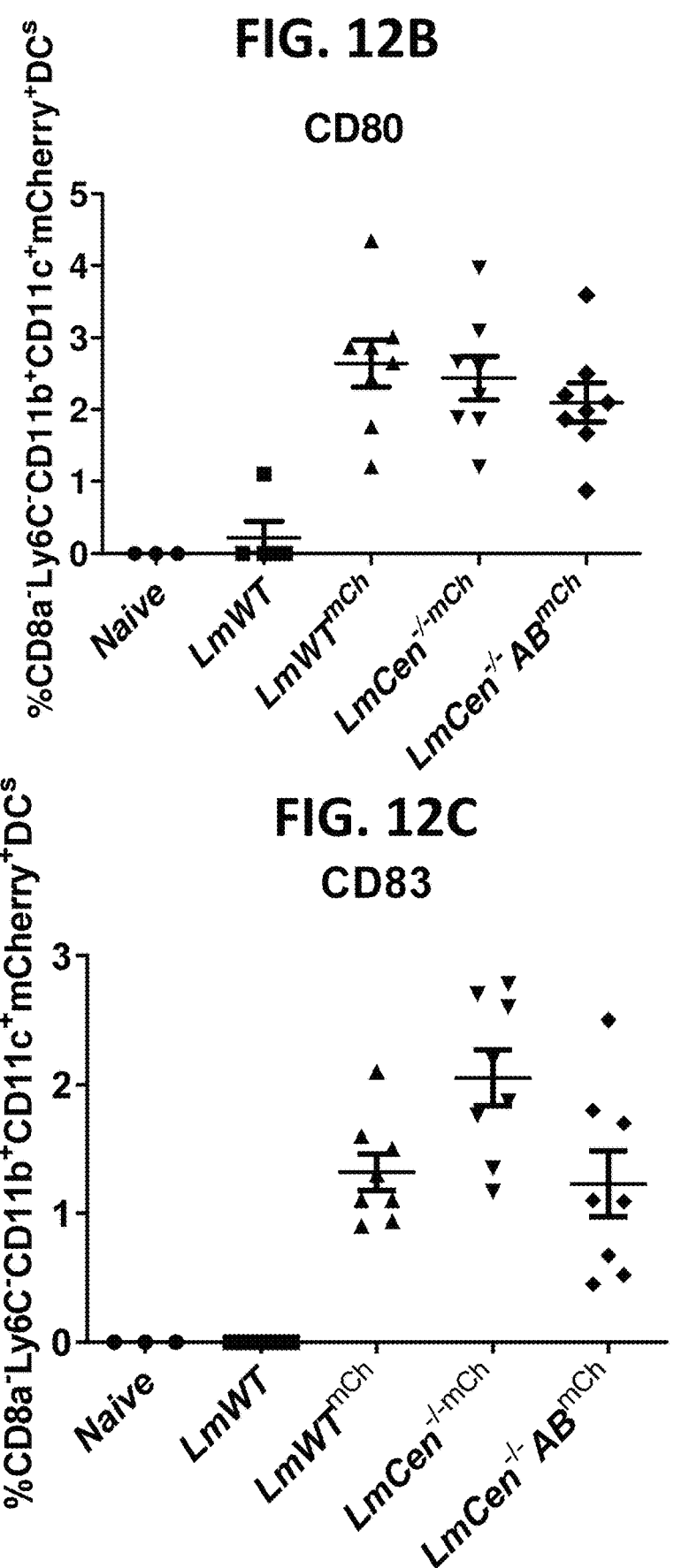
Figure 12D:
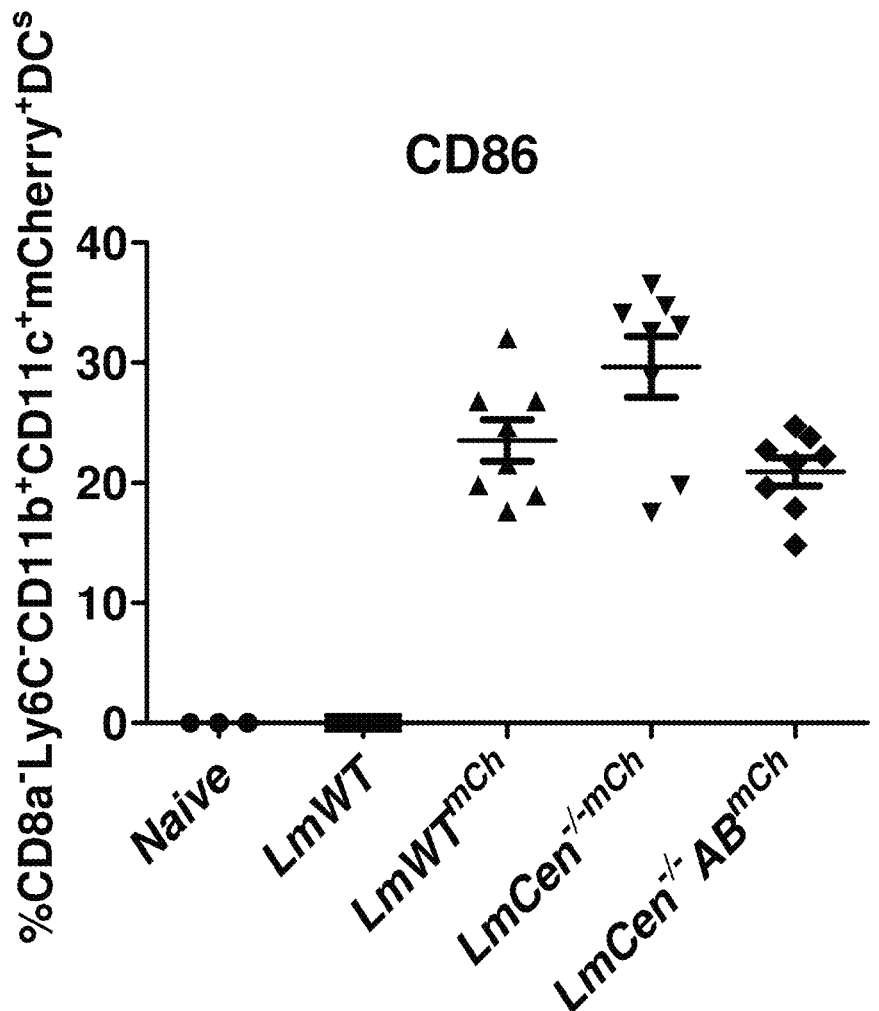

LmCen$^{-/-}$ are immunogenic and induce a robust memory response: Initially, the early innate immune response induced by injection of LmCen$^{-/-}$ was investigated. C57BL/6 mice were infected with LmWT, LmCen$^{-/-}$ and LmCen$^{-/-}$ AB parasites stably expressing the mCherry fluorescent protein (FIG. 4A), and parasitized DCs were identified 48 hours post-infection by flow cytometry (FIG. 12A). LmWT parasites not expressing mCherry fluorescent protein were used as controls. Ly6C$^-$CD11b$^+$CD11c$^+$mCherry$^+$ DCs isolated from draining lymph nodes of LmCen$^{-/-mCherry}$-infected mice showed significantly higher levels of CD40 (FIG. 4B) and MHCII (FIG. 4C) expression compared with those isolated from LmWT$^{mCherry}$-infected mice. The higher level of induction of CD40 and MHCII expression was abrogated in DCs obtained from LmCen$^{-/-}$AB$^{mCherry}$-infected mice (FIGS. 4B-4C). The expression of other co-stimulatory molecules, such as CD80, CD83, and CD86, did not differ among the three infections (FIGS. 12B-12D). A post-sort evaluation using Image stream analysis of the parasitized DCs revealed that LmWT parasites did not show mCherry fluorescence (FIG. 12E-12F).

Figure 4D:
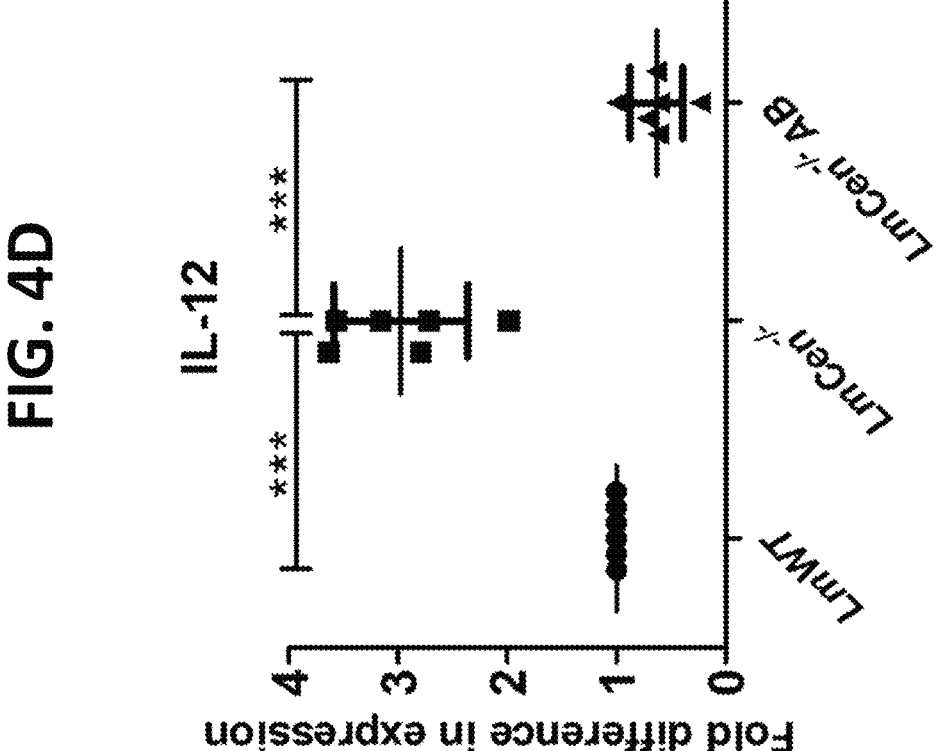
Figures 11A, 11B:
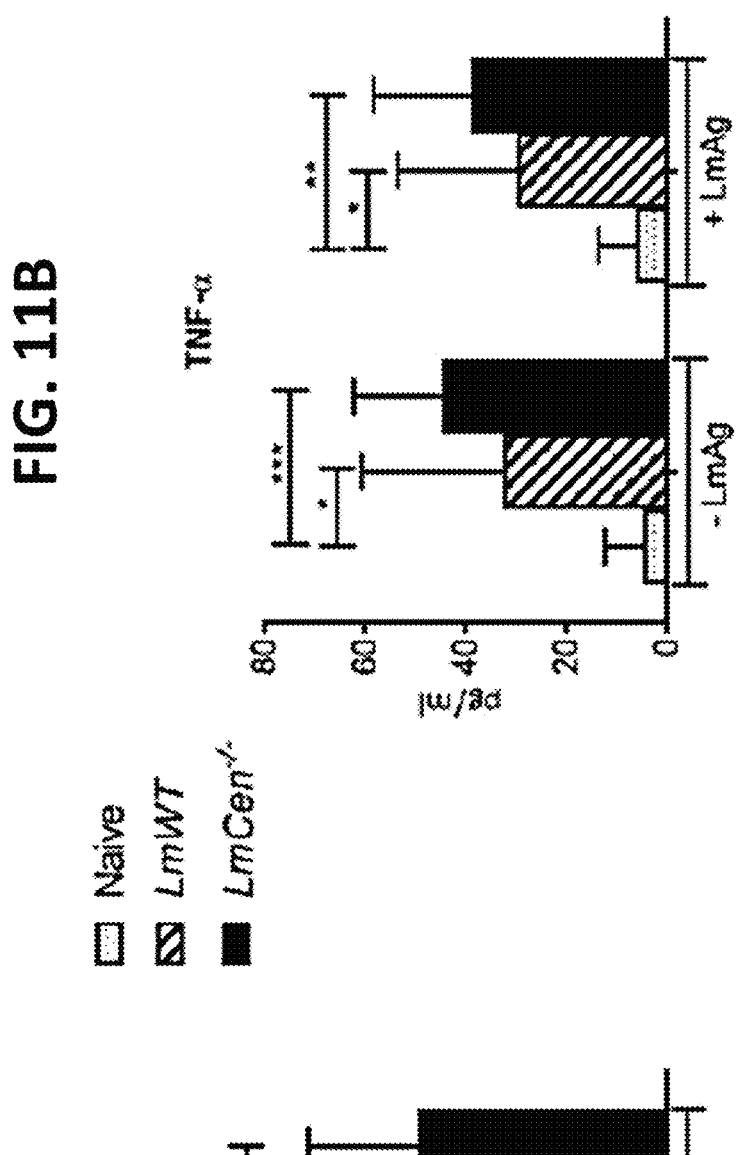
FIGS. 11A-11B show immunogenicity of LmCen−/− parasites. C57BL/6 mice were injected with 1×10⁶ stationary phase promastigotes of LmWT or LmCen−/− intradermally into the ears. At 3 weeks post-infection, ear draining lymph nodes were isolated and cells were cultured at 5×10⁵ cells per well. After 72 hours of culture with or without crude *Leishmania* antigen, culture supernatants were collected and concentrations of IFN-γ (FIG. 11A) and TNF-α (FIG. 11B) were measured using sandwich ELISA. The results are the mean±SEM, six mice per group. Statistical analysis was performed using an unpaired Two-tailed t-test (*$p<0.04$; $p<0.003$, *$p<0.0005$).
Figure 12E:
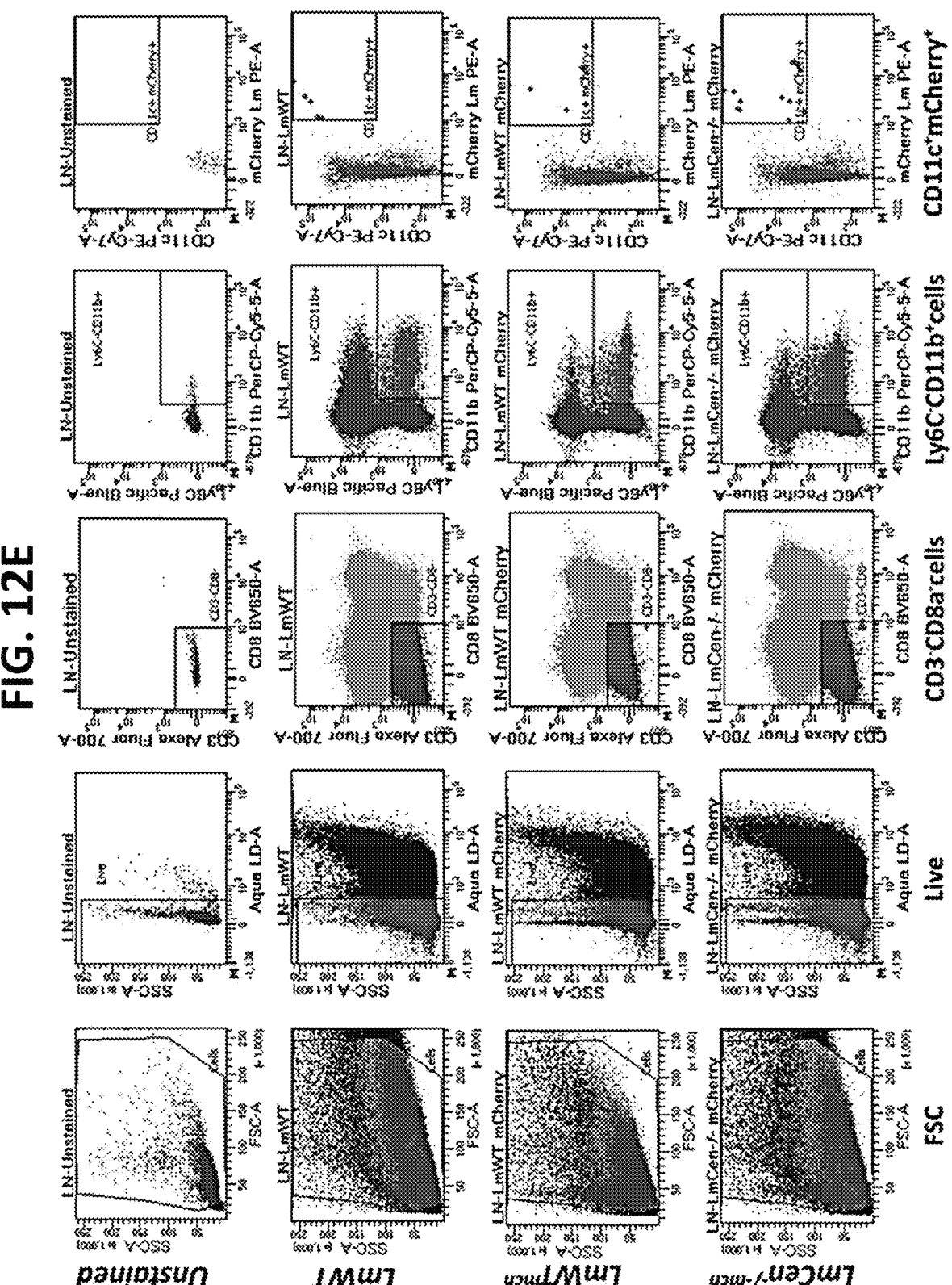

To assess whether LmCen$^{-/-}$ infection induces early proinflammatory cytokines, including IL-12 and IL-6, mice were infected with LmWT$^{mCherry}$, LmCen$^{-/-mCherry}$, and LmCen$^{-/-}$ AB$^{mCherry}$ parasites (FIG. 4A), and the parasitized DCs were sort-selected at 48 h post-infection (FIG. 12E). CD11c$^+$mCherry$^+$DCs isolated from draining lymph nodes showed significantly high levels of IL-12 (FIG. 4D) and IL-6 (FIG. 4E) expression in LmCen$^{-/-mCherry}$-infected DCs compared with LmWT$^{mCherry}$ infection. Importantly, induction of IL-12 and IL-6 expression was absent in the LmCen$^{-/-}$AB$^{mCherry}$ infection (FIG. 4D-4E). mRNA was measured, which is a surrogate for the protein level (Carra et al., J Immunol, 164 (9) 4752-4761, 2000; Murphy et al, J. Immunol., 164: 839-847, 2000). Further, LmCen$^{-/-}$-immunized mice induced significantly more IFN-γ and TNF-α cytokine production, as measured using an ELISA, in cells from draining lymph nodes in response to L. major crude antigens compared with naïve mice 3 weeks after immunization (FIGS. 11A-11B).

Figures 5A, 5B:
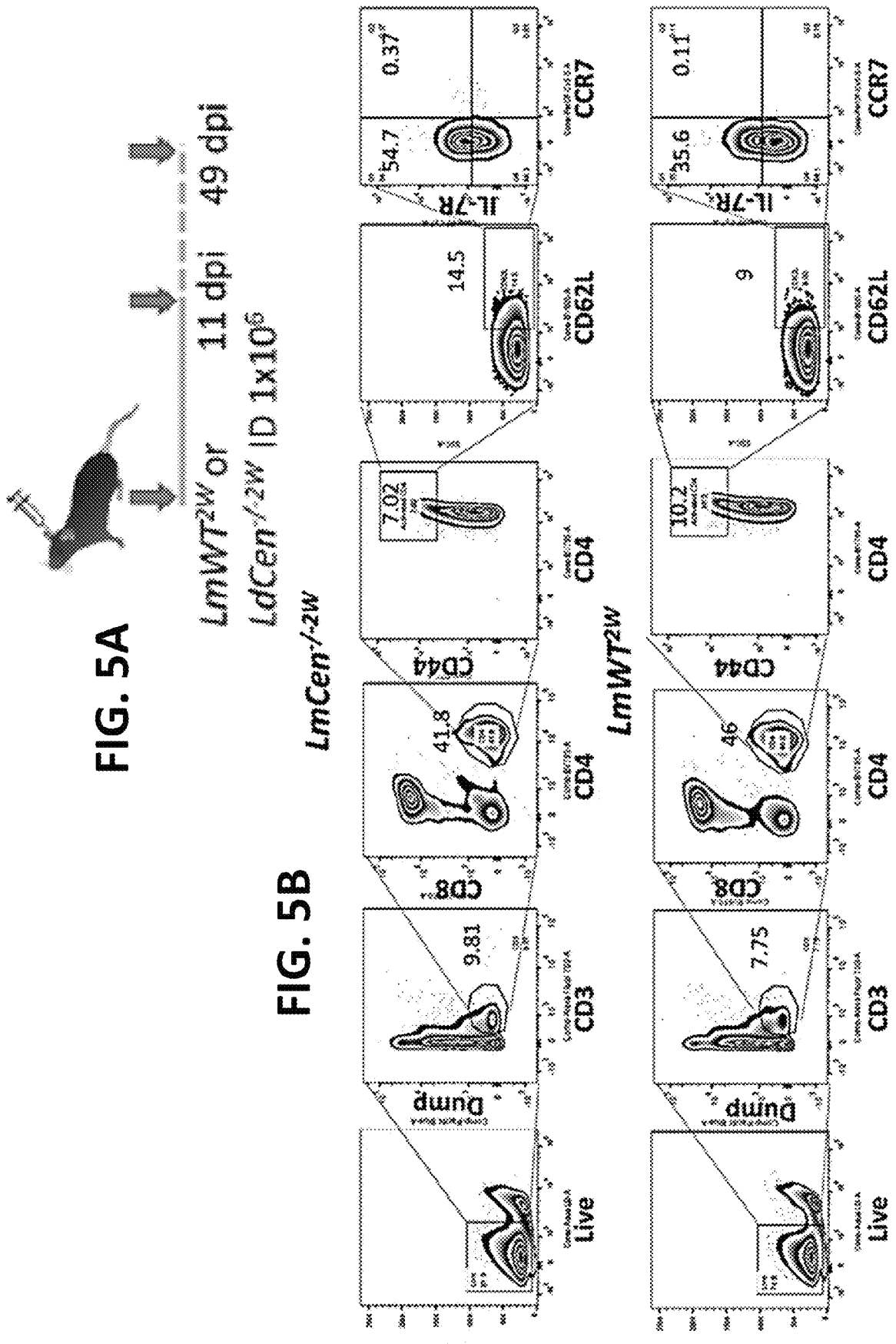
FIGS. 5A-5E show induction of CD4$^+$ T central memory populations by LmCen$^{-/-}$ parasites.
Figure 5C:
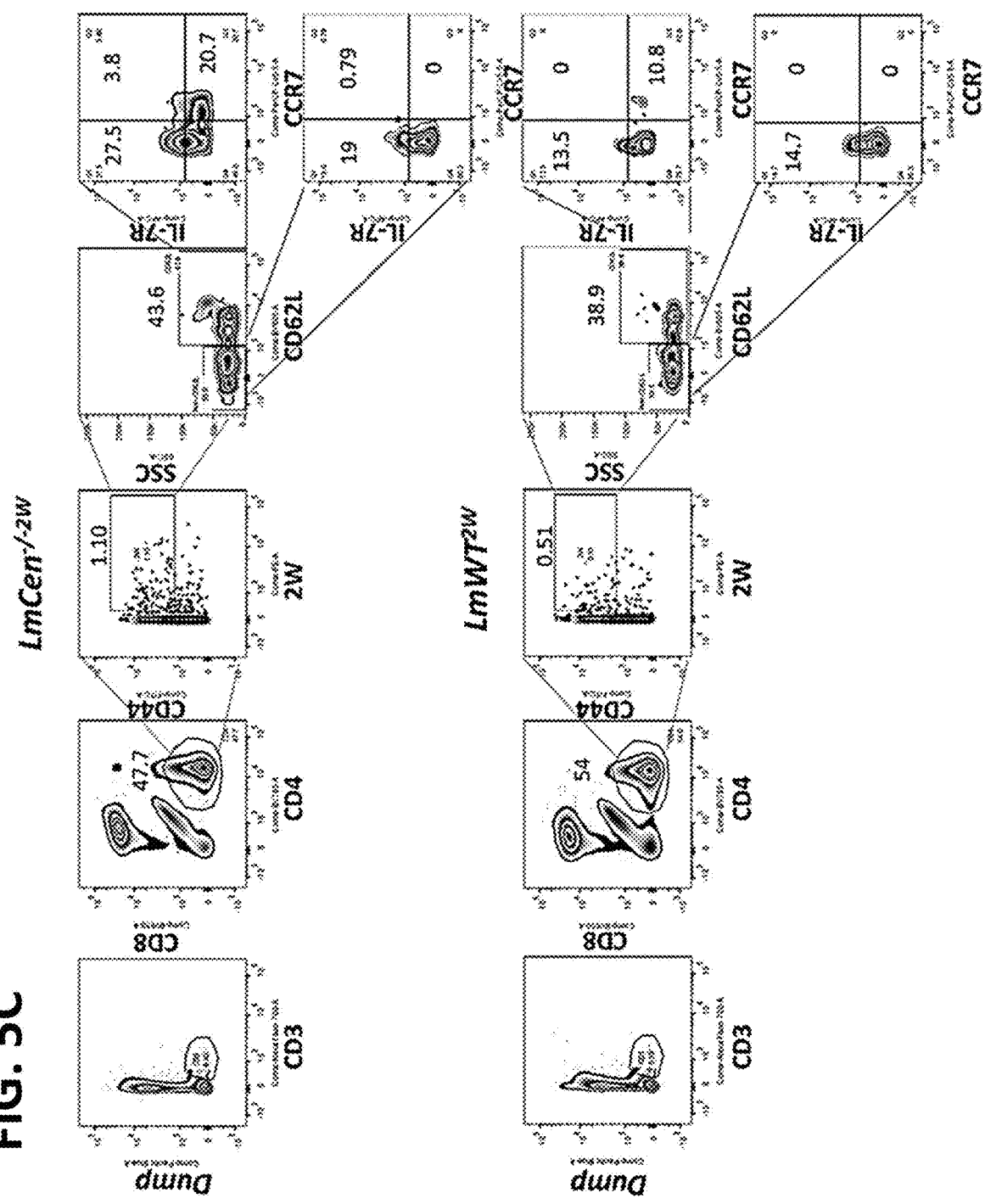
Figure 5E:
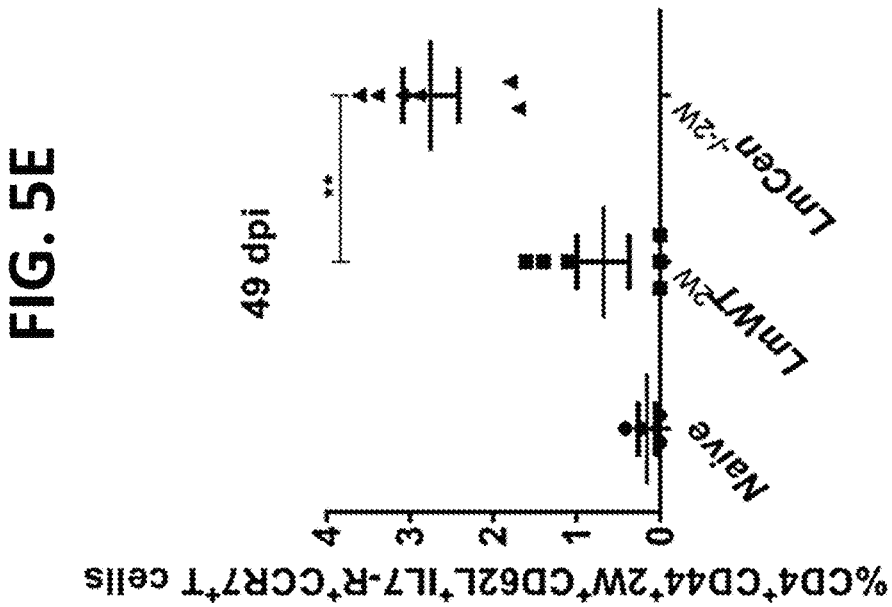
Figure 5D:
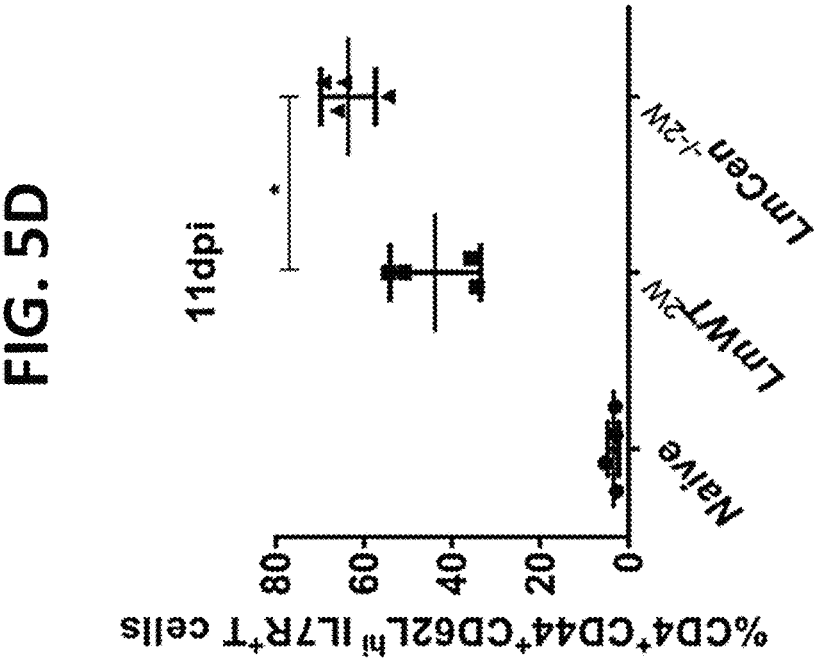
Figure 12J:
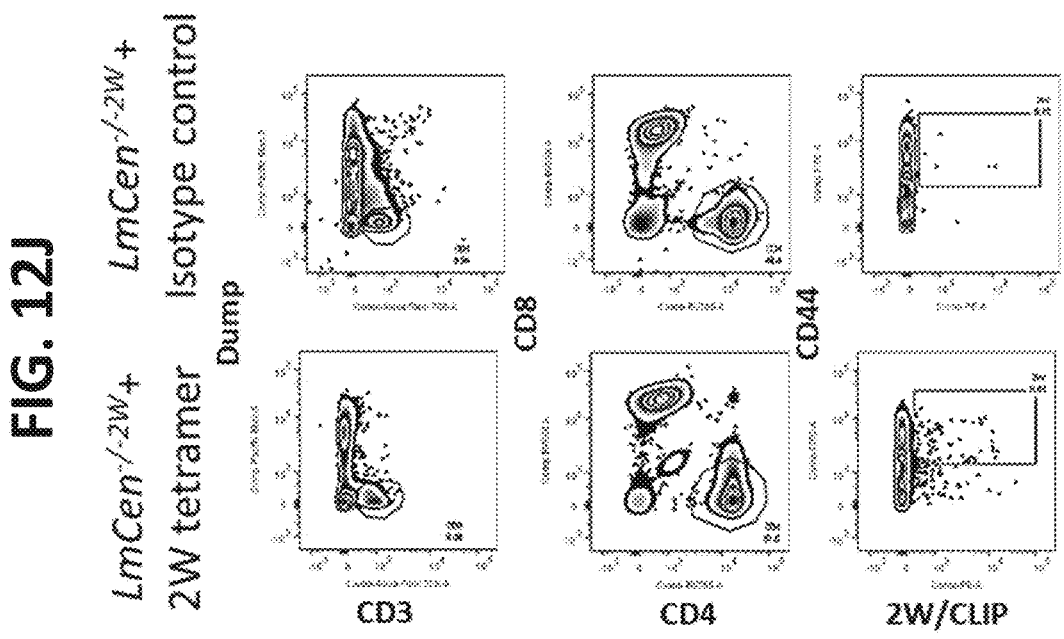
Figure 12I:
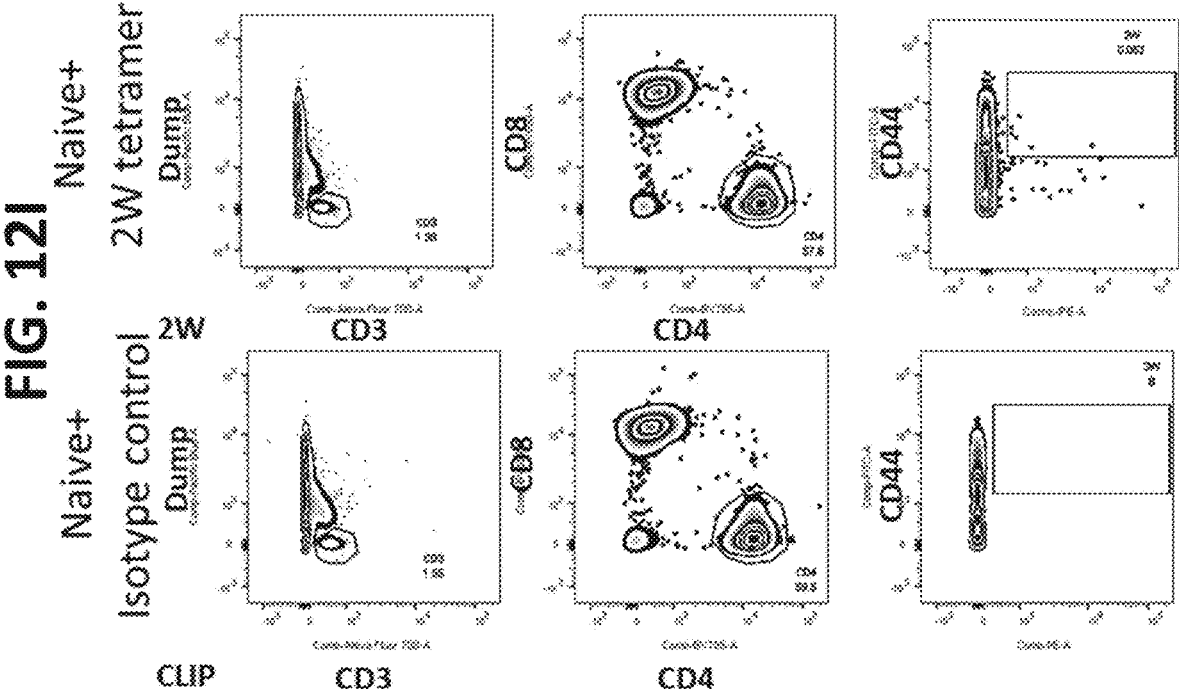

To examine whether immunization with LmCen$^{-/-}$ parasites induces CD4$^+$ central memory responses, C57BL/6 mice were immunized intradermally with LmCen$^{-/-}$ or LmWT parasites secreting a chimeric 3' nucleotidase protein containing a 2W epitope (FIG. 5A, FIG. 12G). Spleen and lymph nodes were collected on days 11 and 49 following immunization and 2W epitope-specific CD4$^+$CD44$^+$IL-7R$^+$ CD62L$^+$CCR7$^+$ central memory T cells were enumerated (FIGS. 5B-5C). At both 11 and 49 days post infection, LmCen$^{-/-}$ immunization induced significantly more 2W epitope-recognizing CD4$^+$CD44$^+$IL-7R$^+$CD62L$^+$CCR7 memory T cells compared with infection by LmWT parasites (FIG. 5D-5E). However, induction of 2W epitope-recognizing CD4$^+$CD44$^+$IL-7R$^+$CD62L$^+$CCR7$^+$ central memory cells was significantly greater at 49 days in LmCen$^{-/-2W}$-infected mice (FIG. 5E). Further, CD62L-cells did not show any IL-7R$^+$CCR7$^+$ populations (FIG. 5C). Absence of binding of cells from LmCen$^{-/-}$ infected mice with an isotype control tetramer revealed the specificity of CD4$^+$ T cell enrichment with 2W tetramers (FIGS. 12I-12J). Taken together, these data reveal that the innate and cellular memory immune response is more effectively augmented following infection with LmCen$^{-/-}$ than with LmWT.

Figure 6A:
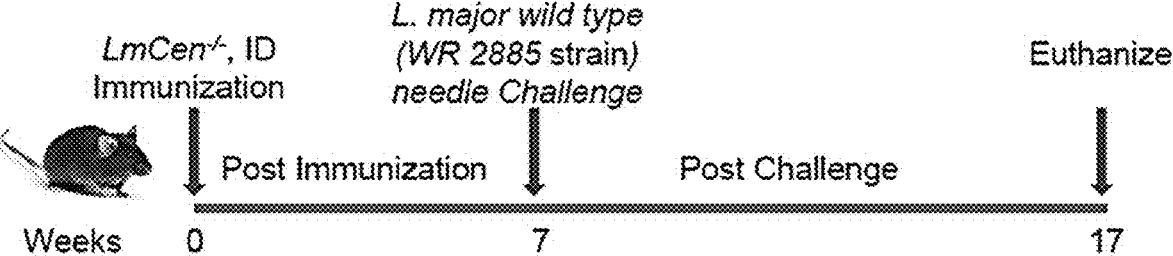
FIGS. 6A-6E show the protective efficacy of LmCen$^{-/-}$ parasites against virulent L. major needle challenge in C57BL/6 mice.
Figure 6B:
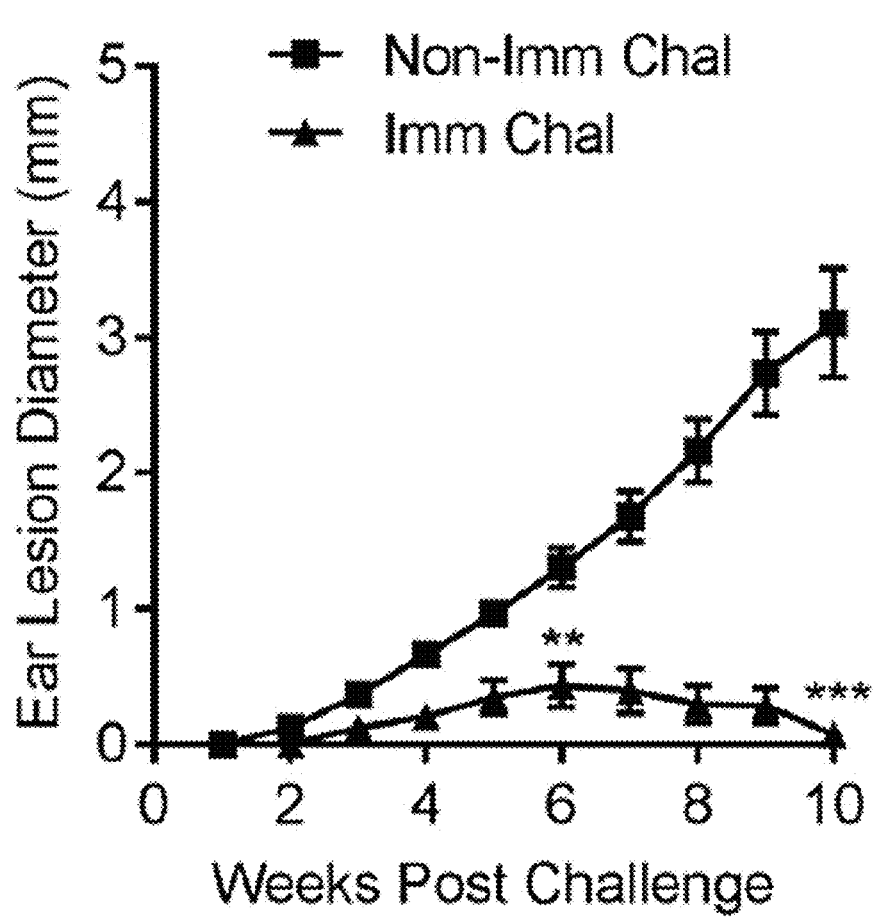
Figure 6C:
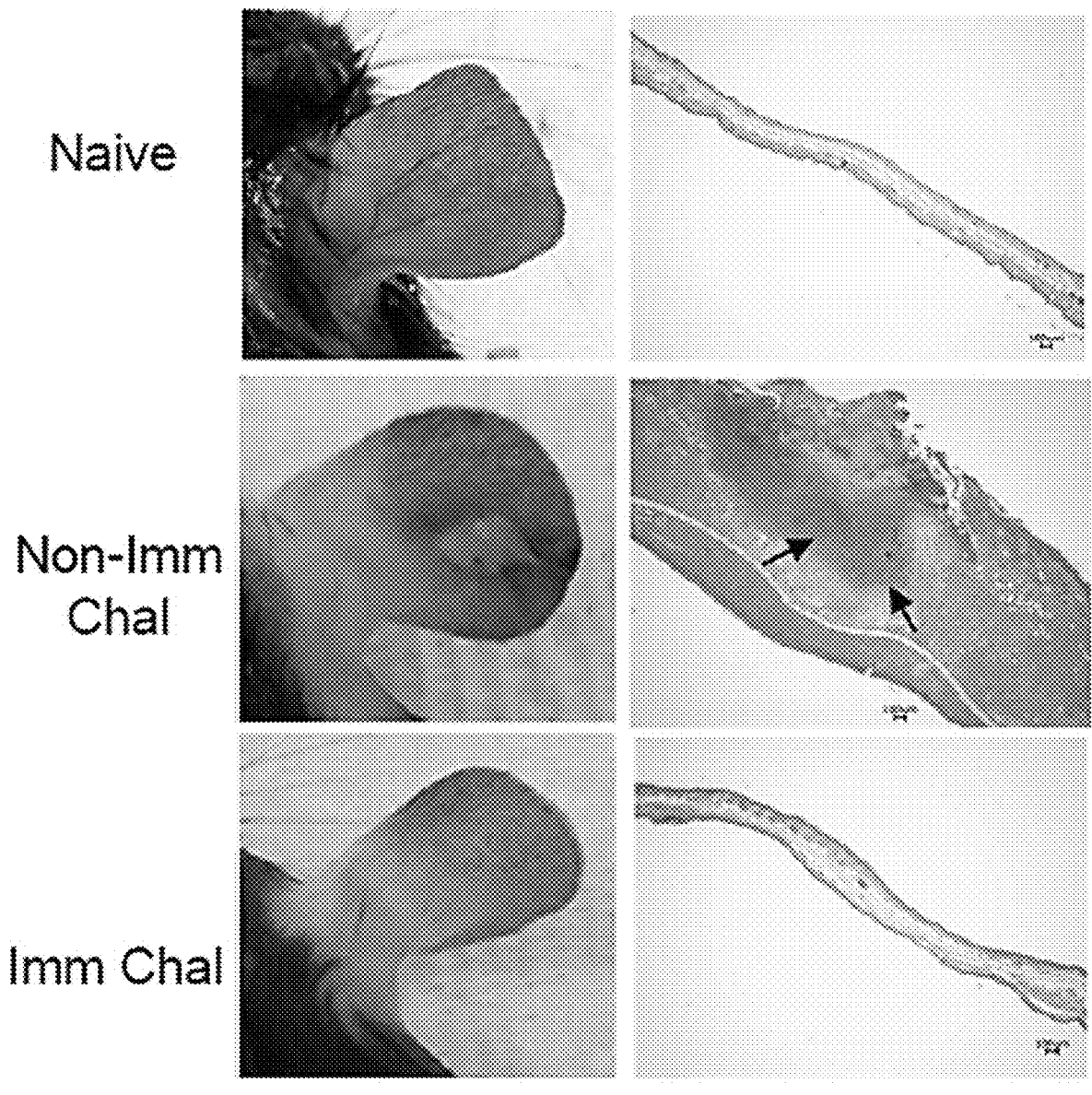
Figures 6D, 6E:
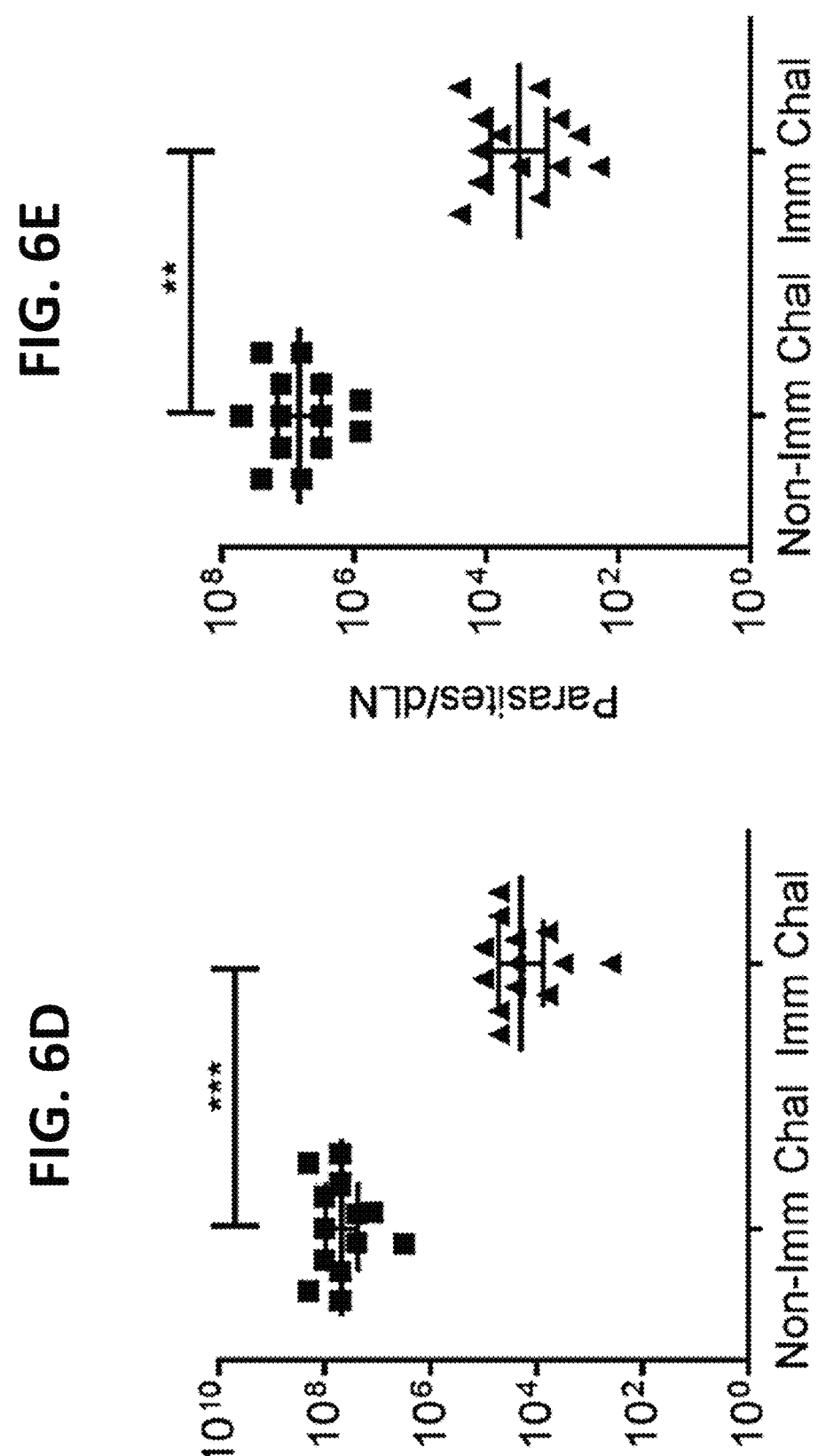
Figures 13A, 13B:
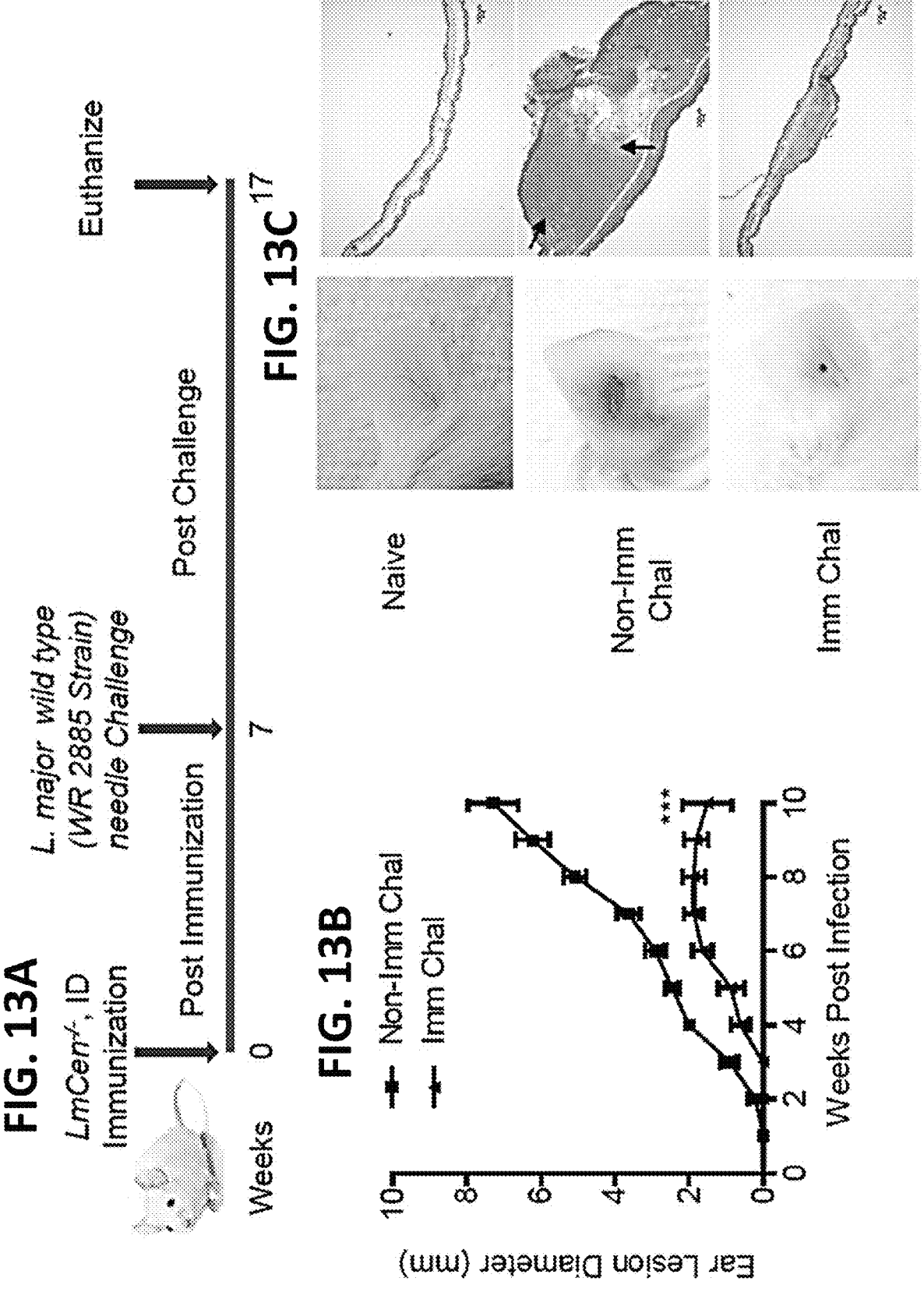
Figures 13D, 13E:
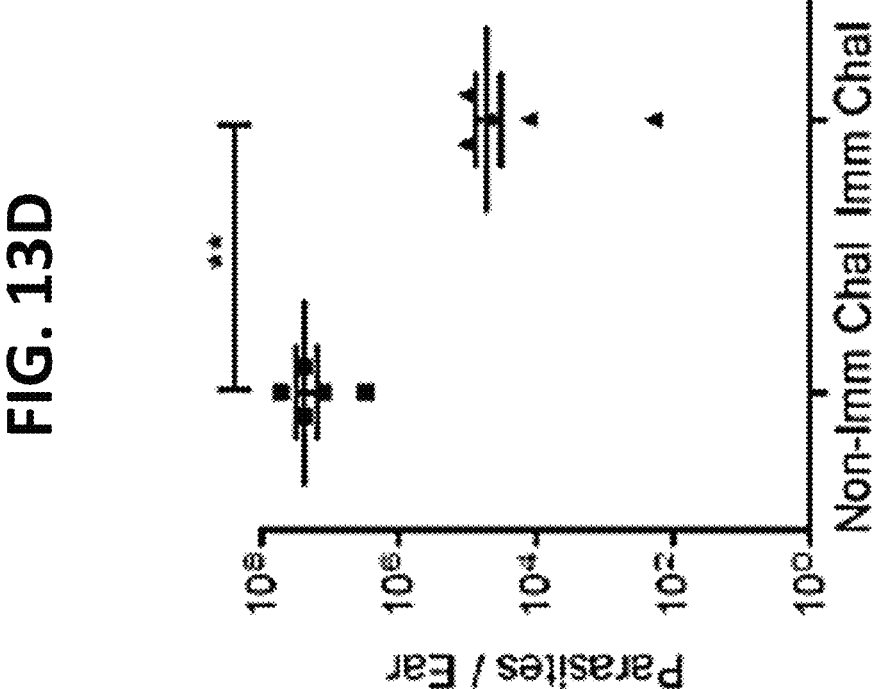
Figure 13G:
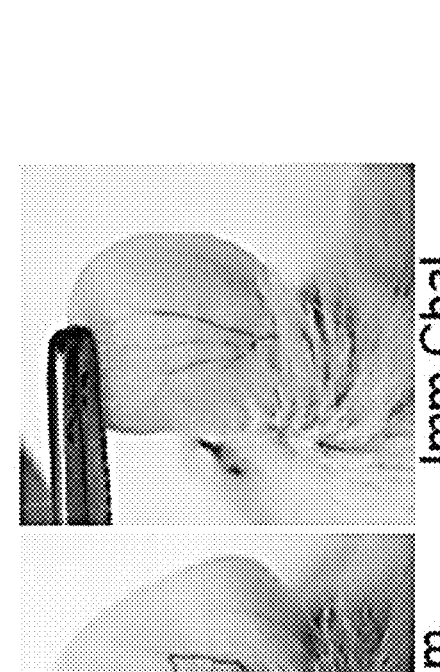
Figure 13F:
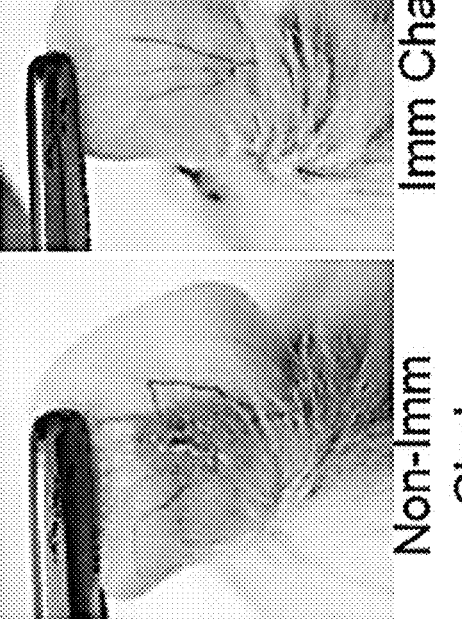

LmCen$^{-/-}$ immunization induced protection against needle infection with wildtype L. major: To investigate the protective efficacy of LmCen$^{-/-}$ against wildtype L. major, both resistant (C57BL/6) and susceptible (BALB/c) mice were immunized with a single intradermal (i.d.) injection with 1×10$^6$ stationary phase LmCen$^{-/-}$ in one ear. Seven weeks post-immunization, mice were challenged with 750 metacyclic wildtype L. major (WR 2885 strain) parasites in the contralateral ear via the i.d. route (FIG. 6A for C57BL/6; FIG. 13A for BALB/c). Following challenge with wildtype L. major, lesion development was assessed up to 10 weeks for the C57BL/6 mice (FIGS. 6B-6C). In the non-immunized-challenged group, mice developed a non-healing open ulcer that progressively increased in size (FIG. 6C). No open ulcers were observed in the LmCen$^{-/-}$-immunized-challenged group and only a moderate swelling that subsided from 5-9 weeks post-challenge was observed in 6 of 13 mice. FIG. 6C depicts the ear pathology at 10 weeks post-challenge compared with a naïve unchallenged ear. Importantly, histopathological analysis revealed no clear difference between immunized-challenged and naïve mice ears, while non-immunized-challenged mice ears developed large lesions with open ulcers involving an influx of inflammatory cells (FIG. 6C). The parasite load in the challenged ear and draining lymph node were also quantified at 10 weeks post-challenge, revealing that the immunized group had a significantly lower parasite load (approximately a 4-log fold and a 3.2-log fold reduction, respectively) compared with the non-immunized group (FIGS. 6D-6E). Similarly, highly susceptible BALB/c mice were protected following immunization with LmCen$^{-/-}$ parasites (FIGS. 13A-13E). At 10 weeks post-challenge with wildtype L. major parasites, immunized BALB/c mice were protected as measured by both reduced lesion size (FIGS. 13B-13C) and reduced parasite burden (FIGS. 13D-13E) compared with non-immunized-challenged mice. A similar lack of non-healing open ulcer was observed in LmCen$^{-/-}$-immunized BALB/c mice challenged with other wildtype strains of *L. major*, such as *L. major* FV9 (FIG. 13F) and *L. major* LV39 (FIG. 13G).

Figure 7A:
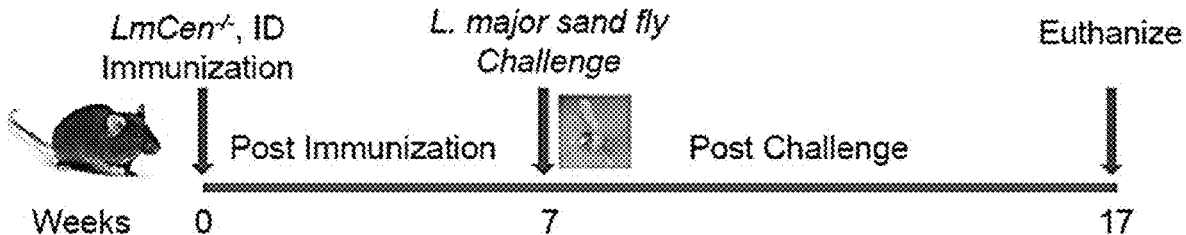
FIGS. 7A-7E show protective efficacy of LmCen$^{-/-}$ parasites against sand fly challenge in C57BL/6 mice.
Figure 7B:
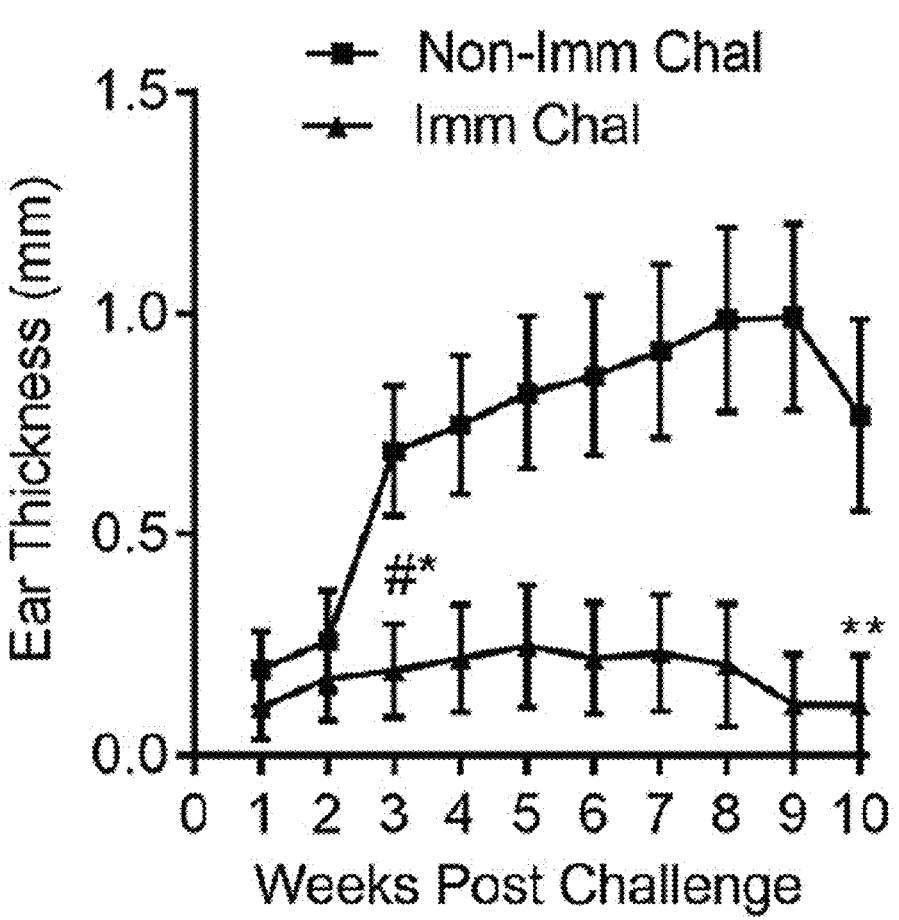
Figure 7C:
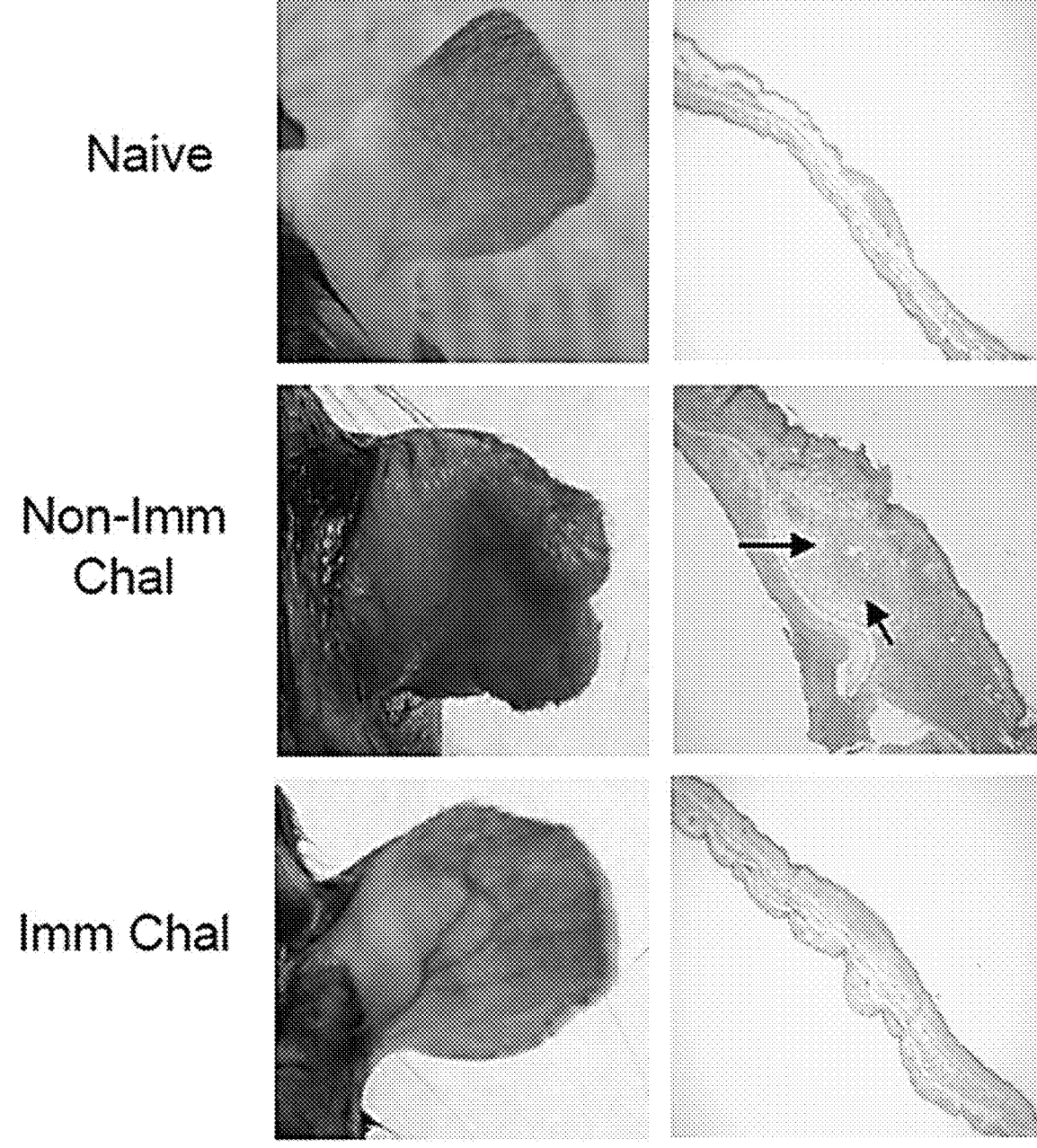
Figures 7D, 7E:
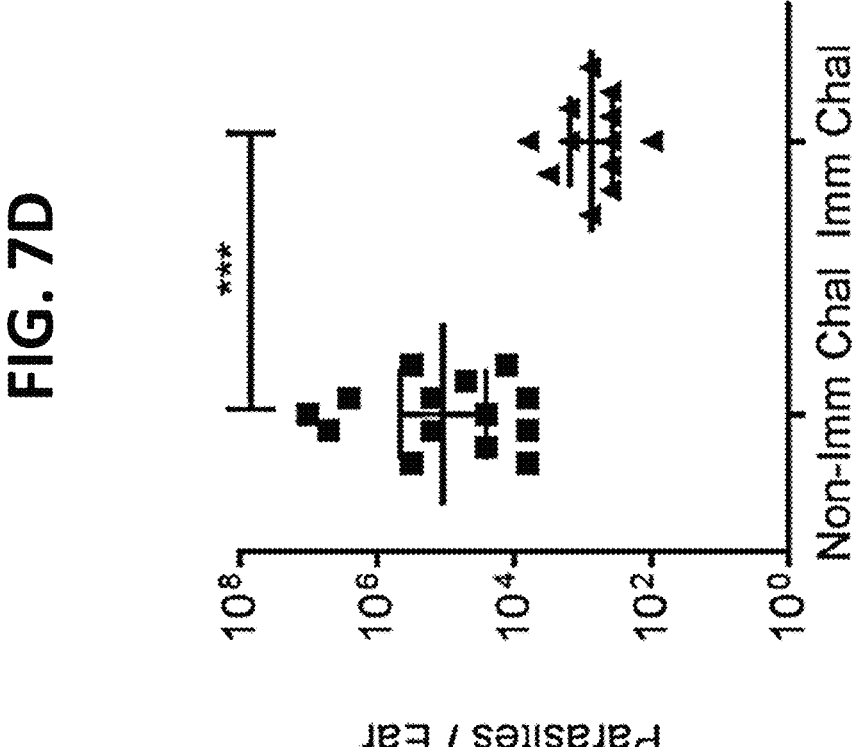

LmCen$^{-/-}$ immunization induced protection against sand fly-transmitted *L. major* infection: It is substantially more difficult and more relevant to demonstrate immunological protection against *L. major* infection initiated by a sandfly challenge than by a needle injection challenge (Peters, N. C. et al., PLoS Pathog. (2009), doi:10.1371/journal.p-pat.1000484; Peters, N. C. et al., J. Immunol. (2012), doi:10.4049/jimmunol.1201676). Therefore, to determine the efficacy of LmCen$^{-/-}$ immunization against sand fly transmitted cutaneous infection by *L. major*, C57BL/6 mice were immunized with a single i.d. injection of $1\times10^6$ LmCen$^{-/-}$ stationary phase parasites and mice were infected by exposure to bites of 10 *L. major*-infected sand flies in the contralateral ear 7 weeks post-immunization (FIG. 7A). Disease progression was monitored for 10 weeks post-challenge by measuring lesion growth and assessing parasite burden in the ear and draining lymph node (FIGS. 7B-7E). Notably, only 1/12 immunized-challenged mice developed a visible lesion, while 10/14 non-immunized-challenged mice developed progressive lesions in the ear that were significantly larger than the single lesion observed in immunized-challenged mice (FIGS. 7B-7C). At 10 weeks post-challenge, a significant reduction of the parasite burden was observed both in the ear and draining lymph node (approximately 2 log-fold reduction in both) of immunized-challenged mice compared with non-immunized-challenged mice (FIGS. 7D-7E). Some of the draining lymph nodes in the immunized-challenged mice did not have parasites (FIG. 7E). These results demonstrate that immunization with LmCen$^{-/-}$ mediates significant protection under natural conditions of infection (for example, parasite transmission by an infected sand fly).

Figure 8A:
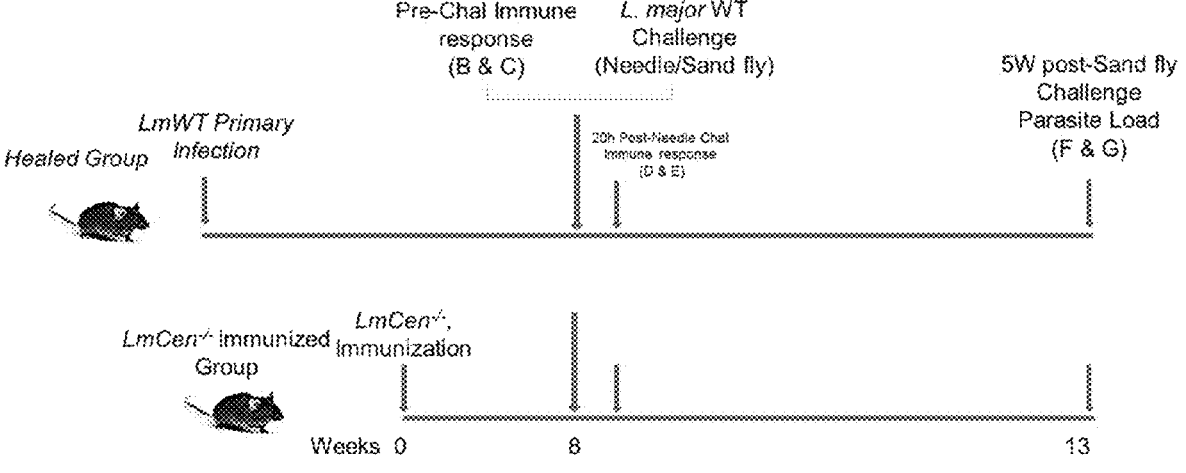
FIGS. 8A-8G show LmCen$^{-/-}$ immunization or leishmanization with LmWT mediates comparable host protection against wildtype L. major infection.
Figure 8B:
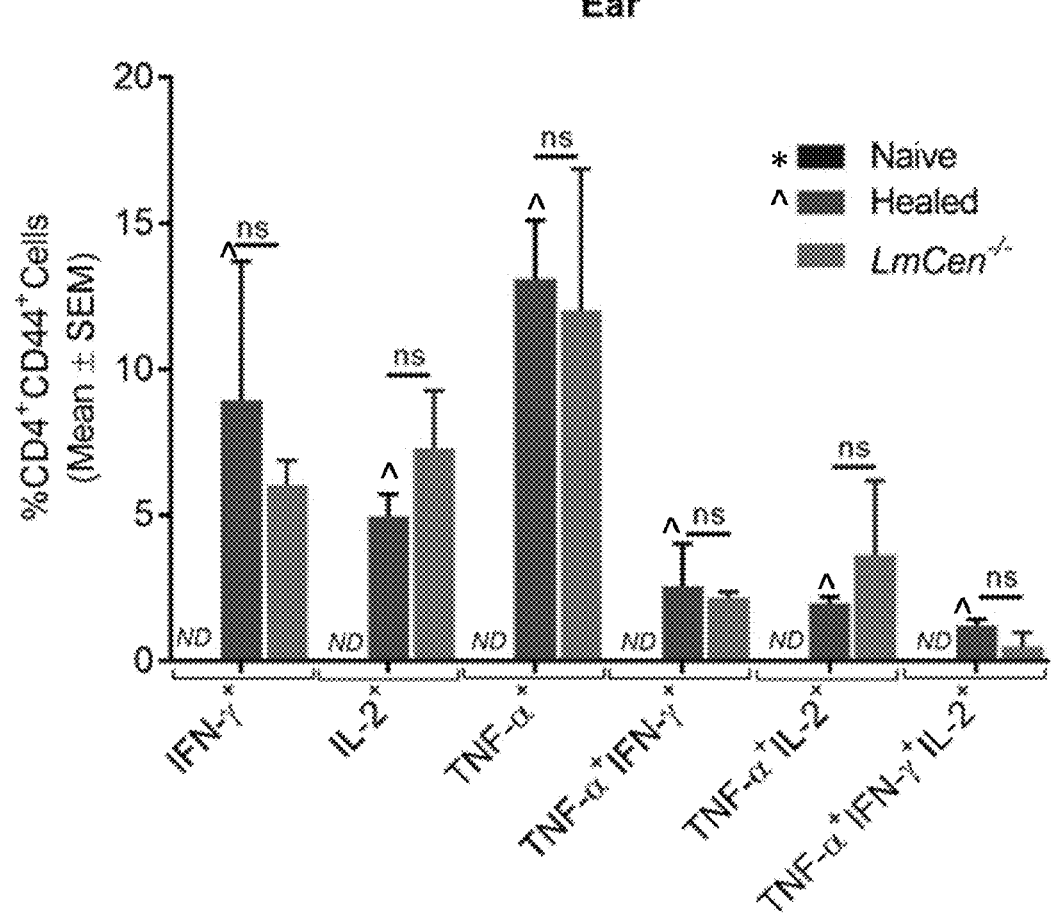
Figure 8C:
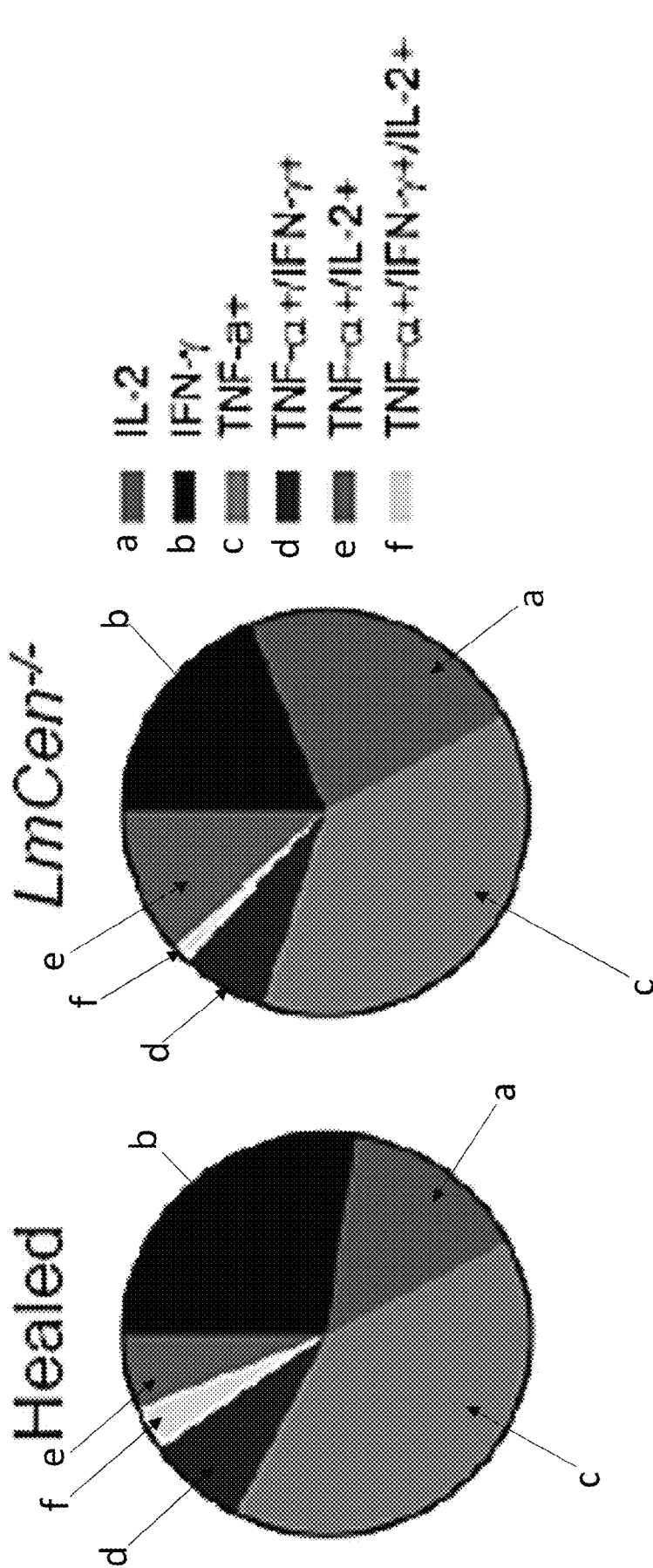
Figures 8D, 8E:
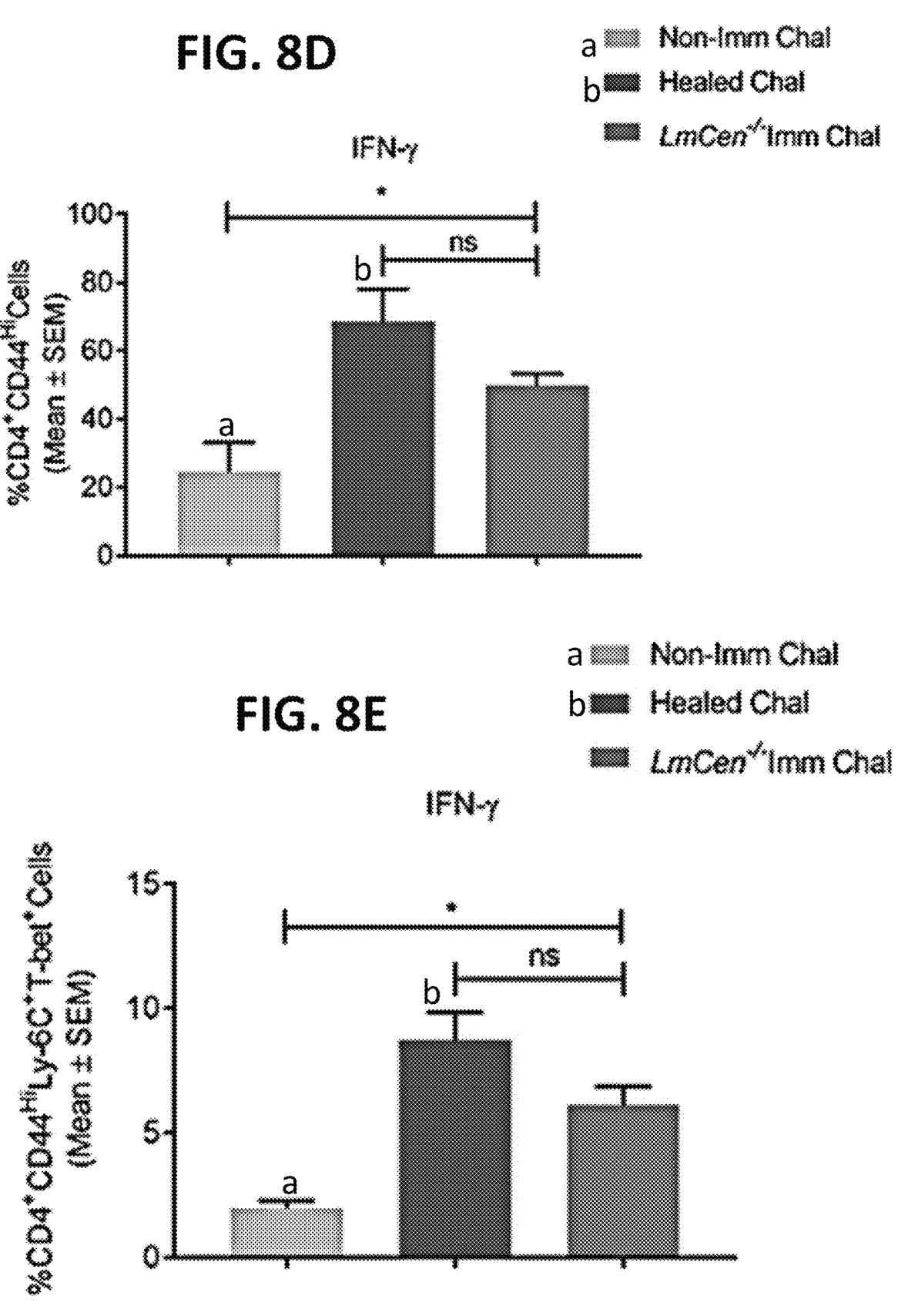
Figure 14B:
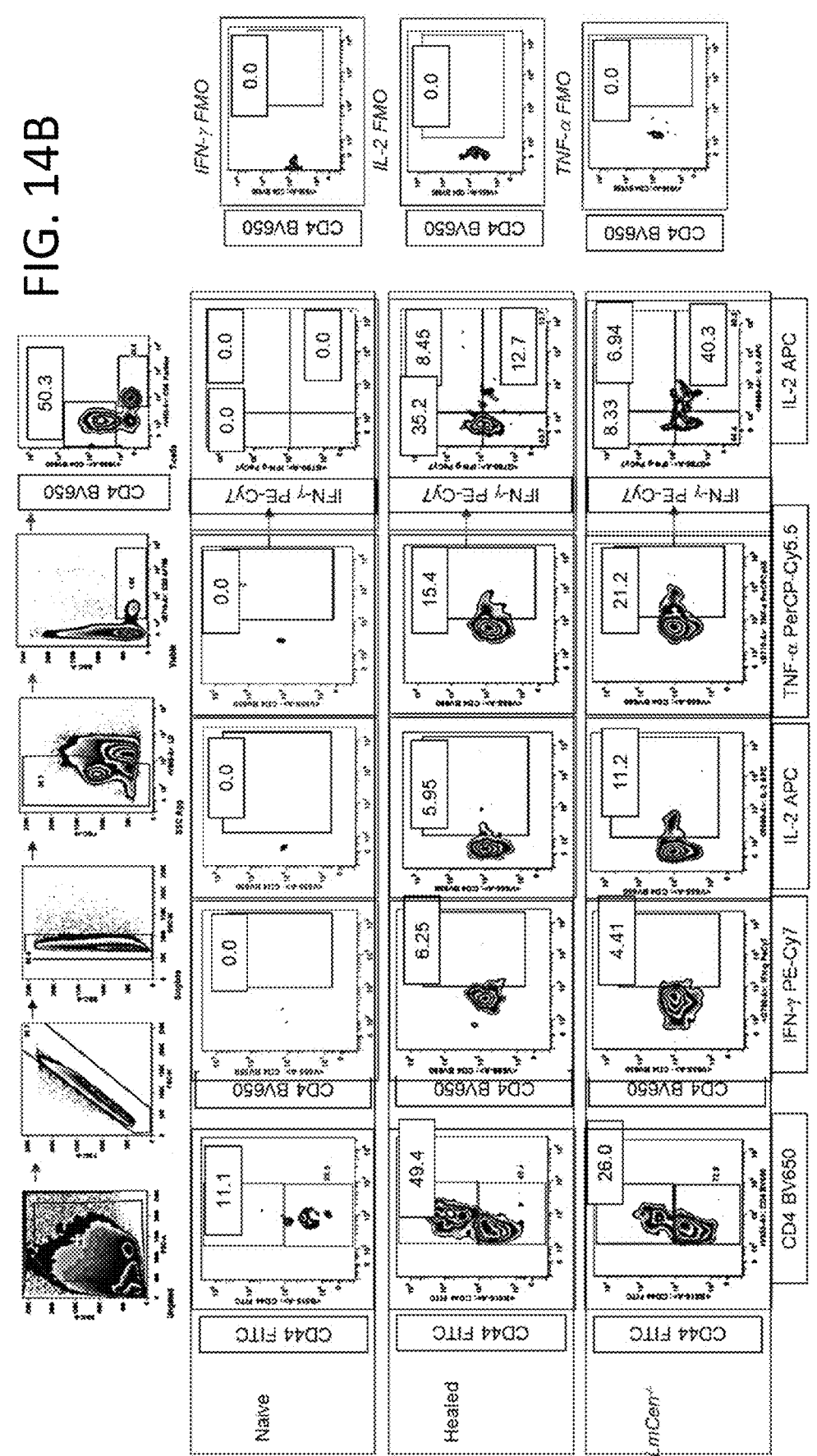
Figure 14C:
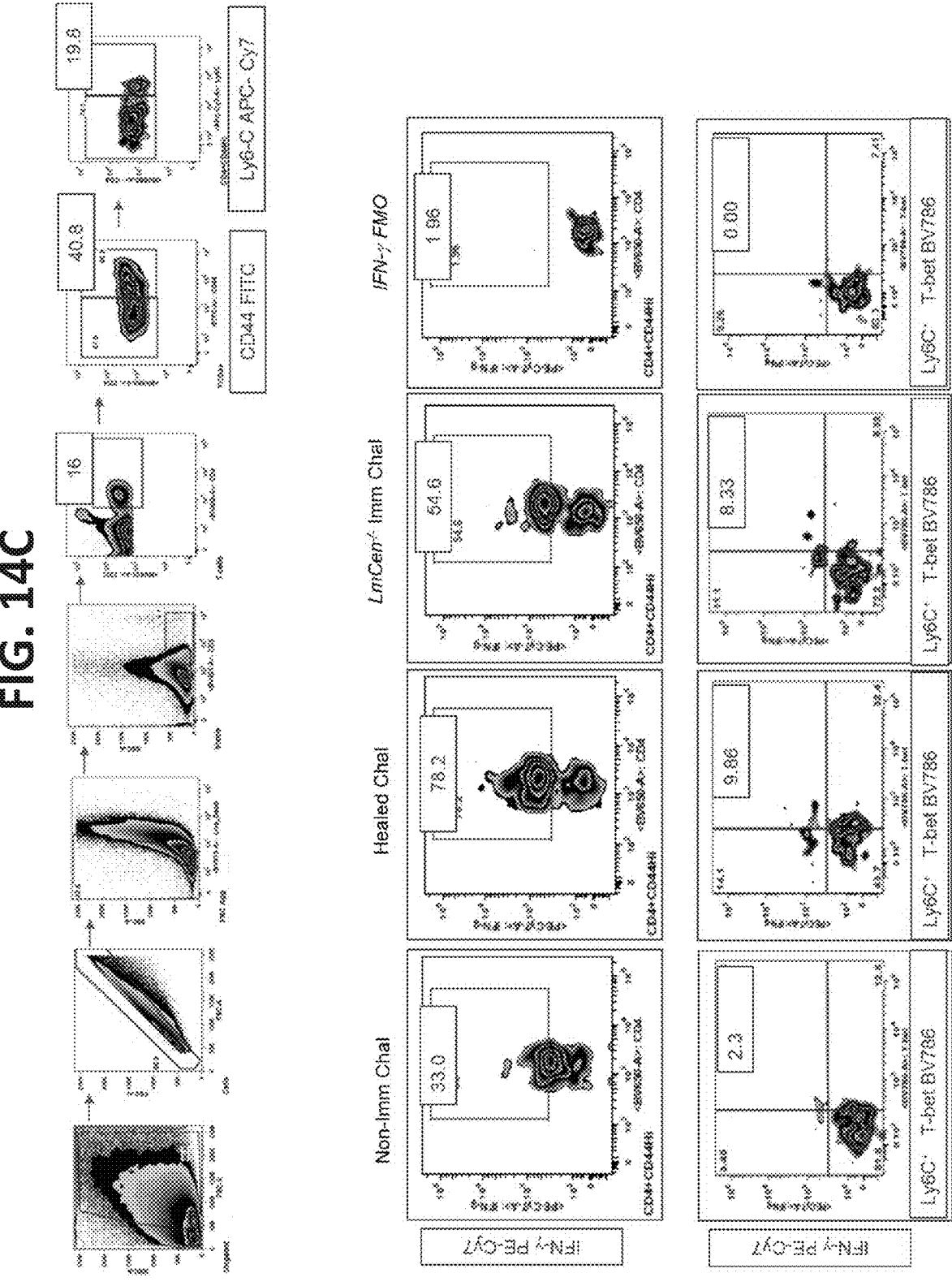
Figure 14D:
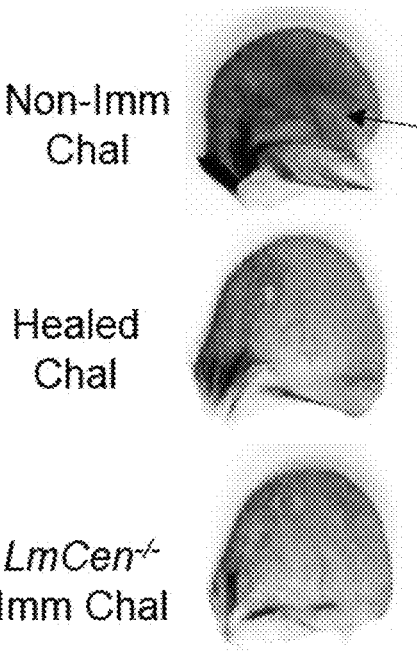

LmCen$^{-/-}$ immunization or healing from primary infection with LmWT (leishmanization) induced comparable host protective immune response against *L. major* infection: Having shown that LmCen$^{-/-}$ induces protection against both a needle and natural model of a sand fly challenge, the immune response of the LmCen$^{-/-}$ immunized group (8 weeks post-immunization) was subsequently compared with a primary LmWT infection (healed group) at 12-weeks post-primary infection (FIG. 8A). Antigen-experienced CD4$^+$ T cells were first gated based on their surface expression of CD44 (FIG. 14A), and CD4$^+$CD44$^+$ cells were rearranged into different subpopulations based on their production of TNF-α, IFN-γ, and IL-2. The results showed that both LmCen$^{-/-}$ immunization and healed groups of mice induced comparable single and multiple cytokines secreting CD4$^+$CD44$^+$ T cells upon re-stimulation with *L. major* freeze-thaw antigen (LmFTag) (FIGS. 8B-8C). Upon challenge with wildtype *L. major* parasites by needle injection, both healed and LmCen$^{-/-}$ parasite-immunized mice induced a significantly higher percentage of CD4$^+$IFN-γ$^+$ cells and IFN-γ$^+$ effector T cells (CD4$^+$CD44$^+$T-bet$^+$Ly6C$^+$) compared with the non-immunized group (FIGS. 8D and 8E).

Figure 8F:
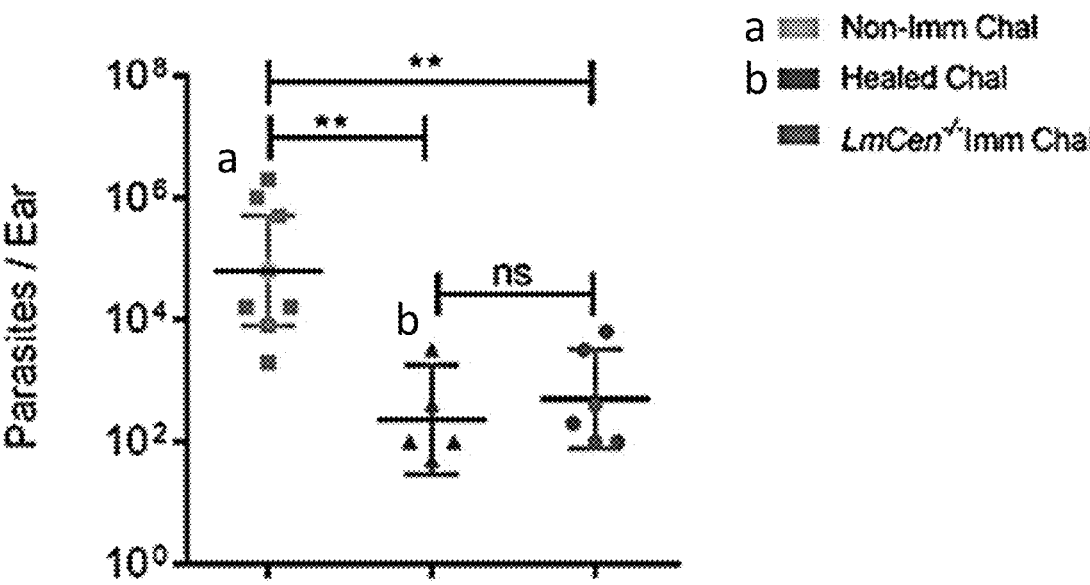
Figure 8G:
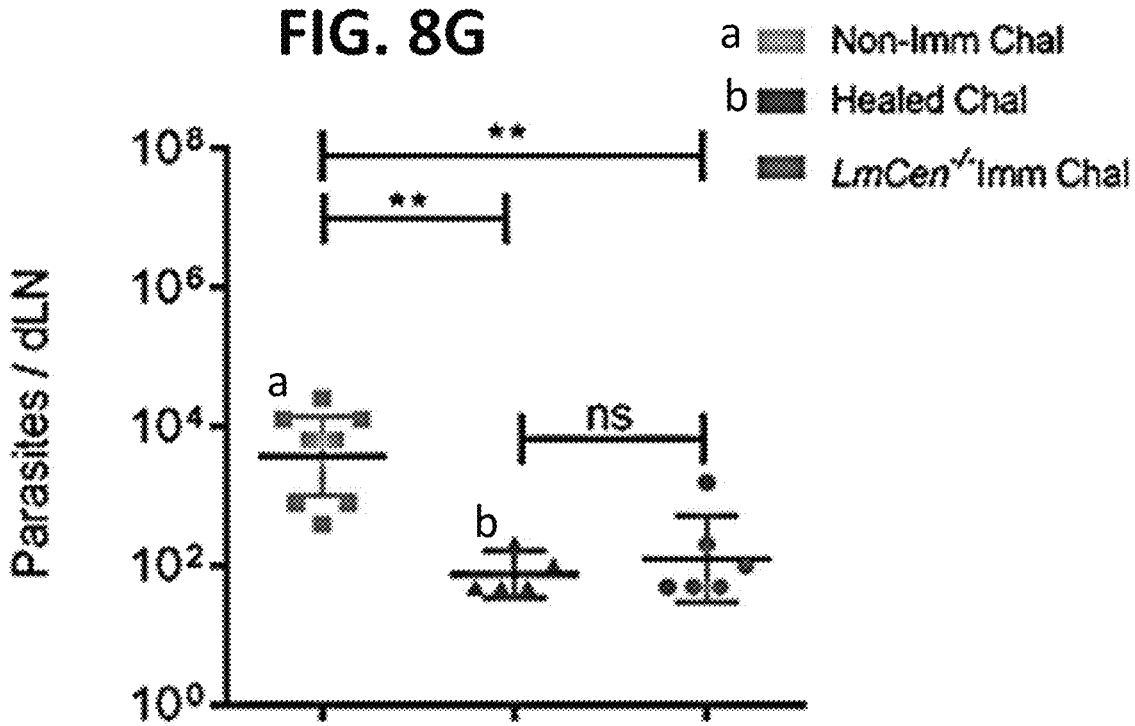

Both groups were challenged with an *L. major* WT infected sand fly, and the parasite load was determined as outlined in FIG. 8A. After five weeks post-challenge, significant reduction of parasite burden was observed in the ear (2.4 log-fold in the healed group, and 2.1 log-fold in the LmCen$^{-/-}$-immunized group) and draining lymph nodes (1.7 log-fold in the healed group, and 1.48 log-fold in the LmCen$^{-/-}$-immunized group) in the healed and LmCen$^{-/-}$-immunized groups compared with the non-immunized group (FIGS. 8F and 8G). These results demonstrate that LmCen$^{-/-}$ immunization is as effective as leishmanization (LmWT infection) in generating a protective immune response and protecting against sand fly-mediated infection with WT *L. major*.

Example 3: Non-Persistence and Nonpathogenic Nature of Live Attenuated LmCen$^{-/-}$ Parasites in a Hamster Model This examples describes a study to determine the persistence of LmCen$^{-/-}$ parasites following intradermal immunization (ID) using a hamster model. Hamsters were infected with 10$^6$ total of either LmWT or LmCen$^{-/-}$ parasites in the stationary phase (6-15 hamsters per group). Infected hamsters were sacrificed at days 3, 15, 28 and 49 post-inoculation (FIG. 15A) and parasite burden was determined at the inoculation site (ear) and in draining lymph node (dLN) by limiting dilution assay. Representative photographs of ears of LmWT and LmCen$^{-/-}$ infected hamsters are shown in FIG. 15B. Ear lesion diameter was measured at days 3, 15, 28 and 49 post-infection. As shown in FIG. 15C, immunization with LmWT parasites let to an increase in ear lesion size over time, while no change in ear lesion diameter was detected in hamsters immunized with LmCen$^{-/-}$ parasites.

Figure 16A:
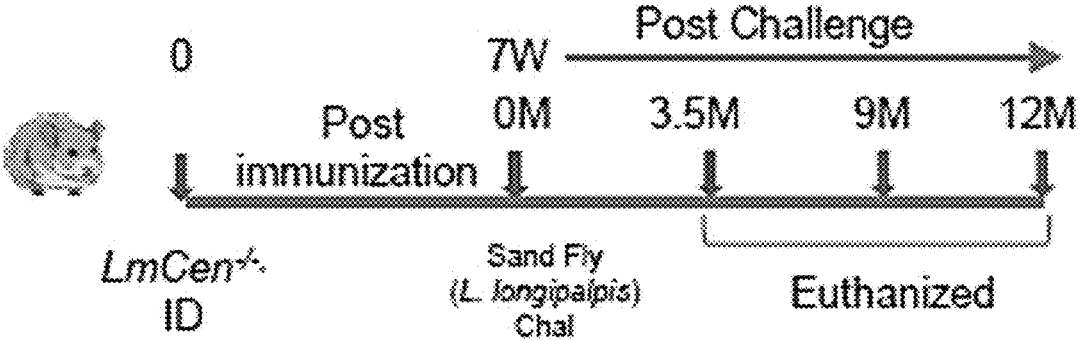
FIGS. 16A-16D show that LmCen−/− immunization provides cross-protection against a natural mode of an *L. donovani* infected sand fly challenge in hamsters.
Figure 16B:
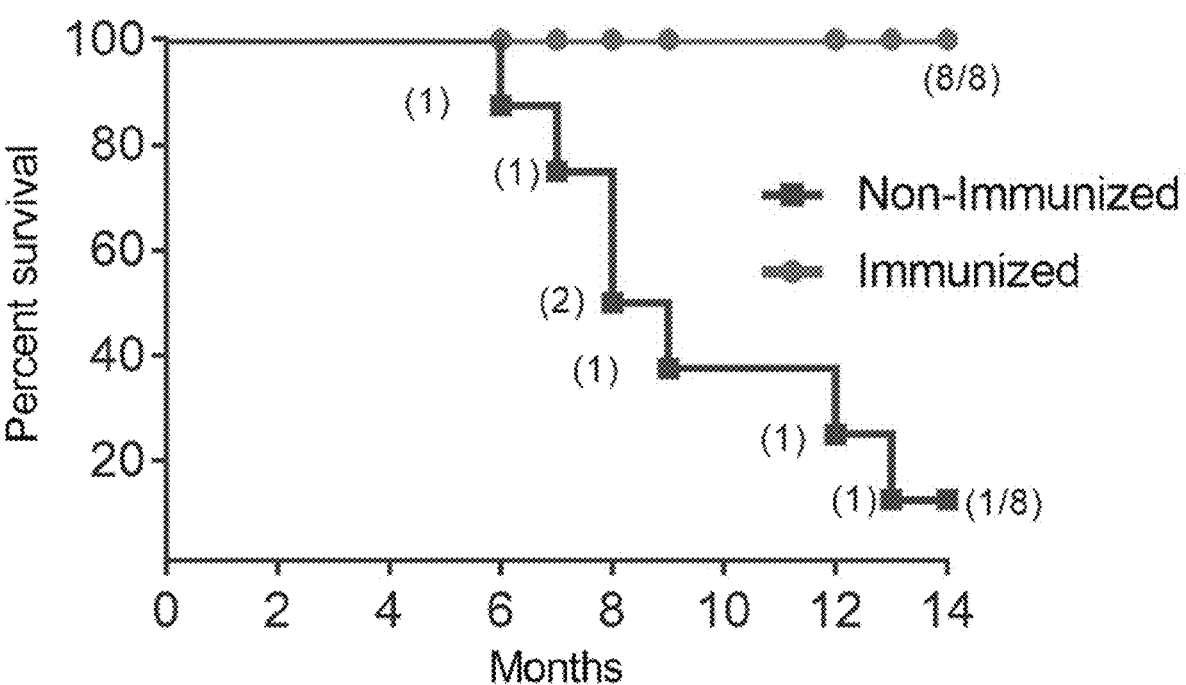
Figures 16C, 16D:
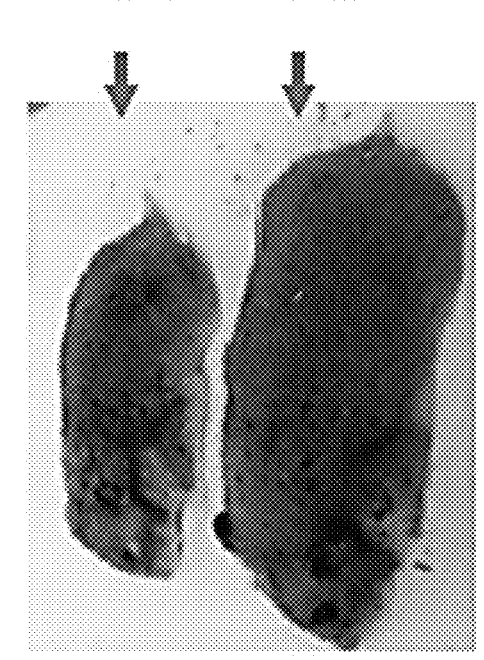

Example 4: LmCen$^{-/-}$ Immunization Provides Cross-Protection Against the Natural Mode of *L. donovani* Infection This example describes a study to determine the cross-protective efficacy of LmCen$^{-/-}$ parasites against *L. donovani* infected sand fly (*Leutzomia longipalpis*) challenge. Hamster were immunized by intradermal injection in the left ear dermis with $1\times10^6$ stationary phase centrin-deleted *L. major* (LmCen$^{-/-}$) promastigotes. Seven weeks post-immunization, both immunized and age-matched non-immunized animals (n=8 per group) were challenged with thirty *L. donovani* infected sand flies in the right ear and subsequently analyzed at 3.5, 9 and 12 months post-challenge (FIG. 16A). Kaplan-Meier survival curves were generated for LmCen$^{-/-}$-immunized and non-immunized hamsters following challenge with *L. donovani* infected sand flies. As shown in FIG. 16B, all immunized animals survived, while 7 of 8 animals succumbed to infection within 14 months. A photograph of a representative immunized hamster and a non-immunized hamster 9 months after challenge is shown in FIG. 16C. The non-immunized hamster exhibits the clinicopathologic features of visceral leishmaniasis (VL). FIG. 16D is a photographs of representative spleens from LmCen$^{-/-}$-immunized and non-immunized challenged hamsters, as well as a spleen from a naïve hamster. Spleen size of all the hamsters was measured in centimeter. The spleens of the non-immunized hamsters were significantly larger than spleens from the immunized and naïve hamsters.

Example 5: LmCen$^{-/-}$ Grown in Serum Free Medium are as Immunogenic as LmCen$^{-/-}$ Grown in Serum Containing Medium This example describes a study to evaluate cytokine gene expression induced by LmCen$^{-/-}$ parasites grown in the presence and absence of serum. Hamsters were intradermally immunized with $10^6$ parasites in the stationary phase of lab-grown LmCen$^{-/-}$, GLP LmCen$^{-/-}$ grown in the presence of serum or GLP LmCen$^{-/-}$ grown in the absence of serum. Cytokine expression was measured at six weeks post-immunization. IFN-γ, TNF-α, IL-4 and IL-10 expression in spleen cells was measured after 24 hours of *L. major* freeze thaw antigen (FTAg) re-stimulation. For gene expression, the 2-ΔΔCT method was employed to determine the fold expression of each gene (normalized against γ-actin expression). The results are shown in FIG. 19. Cytokine expression was similar between hamsters immunized with LmCen$^{-/-}$ grown in the presence of serum and hamsters immunized with LmCen$^{-/-}$ grown in the absence of serum.

Example 6: GLP-Grade LmCen$^{-/-}$ Parasites Protect Hamsters Against Challenge with Wild Type *L. donovani*

Figure 20A:
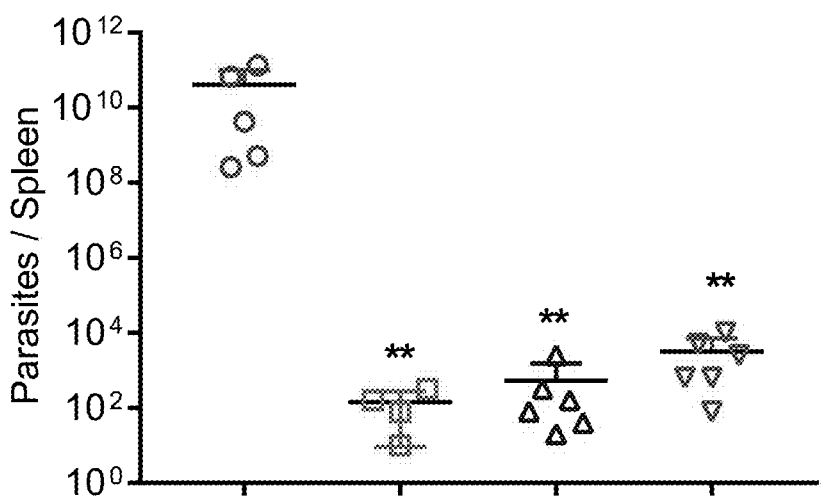
FIGS. 20A-20B show that GLP-grade LmCen$^{-/-}$ parasites induce host protection in hamsters against wild type infection. Parasite loads in the spleen (FIG. 20A) and liver (FIG. 20B) of hamsters either immunized with laboratory-grade (Laboratory-Grade Imm Chal, n=4) or GLP-grade (GLP-Grade Imm Chal, n=6) LmCen$^{-/-}$ parasites or age matched non-immunized control (Non-Imm Chal, n=5) were determined by limiting dilution following nine months post needle challenge with *L. donovani* and expressed as number of parasites per spleen and per gram of liver. Results (mean±SD) are representative of one experiment (p values were determined by Mann Whitney two-tailed test).
Figure 20B:
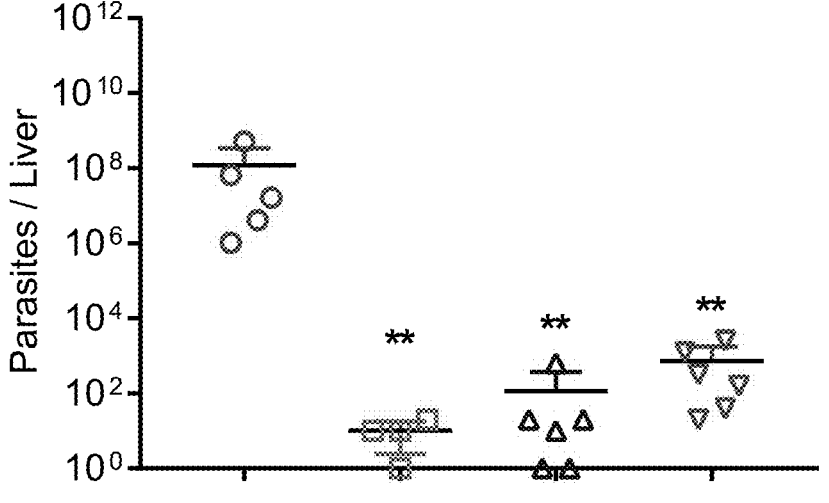

Using LmCen$^{-/-}$ parasites as a vaccine for use in human clinical trials can utilize parasites grown under current Good Manufacturing Practices (cGMP). LmCen$^{-/-}$ parasites were produced in a bioreactor at small industrial scale under Good Laboratory Practices (GLP). GLP production of LmCen$^{-/-}$ parasites is scalable and can be applied to cGMP production of LmCen$^{-/-}$ parasites. Hamsters were immunized with laboratory-grade (n=4) or GLP-grade (n=6) LmCen$^{-/-}$ parasites. Age matched non-immunized mice were used as the controls (n=5). Six weeks post-immunization, hamsters were challenged with wild type *L. donovani* parasites. Analysis of spleen and liver parasite loads at nine months post-challenge with *L. donovani* showed that control of parasitemia in animals immunized with either GLP-grade LmCen$^{-/-}$ parasites (grown with or without serum) or laboratory-grade parasites was equivalent and was greater compared to non-immunized control hamsters (FIGS. 20A-20B). These data show that GLP-grade LmCen$^{-/-}$ parasites grown without serum induce a similar level of protective immunity as laboratory-grade parasites against visceral infection in a pre-clinical animal model.

In view of the many possible embodiments to which the principles of the disclosed subject matter may be applied, it should be recognized that the illustrated embodiments are only examples of the disclosure and should not be taken as limiting the scope of the disclosure. Rather, the scope of the disclosure is defined by the following claims. We therefore claim all that comes within the scope and spirit of these claims.

---

We claim:

1. A live, attenuated cutaneous or mucocutaneous *Leishmania* species comprising at least one genetic modification, wherein the at least one genetic modification comprises an amastigote growth-arresting modification comprising a functional deletion or genetic inactivation of the centrin gene, and wherein the *Leishmania* species does not comprise any off-target genomic deletions, wherein the *Leishmania* species comprises:

(i) at least one guide RNA (gRNA) comprising SEQ ID NO: 11 or SEQ ID NO: 12;

(ii) a pLdCN vector encoding a Cas9 enzyme; or (iii) both (i) and (ii).

2. The live, attenuated cutaneous or mucocutaneous *Leishmania* species of claim 1, which is capable of growth in serum-free media.

3. The live, attenuated cutaneous or mucocutaneous *Leishmania* species of claim 1, wherein the *Leishmania* species does not comprise an antibiotic-resistance gene.

4. The live, attenuated cutaneous or mucocutaneous *Leishmania* species of claim 1, wherein the *Leishmania* species is a mucocutaneous *Leishmania* species, and the mucocutaneous *Leishmania* species is *L. braziliensis.*

5. The live, attenuated cutaneous or mucocutaneous *Leishmania* species of claim 1, wherein the *Leishmania* species is a cutaneous *Leishmania* species, and the cutaneous *Leishmania* species is *L. major, L. tropica* , or *L. panamensis.*

6. An immunogenic composition, comprising the live, attenuated cutaneous or mucocutaneous *Leishmania* species of claim 1.

7. The immunogenic composition of claim 6, further comprising an adjuvant.

8. The live, attenuated cutaneous or mucocutaneous *Leishmania* species of claim 1, comprising a gRNA comprising SEQ ID NO: 11 and a gRNA comprising SEQ ID NO: 12.

9. The live, attenuated cutaneous or mucocutaneous *Leishmania* species of claim 1, wherein the vector encoding the Cas9 enzyme is a pLdCNLm221410a&b vector.

10. A vaccine, comprising:

the live, attenuated cutaneous or mucocutaneous *Leishmania* species of claim 1.

11. A pharmaceutical composition, comprising a pharmaceutically acceptable carrier and the live, attenuated cutaneous or mucocutaneous *Leishmania* species of claim 1.

12. A live, attenuated cutaneous or mucocutaneous *Leishmania* species comprising a functional deletion or genetic inactivation of the centrin gene, wherein the *Leishmania* species does not comprise an antibiotic-resistance gene, and wherein the *Leishmania* species comprises:

(i) at least one guide RNA (gRNA) comprising SEQ ID NO: 11 or SEQ ID NO: 12;

(ii) a pLdCN vector encoding a Cas9 enzyme; or (iii) both (i) and (ii).

13. The live, attenuated cutaneous or mucocutaneous *Leishmania* species of claim 12, wherein the *Leishmania* species does not comprise any off-target genomic deletions.

14. The live, attenuated cutaneous or mucocutaneous *Leishmania* species of claim 12, which is capable of growth in serum-free media.

15. The live, attenuated cutaneous or mucocutaneous *Leishmania* species of claim 12, wherein the *Leishmania* species is *L. major.*

16. A pharmaceutical composition, comprising a pharmaceutically acceptable carrier and the live, attenuated cutaneous or mucocutaneous *Leishmania* species of claim 12.

* * * * *

SEQUENCE LISTING

```
<160> NUMBER OF SEQ ID NOS: 16

<210> SEQ ID NO 1
<211> LENGTH: 58
<212> TYPE: DNA
<213> ORGANISM: Artificial sequence
<220> FEATURE:
<223> OTHER INFORMATION: Synthetic nucleic acid

<400> SEQUENCE: 1
atcgaagacc tttgtcttct cgcaatcctt ctgctgtttt agagctagaa atagcaag        58

<210> SEQ ID NO 2
<211> LENGTH: 54
<212> TYPE: DNA
<213> ORGANISM: Artificial sequence
<220> FEATURE:
<223> OTHER INFORMATION: Synthetic nucleic acid

<400> SEQUENCE: 2
atcgaagacc caaacttgag agggaaagca acggacacca tgacgagctt actc        54

<210> SEQ ID NO 3
<211> LENGTH: 50
<212> TYPE: DNA
<213> ORGANISM: Artificial sequence
<220> FEATURE:
<223> OTHER INFORMATION: Synthetic nucleic acid

<400> SEQUENCE: 3
atttcgtgct tctcgcaatc cttctcaacg gatgatagtg cgcgtgtgcg        50

<210> SEQ ID NO 4
<211> LENGTH: 564
<212> TYPE: DNA
<213> ORGANISM: Leishmania major

<400> SEQUENCE: 4
atgagtatcg cgagcaacac acctttaagg ccgagcacct ccgcatcgaa cgcgaacacc        60
```

-continued

```
gagctcagca aggatcagct ggaggaaatc cgcgaggcgt tcgacttatt cgacacggat      120
ggcagtggca cgatcgacgt gcgggagctg cgcgttgcca tgcgggcact cggcttcgag      180
cctcgtaagg aggagcttca gcagcttatc aacagcgtca ccggtggcag cggctacgaa      240
gcaaccacta cgcggctgcc gagcgccggc aatgtgaacg cgtccagcga cgtgatcacc      300
ttctcgcagt ttgtgcagat tatgaagcac aaggtgtcac aacgggactc gcgggaggag      360
atgctgaagg cgttcgtgct cttcgacaca gagggcactg gcaagatctc gttccagaac      420
ttgaagcgag tggcggtgga gcttggcgag aacatgacgg acgccgagct gcaggagatg      480
atcgacgagg cggaccgtga cgggacggc gaggtgagcg aggaggagtt tcttcgctta      540
atgaagaaga cgtcgctgta ctaa                                           564
```

```
<210> SEQ ID NO 5
<211> LENGTH: 187
<212> TYPE: PRT
<213> ORGANISM: Leishmania major

<400> SEQUENCE: 5

Met Ser Ile Ala Ser Asn Thr Pro Leu Arg Pro Ser Thr Ser Ala Ser
1               5                   10                  15

Asn Ala Asn Thr Glu Leu Ser Lys Asp Gln Leu Glu Glu Ile Arg Glu
                20                  25                  30

Ala Phe Asp Leu Phe Asp Thr Asp Gly Ser Gly Thr Ile Asp Val Arg
            35                  40                  45

Glu Leu Arg Val Ala Met Arg Ala Leu Gly Phe Glu Pro Arg Lys Glu
        50                  55                  60

Glu Leu Gln Gln Leu Ile Asn Ser Val Thr Gly Gly Ser Gly Tyr Glu
65                  70                  75                  80

Ala Thr Thr Thr Arg Leu Pro Ser Ala Gly Asn Val Asn Ala Ser Ser
                85                  90                  95

Asp Val Ile Thr Phe Ser Gln Phe Val Gln Ile Met Lys His Lys Val
                100                 105                 110

Ser Gln Arg Asp Ser Arg Glu Glu Met Leu Lys Ala Phe Val Leu Phe
            115                 120                 125

Asp Thr Glu Gly Thr Gly Lys Ile Ser Phe Gln Asn Leu Lys Arg Val
        130                 135                 140

Ala Val Glu Leu Gly Glu Asn Met Thr Asp Ala Glu Leu Gln Glu Met
145                 150                 155                 160

Ile Asp Glu Ala Asp Arg Asp Gly Asp Gly Glu Val Ser Glu Glu Glu
                165                 170                 175

Phe Leu Arg Leu Met Lys Lys Thr Ser Leu Tyr
            180                 185
```

```
<210> SEQ ID NO 6
<211> LENGTH: 30
<212> TYPE: DNA
<213> ORGANISM: Artificial sequence
<220> FEATURE:
<223> OTHER INFORMATION: Synthetic nucleic acid

<400> SEQUENCE: 6
atggctgcgc tgacggatga acagattcgc                                      30
```

```
<210> SEQ ID NO 7
<211> LENGTH: 26
<212> TYPE: DNA
<213> ORGANISM: Artificial sequence
```

```
<220> FEATURE:
<223> OTHER INFORMATION: Synthetic nucleic acid

<400> SEQUENCE: 7
ctttccacgc atctgcagca tcacgc                                          26

<210> SEQ ID NO 8
<211> LENGTH: 23
<212> TYPE: DNA
<213> ORGANISM: Artificial sequence
<220> FEATURE:
<223> OTHER INFORMATION: Synthetic nucleic acid

<400> SEQUENCE: 8
cttctcgcaa tccttctgct tgg                                            23

<210> SEQ ID NO 9
<211> LENGTH: 23
<212> TYPE: DNA
<213> ORGANISM: Artificial sequence
<220> FEATURE:
<223> OTHER INFORMATION: Synthetic nucleic acid

<400> SEQUENCE: 9
tccgttgctt tccctctcaa cgg                                            23

<210> SEQ ID NO 10
<211> LENGTH: 60
<212> TYPE: DNA
<213> ORGANISM: Artificial sequence
<220> FEATURE:
<223> OTHER INFORMATION: Synthetic nucleic acid

<400> SEQUENCE: 10
gctctatttc gtgcttctcg caatccttct caacggatga tagtgcgcgt gtgcgttcct    60

<210> SEQ ID NO 11
<211> LENGTH: 102
<212> TYPE: DNA
<213> ORGANISM: Artificial sequence
<220> FEATURE:
<223> OTHER INFORMATION: Synthetic nucleic acid

<400> SEQUENCE: 11
cttctcgcaa tccttctgct gttttagagc tagaaatagc aagttaaaat aaggctagtc    60
cgttatcaac ttgaaaaagt ggcaccgagt cggtgctttt tt                      102

<210> SEQ ID NO 12
<211> LENGTH: 102
<212> TYPE: DNA
<213> ORGANISM: Artificial sequence
<220> FEATURE:
<223> OTHER INFORMATION: Synthetic nucleic acid

<400> SEQUENCE: 12
tccgttgctt tccctctcaa gttttagagc tagaaatagc aagttaaaat aaggctagtc    60
cgttatcaac ttgaaaaagt ggcaccgagt cggtgctttt tt                      102

<210> SEQ ID NO 13
<211> LENGTH: 15
<212> TYPE: PRT
<213> ORGANISM: Artificial sequence
<220> FEATURE:
<223> OTHER INFORMATION: Synthetic amino acid
```

<400> SEQUENCE: 13

Pro Val Ser Lys Met Arg Met Ala Thr Pro Leu Leu Met Gln Ala
1               5                   10                  15

<210> SEQ ID NO 14
<211> LENGTH: 1786
<212> TYPE: DNA
<213> ORGANISM: Leishmania major

<400> SEQUENCE: 14
ggtcagtcta agtggatgag gatgtattat gttttatagt gaggttgagg ggtggcagaa      60
gcggaggtgg aaggagacga gctgccgatt gcgcaactat cagcactggt atctactggg     120
ggttgtagtg tatcgggcct aatccatcga tgggtggcgt agctgcttct gcagtcgccg     180
ttggcacgcg ctctcaagca gtgagggaag ccactctaca tatctagggc gcccgccttt     240
tccgtttcgc ggaagtgttc tcatgctcta tttcgtgctt ctcgcaatcc ttctgcttgg     300
cctgttaccg gggcttaccg cggcatacga cggcttcgtt gtcggtgcat aatgcacccg     360
cgcgtcgtgg agccactcac agtcatttcc gtgtgtgccc tgcattcatc gacagcattc     420
tgcatacagc gtgaacgcgt ctcatagagc atatttcctt tatcgcgttt tcgtttgcac     480
tgccgcgatt tcttttcgtg ggtcgcatca atcaaccatg gctgcgctta cggatgagca     540
gattcgcgag gccttcaacc tcttcgacgc cgacggctct ggggctatcg acgcggagga     600
gatggcgcta gcgatgaagg gtctcggctt cggtgacctg tcgcgcgacg aggtggagcg     660
cattatccgc tccatgcaca cagactccaa cggcctggtg gcgtacggcg agtttgaagc     720
catggtcaag tcgcgcatgg cgcagaagga ctcgccggag gagatcctaa aggcctttca     780
gctcttcgac ctcgataaga aaggaaaaat ctcctttgcg aacttgaagg aggttgcgaa     840
actgctgggt gagaaccccg gcgacgatgt gctgaaggag atgatcgccg aggccgatga     900
ggacggtgat ggcgaggttt cctttgagga gttcaagagc gtgatgctgc agatgcgtgg     960
aaagtagagg acggcgcagg aagcgcttgc gcccttcgcc ttcaccgcgc agaggagatg    1020
cgatggtcaa ggcagtgagg aaaaggccga taccgatcaa gaaattcaaa agttcattgt    1080
catcaagcga agggggctag tggccgaggg ctccggagtg tcaccggagt cacctcgcac    1140
cgcttgacct ctgtctctct ctctctctct ctccttgtcg ctttacctgc cccacctttt    1200 gtgtttcgt ctgattcaac gttctcaata ggtggtgctg ttggtgatga tgatgatcgc    1260
ggtgtgtgcg tgtgcgtgcg tgcgcttcct ttcccatcat catcatcatc tgccttcact    1320
ttgatttctc tttcctttgc gtaggttcgc gccgttcggt tttgggcaga tcttttcttt    1380
cgcttttgta tggttgtgct gtccgtttct atttatgact tcttcgtgat tgtacacccg    1440
gggccgttgt cgtgcgtggc ggcgctgtgg tgtgttgtct gggctgggtg gctctgtccg    1500
ttgctttccc tctcaacgga tgatagtgcg cgtgtgcgtt cctcttcctt cctttatcgt    1560
tttgatcgcc gacaagctcg ctcagtggaa ctcggatagt gtcggagaag agcagggcga    1620 agcccccgc tctgtaacgg caccctttct cactcgttcc ggcgttccac ggagcagtcg    1680
atagatgaac acggcgggaa agttgggaag gcggggagac gctgaatgaa cagggaagga    1740
atagatgtcg tggctgaaaa accaacggaa acaagcgaat cacgat                   1786

<210> SEQ ID NO 15
<211> LENGTH: 14
<212> TYPE: PRT
<213> ORGANISM: Artificial sequence
<220> FEATURE:

-continued

<223> OTHER INFORMATION: Synthetic amino acid

<400> SEQUENCE: 15

Glu Ala Trp Gly Ala Leu Ala Asn Trp Ala Val Asp Ser Ala
1               5                   10

<210> SEQ ID NO 16
<211> LENGTH: 450
<212> TYPE: DNA
<213> ORGANISM: Leishmania major

<400> SEQUENCE: 16
atggctgcgc ttacggatga gcagattcgc gaggccttca acctcttcga cgccgacggc          60 tctgggggcta tcgacgcgga ggagatggcg ctagcgatga agggtctcgg cttcggtgac         120
ctgtcgcgcg acgaggtgga gcgcattatc cgctccatgc acacagactc caacggcctg         180
gtggcgtacg gcgagtttga agccatggtc aagtcgcgca tggcgcagaa ggactcgccg         240
gaggagatcc taaaggcctt tcagctcttc gacctcgata agaaaggaaa aatctccttt         300
gcgaacttga aggaggttgc gaaactgctg ggtgagaacc ccggcgacga tgtgctgaag         360
gagatgatcg ccgaggccga tgaggacggt gatggcgagg tttcctttga ggagttcaag         420
agcgtgatgc tgcagatgcg tggaaagtag                                          450